United States Patent [19]
Carter

[11] Patent Number: 5,830,678
[45] Date of Patent: Nov. 3, 1998

[54] METHOD FOR IDENTIFYING A TARGET PEPTIDE THAT MODULATES THE BINDING OF EPINECTIN LIGAND TO INTEGRIN RECEPTORS

[75] Inventor: William Gene Carter, Winslow, Wash.

[73] Assignee: Fred Hutchinson Cancer Research Center, Seattle, Wash.

[21] Appl. No.: 643,770

[22] Filed: May 6, 1996

Related U.S. Application Data

[63] Continuation of Ser. No. 292,065, Aug. 17, 1994, abandoned, which is a continuation of Ser. No. 154,638, Nov. 18, 1993, abandoned, which is a continuation of Ser. No. 654,103, Feb. 8, 1991, abandoned, which is a continuation-in-part of Ser. No. 607,137, Oct. 30, 1990, abandoned.

[51] Int. Cl.$^6$ .................. G01N 33/53; G01N 33/555; C07K 14/00; C07K 17/00
[52] U.S. Cl. .................... 435/7.24; 435/7.1; 435/7.2; 530/395
[58] Field of Search ..................... 530/350, 395, 530/388.1, 388.2; 435/7.24, 7.1, 7.2, 240.22

[56] References Cited

U.S. PATENT DOCUMENTS

| | | |
|---|---|---|
| 4,016,036 | 4/1977 | Green . |
| 4,304,866 | 12/1981 | Green . |
| 4,769,317 | 9/1988 | Hefton . |

OTHER PUBLICATIONS

Chakravarti et al., J. of Biol. Chem., vol. 265: 10597–10603, Jun. 1990.
Hemler, Annual Review of Immunology, vol. 8:365–400, Jan. 1990.
Hemler et al., J. of Biol Chem., vol. 264: 6529–6535, Apr. 1989.
Kefalides, N.A., *Int. Rev. Connect. Tissue Res.* 6:63–104, 1973.
Vracko, R., *Am. J. Pathol.* 77:314–338, 1974.
Timpl, R. and Martin, G., In:Immunochemistry of Collagen (Furthmayr, H., Ed.), vol. II, pp. 119–150, CRC Press, Boca Raton, FL, 1982.
Laurie, G.W. and Leblond, C.P., *Histochem. Cytochem.* 31:159–163, 1983.
Yurchenko, P. and Schittny, J.C., *FASEB J.* 4:1577–1590, 1990.
Orkin, R.W. et al., *J. Exp. Med.* 145:204–220, 1977.
Timpl, R. et al., *J. Biol. Chem.* 254:9933–9937, 1979.
Chung, A.E. et al., *Cell* 16:277–287, 1979.
Carlin, B et al., *J. Biol. Chem.* 256:5209–5214, 1981.
Kanwar, Y.S. and Farquhar, M.G., *Proc. Natl. Acad. Sci., USA*, 76:4493–4497, 1979.
Hassell, J.R. et al., *J. Biol. Chem.* 260:8098–8105, 1985.
Laemmli, U.K., *Nature* 227:680–685, 1970.
Kleinman, H.K. et al., *Biochemistry* 25:312–318, 1986.
Staehlin, L.A., *Int. Rev. Cytol.* 39:191–283, 1974.
Jones, J.C.R. et al., *Cell Motil. and Cytoskeleton* 6:560–569, 1986.

Shienvold, F.L. and Kelly, D.E., *Cell Tissue Res.* 172:289–307, 1976.
Griepp, E.B. and Robbins, E.S., "Epithelium in Cell and Tissue Biology," L. Weiss, Ed.), Urban & Swarzenburg, Inc., Baltimore, MD, 1988.
Burridge, K. et al., *Ann. Rev. Cell Biol.*, 4:487–525, 1988.
Stepp et al., *Proc. Natl. Acad. Sci.* 87:8970–8974, 1990.
Carter, W.G., *J. Cell Biol.* 111:3141–3154, 1990.
Carter, W.G. et al., "The Role of Integrins $\alpha2\beta1$ and $\alpha3\beta1$ in Cell–Cell and Cell–Substrate Adhesion of Human Epidermal Cells," *J. Cell Biol.* 110:1387–1404, 1990.
Keene, D.R., et al., *J. Cell Biol.* 104:611–620, 1987.
Sakai, L.Y. et al., *J. Cell Biol.* 103:1577–1586, 1986.
Gipson et al., 1983.
Stanley, J.R., *Clin. Invest.* 94:617–623, 1989.
Tanaka, T. et al., *J. Invest. Dermatol.* 94:617–623, 1990.
Engrall, E. et al., *Cell Regulation* 1:731–740, 1990.
Elices, M.J. et al., *J. Cell Biol.* 112:169–181, 1991.
Green, H. et al., *Proc. Nat. Acad. Sci., USA*, 76:5665–5668, 1979.
Rheinwald and H. Green, *Nature* 265:421–424, 1977.
Kamalti, T. et al., *Development* 106:283–293, 1989.
Kamalti, T. et al., *Exp. Cell Res.* 185:453–463, 1989.
Haake, A.R. and Lane, A.T., *In Vitro Develop. Biol.* 25:560–592, 1989.
Pillai, S. et al., *J. Cell Physiol.* 134(2):229–237, 1988.
Wilke, M.S. et al.,*J. Natl. Cancer Inst.* 80:1299–1304, 1988.
Adams, J.C. and Watt, F.M.,*J. Cell Biol.* 107(5):1927–1938, 1988.
Michel, S.R. et al., *J. Invest. Dermatol.* 88:301–305, 1987.
Eckert, R.L. and Green, H., *Cell* 46:583–589, 1986.
Eckert, R.L. and Rorke, E.A., *Environ. Health Perspect.* 80:109–116, 1989.
Watt, F.M., *J. Cell Biol.* 98:16–21, 1984.
Murphy, G.F., et al., *J. Invest. Dermatol.* 82:453–457, 1984.
Simon, M. and Green, H., *J. Invest. Dermatol.* 92:721–724, 1989.
Parentau, N.L. et al., *Proc. Natl. Acad. Sci., USA* 84:7571–7575, 1987.
Hronis, T.S. et al., *Cancer Res.* 44:5797–5804, 1984.
Cline, P.R. and Rice, R.H., *Canc. Res.* 43:3203–3207, 1983.
Watt, F.M., *J. Invest. Dermatol.* 81(1 Suppl.):100s–103s, 1983.

(List continued on next page.)

*Primary Examiner*—Frank C. Eisenschenk
*Assistant Examiner*—Patrick Nolan
*Attorney, Agent, or Firm*—Christensen O'Connor Johnson & Kindness PLLC

[57] ABSTRACT

A substantially pure epinectin covalently linked glycoprotein complex is disclosed having a ligand portion binding at least to the $\alpha_3\beta_1$ integrin receptor for use in modifying cellular adhesion to a substratum. Also disclosed are specific binding partners for epinectin, as exemplified by monoclonal antibody, and $\alpha_3\beta_1$ and $\alpha_6\beta_4$ integrin receptor peptides for use as inhibitors, antagonists, and agonists of receptor binding to epinectin ligand.

4 Claims, 21 Drawing Sheets

OTHER PUBLICATIONS

Simon, M. and Green, H., "Participation of Membrane–Associated Proteins in the Formation of the Cross–Linked Envelope of the Keratinocyte," *Cell* 36:827–834, 1984.
Simon, M. and Green, H., "Enzymatic Cross–Linking of Involucrin and Other Proteins by Keratinocyte Particulates in Vitro," *Cell* 40:677–683, 1985.
Martin, G. and Timpl, R., "Laminin and Other Basement Membrane Components," *Ann. Rev. Cell Biol.* 3:57–85, 1987.
Beck, K. et al., *FASEB* 4:148–160, 1990.
Hynes, R.O., *Cell* 48:549–554, 1987.
Rouslahti, E., *Ann. Rev. Biochem.* 57:375–413, 1988.
Hemler, M.E., "Adhesive protein receptors on hematopoietic cells," *Immunol. Today* 9:109–113, 1988.
Buck, C.F. and Horwitz, A.F., *Ann. Rev. Cell Biol.* 3:179–205, 1990.
Tamura, R.N. et al., *J. Cell Biol.* 111:1593–1604, 1990.
Wayner, E.A. e al., *J. Cell Biol.*, 107:1881–1891, 1988.
DeLuca, M. et al., *Proc. Natl. Acad. Sci. USA*, 87:6888–6892, 1990.
Wayner, E.A. and Carter, W.G., *J. Cell Biol.* 105:1873–1884, 1987.
Santoro, 1986.
Elices, M.J. and Hemler, M.E., *Proc. Natl. Acad. Sci. USA* 86:9906–9910, 1989.
Langvino et al., 1989.
Lotz, M.M. et al., *Cell Regulation* 1:249–257, 1990.
Sonnenberg, A. et al., *J. Cell Biol.* 110:2145–2155, 1990.
Gehlsen, K.R. et al., *J. Biol. Chem.* 264:19034–19038, 1989.
Adams, J.C. and Watt, F.M., *Cell* 63:425–435, 1990.
Stanely, J.R., *J. Clin. Invest.* 83:1443–1448, 1989.
Kaufmann, R. et al., *J. Cell Biol.* 109:1807–1815, 1989.
Larjava, H. et al., *J. Cell Biol.* 110:803–815, 1990.
Hadley et al., *J. Cell Biol.* 101:1511–1522, 1985.
Madison et al., 1985.
Carey, D. and Todd, M., unpublished results and L. Reid, unpublished results cited in Kleinman et al., #13, above.
Bernard, B.A. et al., *Canc. Res.* 45:1707–1716, 1985.
Said, J.M. et al., *J. Invest. Dermatol.* 82:449–452, 1984.
Levitt, M.L. et al., *Cancer Res.* 50:120–128, 1990.
Peterson, L.L. et al., *J. Invest. Dermatol.* 81(1 Suppl.):45s–100s, 1983.
Kvedar, J.C. et al., *Arch. Pathol. Lab. Med.* 110:183–188, 1986.
Elsayed, A. et al., *Gynecol. Oncol.* 26:25–34, 1987.
Harris, H. and Bramwell, M.E., *J. Cell Sci.* 87:383–388, 1987.
Bernard, B.A. et al., *Br. J. Dermatol.* 112:647–653, 1985.
Schaumberg–Lever, W.F., *J. Invest. Dermatol.* 64:47–49, 1979.
Holubar, K. et al., *J. Invest. Dermatol.* 64:220–225, 1975.
Honigsmann, H., et al., *J. Invest. Dermatol.* 66;262, 1976.
Nieboer, C. et al., *Br. J. Hematol.* 106:419–422, 1983.
Fine, J.D. et al., *J. Invest. Dermatol.* 82:39–43, 1984.
Yaoita, H. et al., *Invest. Dermatol.* 76:288–292, 1981.
Stanley, J.R. et al., *Cell* 24:897–903, 1981.
Nisengard, R.J. et al., *Oral Surgery* 40:365–375, 1975.
Woodley, D.T. et al., *N. Engl. J. Med.* 310:1007–1013, 1984.
Fine, J.D., *Collagen Rel. Res.* 5:369–377, 1985.
Kaur, P. and McDougall, J.K., *J. Virol.* 62:1917–1924, 1988.
Kaur, P. et al., *J. Gen. Virol.* 70:1261–1266, 1989.
Wayner, E.A. et al., *J. Cell Biol.* 109:1321–1330, 1989.
Kunicki et al., 1988.
Carter, W.G., *J. Biol. Chem.* 257:13805–13815, 1982.
Oi and L. Herzenberg, In: *Selected Methods in Cellular Immunology* (B.B. Mishell and S.M. Shiigi, Eds.), W.H. Freeman & Co. Publishers, San Francisco, CA, pp. 351–373, 1980.
Taggart and Samloff, *Science* 219:1228–1230, 1983.
Neylakh, A.A. et al., *Exp. Cell Res.* 149:387–396, 1983.
Aumailley, M. et al., *Exp. Cell Res.* 188:55–60, 1990.
Katz, S.I., *J. Amer. Acad. Dermatol.* 11:1025–1037, 1984.
Haber et al., *J. Amer. Acad. Dermatol.* 12:836–844, 1985.
Mar, H. and Wight, T.N., In: *Colloidal Gold: Principles, Methods, and Applications*, vol. 2 (Ed. M.A. Hayat), Acad. Press, Inc., N.Y., 1989.
Boyce, S.T. and Ham, R.G., *J. Tiss. Cult. Meth.* 9:83–93, 1985.
Towbin et al., *Proc. Natl. Acad. Sci. USA* 76:4350–4354, 1979.
Wolpert, L., *J. Cell Sci.,* Suppl. 10:1–9, 1988.
Plantefaber, L.C. and Hynes, R.O., *Cell* 56:281–290, 1989.
Izzard, C.S. and Lochner, L.R., *J. Cell Sci.* 21:129–159, 1976.
Potten, C.S. and Morris, R.J., *J. Cell Sci.* 10:45–62, 1988.
Hemler, M.E. et al., *J. Biol. Chem.* 264:6529–6535, 1989.
Hemler, M.E. et al., *J. Biol. Chem.* 263:7660–7665, 1988.
Ekblom, P., *FASEB J.* 3:2141–2150, 1989.
Dang, N.H. et al., *J. Exp. Med.* 172:649–652, 1990.
Sanes, J.R., *J. Exp. Med.* 111:1685–1699, 1990.
Hogervorst, F. et al., *EMBO J.* 9:765–770, 1990.
Gordon, J.I., *J. Cell Biol.* 108:1187–1194, 1989.
Sonnenberg, A. et al., *Nature* 336:487–489, 1988.
Tew, J.G. et al., *Immunol. Rev.* 117:185–211, 1990.
Carter, W.G. et al., "Epiligrin, a New Cell Adhesion Ligand for Integrin $\alpha 3\beta 1$ in Epithelial Basement Membranes," *Cell* 65:599–610, 1991.
Domloge–Hultsch, N. et al., "Epiligrin, the Major Human Keratinocyte Integrin Ligand, Is a Target in Both an Acquired Autoimmune and an Inherited Subepidermal Blistering Skin Disease," *J. Clin. Invest.* 90:1628–1633, 1992.
Henikoff, S. and Henikoff, J.G., "Amino acid substitution matrices from protein blocks," *Proc. Natl. Acad. Sci. USA* 89:10915–10919, 1992.
Maniatis, T. et al., "Agarose Gel Electrophoresis," In: *Molecular Cloning: A Laboratory Manual;* Cold Spring Harbor Laboratory, Cold Spring Harbor, New York, pp. 150–185, 382–386, 1982.
Rousselle, P. et al., "Kalinin: An Epithelium–Specific basement membrane adhesion molecule that is a component of anchoring filaments," *J. Cell Biol.* 114(3):567–576, 1991.
Sanger, F. et al., "DNA sequencing with chain–terminating inhibitors," *Proc. Natl. Acad. Sci. USA* 74(12):5463–5467, 1977.
Verrando, P. et al., "Monoclonal Antibody GB3, A new probe for the study of human basement membranes and hemidesmosomes," *Exp. Cell. Res.* 170:116–128, 1987.
Verrando, P. et al., "Monoclonal antibody GB3 defines a widespread defect of several basement membranes and a keratinocyte dysfunction in patients with lethal junctional epidermolysis bullosa," *Lab. Invest.* 64(1):85–92, 1991.
Wayner, E.A. et al., "Epiligrin, A component of epithelial basement membranes, is an adhesive ligand for $\alpha 3\beta 1$ positive T lymphocytes," *J. Cell Biol.* 121(5):1141–1152, 1993.
Young, R.A. and Davis, R.W., "Efficient isolation of genes by using antibody probes," *Proc. Natl. Acad.Sci. USA* 80:1194–1198, 1983.
Dean et al., *Affinity Chromotography*, IRL Press, 1985.

Creighton, *Protein Function*, IRL Press, 1990.

Enerstein, *J. Investigative Dermatol.* 91:34–38, 1988.

Ehrig, K. et al., "Merosin, a Tissue–specific basement membrane protein, is a laminin–like protein," *Proc. Natl. Acad. Sci. USA* 87:3264–3268, 1990.

Nagayoshi, T. et al., "Human laminin A chain (LAMA) gene: chromosomal mapping to locus 18p11.3," *Genomics* 5:932–935, 1989.

Nissinen, M. et al., "Primary structure of the human laminin A chain," *Biochem J.* 276:369–379, 1991.

Noonan, D.M., et al., "The complete sequence of perlecan, a basement membrane heparan sulfate proteoglycan, reveals extensive similarity with laminin A chain, low density lipoprotein–receptor, and the neural cell adhesion molecule," *J. Biol. Chem.* 266:22939–22947, 1991.

Sasaki, M. et al., "Laminin, a multidomain protein," *J. Biol. Chem.* 263:16536–16544, 1988.

Sasaki, M. et al., "The laminin B2 chain has a multidomain structure homologous to the B1 chain," *J. Biol. Chem.* 262:17111–17117, 1987.

Sasaki, M. et al., "Sequence of the cDNA encoding the laminin B1 chain reveals a multidomain protein containing cysteine–rich repeats," *Proc. Natl. Acad. Sci. USA* 84:935–939, 1987.

Verrando, P. et al., "The new basement membrane antigen recognized by the monoclonal antibody GB3 is a large size glycoprotein: modulation of its expression by retinoic acid," *Biochim. Biophys. Acta* 942:45–56, 1988.

Hemler, M.E., *Ann. Rev. Immunol.*, 8:365–400, 1990.

METHOD FOR IDENTIFYING A TARGET PEPTIDE THAT MODULATES THE BINDING OF EPINECTIN LIGAND TO INTEGRIN RECEPTORS

This application is a continuation of U.S. Ser. No. 08/292,065 filed Aug. 17, 1994, now abandoned, which is a continuation of U.S. Ser. No. 08/154,638 filed Nov. 18, 1993, now abandoned, which is a continuation of U.S. Ser. No. 07/654,103 filed Feb. 8, 1991, now abandoned, which is a Continuation-in-part of Ser. No. 07/607,137 filed Oct. 30, 1990, now abandoned.

1. FIELD OF THE INVENTION

The invention relates generally to epithelial cell receptors and ligands which are useful for adhering epithelial cells to a substratum.

2. BACKGROUND OF THE INVENTION

The invention is predicated upon a basic understanding of epithelial cells and tissues studied. Such epithelia, which cover free surfaces and line body cavities and ducts, have been studied microscopically for at least three centuries. Recently the biochemistry and molecular biology of epithelial cells and tissues have been extensively investigated. However, the seemingly simple question of how the cells in epithelial tissues are driven to become specialized has remained unanswered. The present invention provides reagents that allow us for the first time to unravel the inter- and intracellular signals that direct epithelial cell differentiation. More fundamentally, the subject reagents permit one to finally decipher what has been a tangled web of suspected interactions involving a wide variety of cell types, some of them non-epithelial, in order to understand and modulate at a molecular level how the cells are driven to differentiate to fulfill specialized functions in the body. Pertinent background information concerning these heretofore disparate systems follows.

2.1 ABBREVIATIONS USED IN THE DISCLOSURE

By way of introduction, the following abbreviations are used in this disclosure:

BPA, Bullous Pemphigoid Antigen;
CD3, cellular determinant #3, a lymphocyte surface antigen marker;
CP, Cicatrical pemphigoid, an autoimmune dermatological disease;
EBA, Epidermolysis bullosa acquisita, an autoimmune dermatological disease;
ECM, extracellular matrix;
FAs, focal adhesions;
HD-BSA, heat denatured bovine serum albumin;
HFK(s), human foreskin keratinocyte(s);
HFK-ECM, human foreskin keratinocyte-extracellular matrix;
kd, kilodaltons of molecular mass as determined by SDS-PAGE;
MAbs, monoclonal antibodies;
Mr, molecular radius by SDS-PAGE, approximating molecular mass;
SACs, stable anchoring contacts;
SDS-PAGE, sodium dodecyl sulfate-polyacrylamide gel electrophoresis; and, the integrin receptors $\alpha_3\beta_1$, $\alpha_2\beta_1$ and, $\alpha_6\beta_4$. Throughout the specification, the notation "(#)" is used to refer to the documents listed in the appended Citations section.

2.2 EPITHELIAL CELLS

The invention is predicated upon a basic understanding of epithelial cells and tissues studied. Such epithelia, which cover free surfaces and line body cavities and ducts, have been studied microscopically for at least three centuries. Recently the biochemistry and molecular biology of epithelial cells and tissues have been extensively investigated. However, the seemingly simple question of how the cells in epithelial tissues are driven to become specialized has remained unanswered. The present invention provides reagents that allow us for the first time to unravel the inter- and intracellular signals that direct epithelial cell differentiation. More fundamentally, the subject reagents permit one to finally decipher what has been a tangled web of suspected interactions involving a wide variety of cell types, some of them non-epithelial, in order to understand and modulate at a molecular level how these cells are driven to differentiate to fulfill their specialized functions in the body. Pertinent background information concerning these heretofore disparate systems follows.

The significance of epithelial tissues as a protective barrier is readily apparent in the body as the lining of body cavities, blood vessels, digestive tract, mammary glands, urogenital, endocrine, reticuloendothelial systems, respiratory surfaces, placenta, and surrounding the nerves and brain. The epithelia also forms the basis for the epidermis, cornea, and conjunctiva.

2.3 Epithelial tissues are rather unique in their ability for continuous regulated self-renewal, and in their ability to polarize and control cellular division and the subsequent differentiation of the daughter cells. In attempting to explain how epithelial cells may decide how and when to differentiate, it has been suggested that perhaps gradients of growth factors or interactions with extracellular matrix (ECM) may influence the cells. However, the biochemical mechanisms remain largely unknown.

2.4 The epithelial basement membrane is a common histological feature of columnar, stratified, and squamous epithelia. Another prominent feature is a proliferative basal (stem) cell layer resting on a basement membrane. When viewed through the light microscope, an epithelial basement membrane may include lucent and dense regions termed, respectively, the Lamina lucida and Lamina densa, which are sandwiched between an overlying cellular stroma (stroma), made up of basal stem cells and fibroblasts, and an underlying collagenous matrix. Basement membranes are thin but continuous sheets that separate epithelium from stroma and surround nerves, muscle fibers, smooth muscle cells, and fat cells (1–4). The molecular composition of the basement membrane varies with specialized cellular functions and with the developmental stages, shape, structure, and architecture of different epithelia (5). In the simplest model, basement membranes contain at least type IV collagen (1, 6–8), laminin (7–8), entactin (9), and heparin sulfate proteoglycans (10–11). When co-electrophoresed in SDS-PAGE (12) under reducing conditions, purified EHS tumor laminin was reported to have apparent molecular sizes of 400 kd and 200 kd, entactin was 158 kd, and nidogen was 100 kd (Kleinman et al., Biochemistry 25:312–318, 1986).

2.5 The human skin, for example, is an epithelial tissue composed of the epidermis and the dermis. The dermis is relatively acellular and composed of secreted cell products, e.g., collagens and heparin-sulfate- and chondroitin-sulfate-proteoglycans. In contrast, the epidermis is essentially cellular, containing a layer of cells resting on a basement membrane, termed the basal (stem) cells that are covered by a layer of cornified cells, termed the stratum corneum. Central questions in skin biology have been, (1) how do the cells in the basal layer commit to become cornified, and (2) how do cells decide which daughter cells will become cornified, and which will remain in the basal layer to provide the germinal basis for future generations of cells? Histological examination provides little insight. The viable inner malpighian layers of the skin, from which the cornified cells arise, are composed of the basal cell layer, the stratum spinosum and the stratum granulosum. The cell types in these areas include at least keratinocytes, melanocytes, Merkel cells, Langerhans cells, and migratory immune cells. Cell division in the basal (stem) cell layer forms the basis for the continuous self-renewal of the skin, and it is thought that decisions on the fate of the daughter cells are made in this layer.

2.6 Two types of daughter cells appear to be created by cell division in the basal (stem) cell layers of the skin: namely, the first daughter cell, which will continue to divide; and the second daughter cell, which will differentiate and ultimately become cornified. Distinctive cellular features that may define stages in the differentiation of the second daughter cell include at least the acquisition first, of a flattened cell shape with cytoplasmic keratohyalin granules, ivolucrin, and cytokeratin filaments (characteristics of cells in the stratum spinosum); second, of greater amounts of cytoplasmic keratin and a submembranous envelope formed of proteins cross-linked by epidermal transglutaminase (characteristics of cells in the stratum granulosum); and third, the acquisition of distinguishing features associated with cornified anuclear cells such as extensively cross-linked dense submembranous envelopes (i.e., characteristics of cells in the stratum corneum). The molecular mechanisms determining "first daughter" and "second daughter" status, as well as the mechanisms which control epidermal cell differentiation into cornified anuclear cells, are largely unknown, but these mechanisms appear to be coordinated; i.e., cells enter and leave the malpighian layer at approximately the same rate; they appear to be polarized, i.e., from the basal (stem) cell layer to the apical cornified layers; and they appear to be self-regulating, i.e., processes by which the cornified layers are renewed can effectively compensate for variation in the rate of mechanical sloughing of cells from the surface in different parts of the body. The molecular processes by which this remarkable coordination of cells is achieved in skin or other epithelial tissues are largely unknown, at present.

2.7 The attachment of proliferating basal (stem) cells to the basement membrane occurs at limited points of cellular contact. Contact of epithelial cells, in general, with the basement membrane has been thought to have potential functional significance for maintaining cellular polarization necessary for asymmetric cell division, e.g., to give rise to the distinctively different types of daughter cells, as well as for sustaining the continuous morphogenetic process through which progeny of stem cells differentiate into cornified epithelial cells in skin or into Schwann cells and cells of the spinous strata surrounding nerves. However, there has been (and is currently) a lack of detailed knowledge regarding the cellular biology and molecular biochemistry involved in these postulated polarization and morphogenetic processes. Thus, the mechanisms controlling proliferation of stem cells and commitment of the daughter cells to differentiation are largely unknown.

2.8 The ultrastructure of the attachment points where basal cells are in contact with the basement membrane exhibits characteristic features that are identifiable in appropriately fixed and stained tissues (and cultures). The ultrastructural features have been termed hemidesmosomes (14–16), focal adhesions (17, 18), and hemidesmosome-like stable anchoring contacts (SACs) (19). Focal adhesions and SAC/hemidesmosomes are structurally and functionally distinct adhesion structures (19, 20). Focal adhesions have been observed in motile cells in association with actin-containing stress fibers (20, 21), while SACs appear to be distinguished as a structural component of stationary cells which only form in vitro after cells stop migrating. The function of SACs and focal adhesions is currently not clear, either with respect to their possible role in motility or to other possible roles in the cell biology of the epidermis. However, it has been observed that the Lamina densa may be connected to stroma through anchoring fibrils (22), such as those observed in cells which appear to be linked to hemidesmosomes (23–25). SAC/hemidesmosome structures have also been observed to be associated with cytoplasmic intermediate filaments (26, 27) which have a Bullous pemphigoid antigen (BPA) identifiable by indirect immunofluorescence.

2.9 Studies of basal cell interactions with basement membranes have been complicated by lack of suitable in vitro model systems as well as by changes occurring in the structure, shape, and composition of basement membranes during development and acquisition of specialized cellular functions (5). There has been a near total lack of in vitro models by which basal (stem) cells might be studied. Keratinocytes are one in vitro epithelial model system. These cells are not basal (stem) cells, but they do represent a major cellular constituent of epidermis. Human keratinocytes have been isolated and cultured from stratified or squamous epithelia in vitro under controlled conditions either using fibroblast feeder layers and conditioned medium (28–30); medium containing at least epidermal growth factor (31); keratinocyte growth medium (KGM) containing at least hydrocortisone, low-calcium, insulin, and insulin-like growth factor-1 (32, 33) serum-free (34, 35) or supplemented MCDB 153 basal nutrient medium (36). One recent study has suggested that 85–90% of keratinocyte clones, derived from growing and cloning normal human skin keratinocytes, may be derived from the basal (stem) cell layer and 10–15% from the suprabasal layers of the epidermis (36). The presumptive "suprabasal" keratinocytes expressed markers of terminal differentiation (i.e., ivolucrin) but still possessed the ability to synthesize DNA. These findings suggested to the investigators that some "suprabasal" keratinocytes may exist in an altered state of "non-terminal" differentiation wherein they are still capable of cell division (36). Others have termed possibly related strains of keratinocytes "nondifferentiating keratinocytes" (37). Ivolucrin is one marker for keratinocyte differentiation in vitro. It is a cytosolic protein of human keratinocytes with a reported apparent Mr of 140 kd on SDS-PAGE (38); the gene has recently been reportedly cloned (39) and its regulation studied in cells in vitro (40). Ivolucrin is useful as a marker for an early stage in the terminal differentiation of keratinocytes since it is synthesized shortly after keratinocytes leave the basal (stem) cell layer, at a time when cellular enlargement has begun, but before onset of envelope cross-linking (41, 42). Ivolucrin has been reported to have undergone a relatively rapid evolution with the possibility of 3 alleles in monkeys (43, 44). Cytokeratins are a second useful marker for keratinocyte differentiation in vitro. There are at least five cytokeratins which may be expressed by keratinocytes in vitro using Western immunoblot analysis and commercially available monoclonal antibodies AE1 and AE3: these include cytokeratins No. 5 (58 kd), No. 6 (56 kd); No. 14/15 (50 kd); No. 16 (48 kd); and No. 17 (46 kd) (45). Keratinocyte differentiation can be induced in vitro, at least to the extent that the cells change morphology into cells resembling cornified epithelia. This process can be induced in tissue culture with normal levels of calcium or with ionophores (46, 47). When such keratinocyte differentiation is induced in tissue culture, epidermal transglutaminase can become activated in the cells with coincident development of a cross-linked submembranous protein envelope. During cross-linking, cytosolic ivolucrin becomes associated with the submembranous protein envelope as do two other proteins which are reportedly found in keratinocytes but not in fibroblasts. These two proteins have reported apparent molecular sizes on SDS-PAGE of 210 kd and 195 kd (48). In an in vitro reconstituted system it was suggested that addition of ivolucrin promoted cross-linking of proteins (49). Thus, while keratinocytes are useful as an in vitro model for some molecular processes involved in epithelial differentiation, they are not basal (stem) cells and are clearly distinguished from them with at least ivolucrin as a marker. In addition, the study of keratinocytes has not approached at a molecular level the possible interactions which may occur between receptors in basal (stem) cells and ligands in the basement membrane.

2.10 Ligands which mediate the binding of basal (stem) cells to the epithelial basement membrane are largely unknown. The known basement membrane components in the Lamina lucida layer of the epithelium include at least laminin, nidogen, and heparin sulfate proteoglycan, and in the Lamina densa they include types IV and VII collagen (5, 50, 51). The possible cellular receptors which may bind to these ligands include at least the integrin adhesion receptors (for reviews see 52–55).

2.11 Integrins are a family of receptor glycoproteins with two noncovalently associated polypeptide chains of different molecular sizes (the larger termed the a chain and the smaller the $\beta$), forming a structure termed a heterodimer. The respective chains have amino acid sequence homology, and the integrins serve a similar function at least as receptors for cellular adhesion to extracellular matrix glycoproteins. Six $\alpha$ chains and at least four $\beta$ chains have recently been identified, giving at least 24 different theoretical heterodimers which could act as receptors for cellular adhesion. An alignment of the $\alpha_6$ chain amino acid sequence with the $\alpha_3$ chain reportedly showed approximately 37% identity (56). The molecular events and mechanisms governing control of the biosynthesis and assembly of the different $\alpha$ and $\beta$ chains in different cells and tissues are largely unknown, as is the possible existence of several of the theoretical integrin structures. In T-lymphocytes, as opposed to epithelial cells, the activation of cells with interleukin-2 is correlated with induction of expression of the $\alpha_3\beta_1$ integrin on the cell surface (57).

2.12 Biological functions of integrins in tissues and cells include (1) the possible mediation of the attachment of T- and B-lymphocytes and platelets to basement membrane via integrins $\alpha_3\beta_1$, $\alpha_2\beta_1$, and $\alpha_6\beta_4$ and (2) a possible role in hemostasis and homeostasis for these integrins, the latter by contributing to the maintenance of the structure of the integument and epithelia (19–21; 57, 58).

2.13 Possible associations between integrin receptors and laminin ligands include reports that the $\alpha_2\beta_1$ integrin is a collagen receptor in human fibrosarcoma cells (59, 60) with affinity for laminin in some cells (61, 62). $\alpha_6\beta_4$ has also been suggested as a laminin receptor in human colon carcinoma cells (63), but it reportedly does not bind to the E8 domain of laminin which is a ligand domain interacting with the $\alpha_6\beta_1$ integrin receptor (64). $\alpha_3\beta_1$ is reportedly one of the most widely expressed integrins in tissues and in epithelial and non-epithelial cells in culture. It also has been suggested as a possible nonspecific laminin receptor in cells (57, 65). The reports of an association of $\alpha_3\beta_1$ with laminin either have not determined the apparent binding affinity of the interaction or have determined the association by assays which permit only a relational comparison, i.e., relatively strong or weak. Laminin is reportedly a poor ligand for adhesion of cultured human foreskin keratinocytes (20, 21). In tissue culture, antibody reactive with $\alpha_3\beta_1$ reportedly substantially inhibited adhesion of human foreskin keratinocytes to HFK-extracellular matrix. In contrast, antibody reactive with $\alpha_6\beta_4$ had only a minor effect, but when both antibodies were added together, adhesion of HFK to HFK-ECM was reportedly completely inhibited (20) but no ligand was identified. Thus, it is not apparent whether the interactions of $\alpha_3\beta_1$ and $\alpha_6\beta_4$ with laminin are physiologically meaningful, whether laminin is a ligand, or what the physiologically meaningful ligands for these integrin receptors may be in skin.

2.14 The distribution of the $\alpha_6\beta_4$, $\alpha_3\beta_1$ and $\alpha_2\beta_1$ integrins in tissues is varied. The $\alpha_6\beta_4$ integrin receptor is limited primarily in epithelial and Schwann cells surrounding myelinated nerves (64) and is down-regulated in differentiated spinal cells (20, 21, 66). SAC/hemidesmosome structures have also been observed to be associated with Bullous pemphigoid antigen (27, 67). In contrast, the $\alpha_3\beta_1$ and $\alpha_2\beta_1$ integrins are widely expressed in tissue and particularly evident in proliferating epithelial cells (20, 21) and in transformed cells and activated lymphoblastoid cells. At the ultrastructural level, the $\alpha_6\beta_4$, $\alpha_3\beta_1$ and $\alpha_2\beta_1$ integrins have been visualized by association with focal adhesions (rather than SACs) and actin-containing stress fibers in motile cells (20, 21). In addition, $\alpha_3\beta_1$ (68) and possibly $\alpha_2\beta_1$ have been implicated in cell-cell adhesion because they have been observed to relocate from areas of cell-substrate contact to areas of cell-cell contact in cells, and because antibodies to the $\beta_1$ integrin polypeptide inhibit cell-cell contact in cells in vitro (20, 21, 69). In general, $\alpha_6\beta_4$, $\alpha_3\beta_1$, and $\alpha_2\beta_1$ appear only in the proliferating basal cell layer; $\alpha_6\beta_4$ appears to be restricted to regions of the stem cell basal plasma membrane (58, 20, 21); $\alpha_3\beta_1$ appears on basal lateral and apical regions of the stem cell plasma membrane; and $\alpha_2\beta_1$, appears primarily on the apical and lateral regions of the stem cell plasma membrane (59, 20, 21). Thus, while integrins $\alpha_3\beta_1$ and $\alpha_6\beta_4$ have been recognized as glycoproteins involved in cell-substrate contact in vitro, the available information has created a tangled web which does not permit a determination of which interactions may be physiologically meaningful in vivo.

2.15 Integrin receptors are reported to play a possible role in lymphocyte activation. It has been reported recently that in T-lymphocytes, rather than epithelial cells, the interaction of cells containing the $\alpha_3\beta_1$ integrin receptor with collagen and a second signal such as initiated by binding of antibody to CD3 to the cell surface integrin receptor may trigger cellular activation. Whether such effects may also be triggered by integrins in non-lymphoid cells is not known, at present. It has been reported that a complex substrate composed of a gel formed from purified laminin, type IV collagen, heparin sulfate proteoglycan, entactin and nidogen induced clustering of melanocytes (13), formation of tubular structures by Sertoli cells (70), in vivo growth of neurons (71), and in vitro growth of Schwann cells and liver cells (72). However, it is not known whether the complex substrate induced these effects, or whether the complex substrate favored the growth of a few cells which already possessed these features. Epithelial cells grown with this complex substrate, in general, were reported to assume a much greater polarity than on plastic, collagen, laminin, or fibronectin, but again the molecular basis for this reported change is at present unclear.

2.16 Malignant transformation of normal human keratinocytes in vitro has been reported to impair their ability to differentiate, stratify, and form cornified epithelia in vitro, and these properties were correlated with inability of the cells to synthesize ivolucrin and re-expression of fetal cytokeratins (73). Studies of ivolucrin tissue distribution in cases of skin and lung carcinoma have also suggested that basal cell carcinomas may be negative for ivolucrin with low transglutaminase activity while squamous cell carcinomas may be positive for ivolucrin (74–77). In these respects the transformed keratinocytes and basal cell carcinomas seemed to resemble basal (stem) cells. However, the validity of such interpretations based on ivolucrin has been brought into doubt by the finding that ivolucrin is universally present in both benign acne and keratotic lesions as well as in malignant lesions in skin (78) or cervical tissues (79).

2.17 The mechanisms by which cancer cells of epithelial origin arise are largely unknown, and since these mechanisms are unknown it is more difficult to imagine how treatments may be structured to restore normal growth control to malignant cells. Recently it has been reported that malignant human cells may be induced to assume a non-malignant phenotype in vitro by fusion with diploid human keratinocytes. The non-malignant phenotype in the fused cells was reportedly correlated with the continued expression of ivolucrin as a marker of keratinocyte terminal differentiation, i.e., cells which reportedly lost the ability to produce ivolucrin during in vitro culture also reacquired the ability to grow progressively in animals (80).

2.18 Mechanisms involved in psoriasis and autoimmune dermatological diseases are also largely unknown. However, it is reported that epidermal tissues may show decreased transglutaminase activity and premature appearance of ivolucrin in the basal cell layer (81), suggesting a possible premature terminal differentiation of basal (stem) cells in this disease, but not suggesting any mechanisms by which this condition may be caused or corrected. Similarly, Bullous pemphigoid (BP), Cicatrical pemphigoid (CP), and Epidemolysis bullosa acquisita (EBA), are autoimmune dermatological diseases where autoantibodies have been reported (in some patients) that bind to antigens in pathological and normal basement membranes. In BP and CP, using immunoelectron microscopy, immunoreactants have been reported to be in skin, and associated with the Lamina lucida (82–86) while, in contrast, EPA immunoreactants reportedly are localized just below the Lamina densa (87). Autoantibodies present in some BP patients' sera also reportedly bound antigens in the Lamina lucida (88, 89) and in EBA they reportedly bound to antigens in the Lamina densa (87, 90). The apparent molecular sizes on SDS-PAGE reported for the BP antigens were 220 kd and 240 kd (91) and the EBA were 290 kd and 145 kd (90). Using suction blisters and split skin techniques to separate the basal layer from the basement membrane, BP antigens (BPA) were reportedly identified in the "roofs" of the blisters and split skin (i.e., associated with the cells and not with the basement membrane) while CP antigens were reportedly located in the "floors" (i.e., associated with the basement membrane) (92, 93). BPA has been associated by immunoelectron microscopy with ultrastructural elements resembling SACs (26, 27). These ultrastructural studies have made the association between the presence of immunoreactants in the Lamina lucida and the antibodies that are present (in some patients) to the antigens presumed to be present on the basal surfaces of the basal (stem) cells in the BP, but it is not clear at present what significance these findings may have for understanding these autoimmune diseases. Similarly, it is not clear at present how these findings may relate to the cell biology and biochemistry of normal epithelia.

3. SUMMARY OF THE INVENTION

The present invention is predicated up on the discovery that adhesion of epithelial and lymphoid cells is modified by an epinectin complex composed of disulfide-linked glycoproteins of 200±20 kd, 170±20 kd, 145±20 kd, and 135±15 kd, with an associated intracellular 36±15 kd glycoprotein. The epinectin complex, as well as constituent epinectin glycoproteins and peptides disclosed herein, are ligands for the $\alpha_3\beta_1$ and $\alpha_6\beta_4$ integrin receptors. Specific binding partners of the epinetin complex and its constituents are useful for modifying adhesion of epithelial and lymphoid cells. Certain embodiments of the invention thereby provide reagents and methods for restoring normal growth in epithelial cells, e.g., in autoimmune disease and carcinoma. Other embodiments provide reagents and methods for inhibiting the binding of activated lymphoid cells to epithelial cells through the integrin receptors, e.g., for controlling inflammation in epithelial tissues.

4. BRIEF DESCRIPTION OF THE DRAWINGS

FIGS. 4A–K illustrate the SACs "ring structures" in which epinectin glycoprotein complex is deposited in ECM, as described on pages 30–33.

FIGS. 5A–5F depict the co-localization of $\alpha_6\beta_4$ (GoH3, FIG. 5-B), epinectin (P1E1, FIGS. 5A, 5C, 5E), BPA (FIG. 5D), and $\alpha_3\beta_1$ (P1F2, FIG. 5F) in the SACs contained in the purified HFK-ECM, as described on pages 32–33.

FIGS. 6A–F demonstrate that attachment of human foreskin fibroblasts to HFK-ECM (FIGS. 6D–F) but not other ECM components, as described on pages 35–36.

Figure 7:
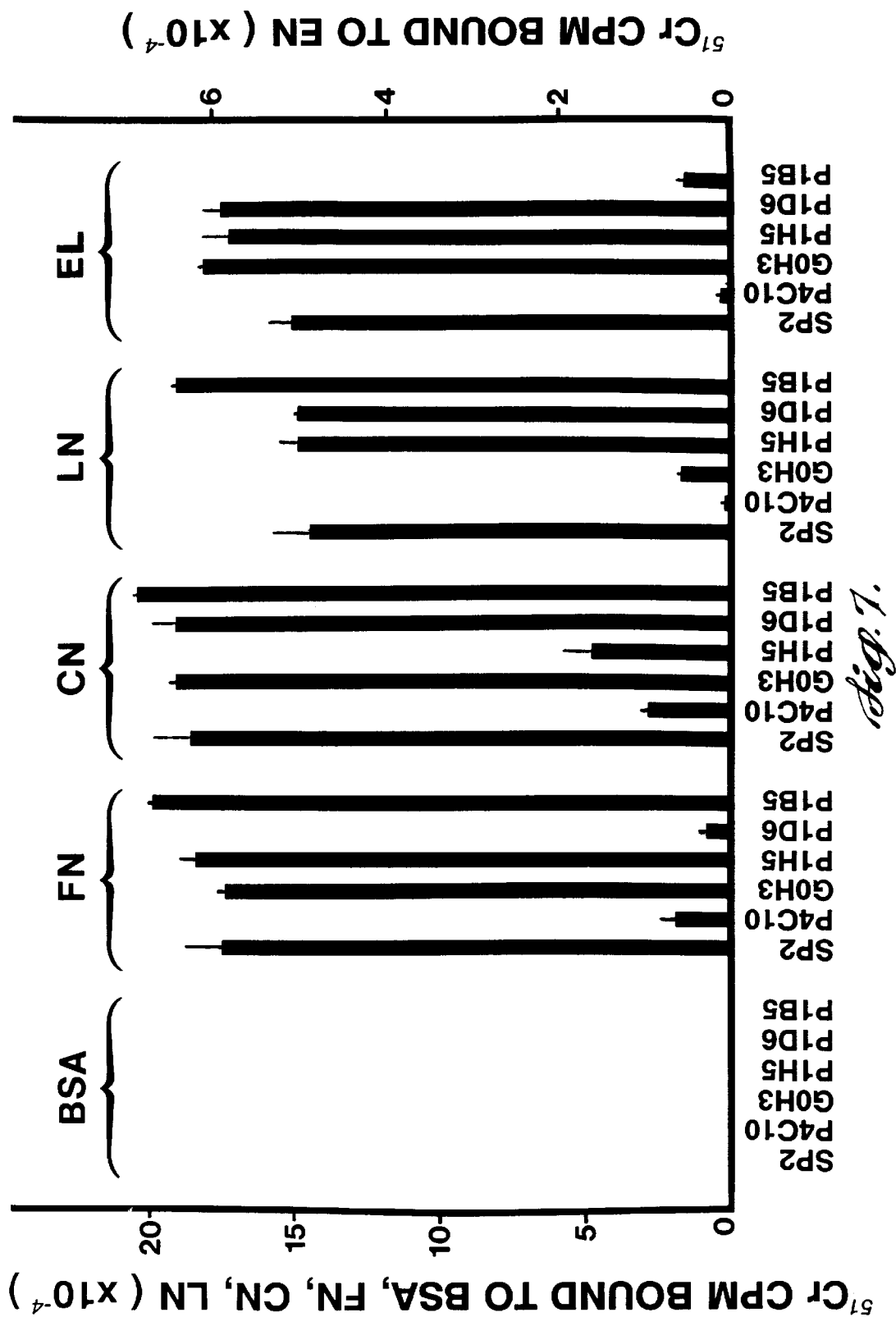

FIG. 7 illustrates a specific test cell assay for epinectin in which specific adherence of cells to epinectin is modulated, as described on pages 37–38.

Figure 8A:
Figure 8B:
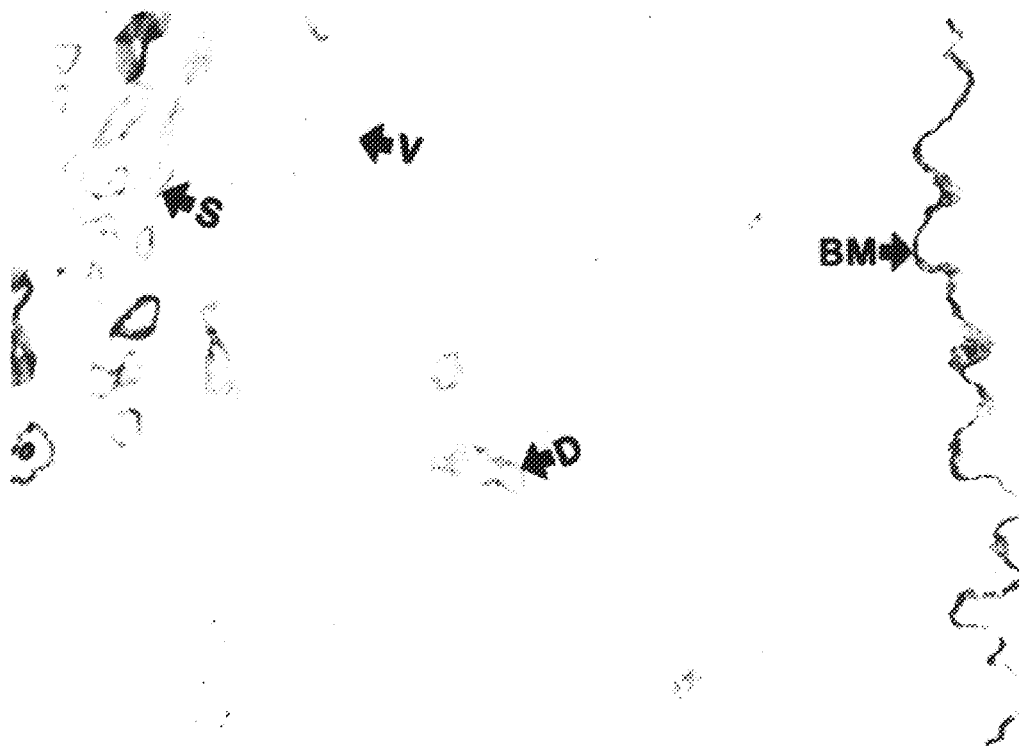
Figure 8C:
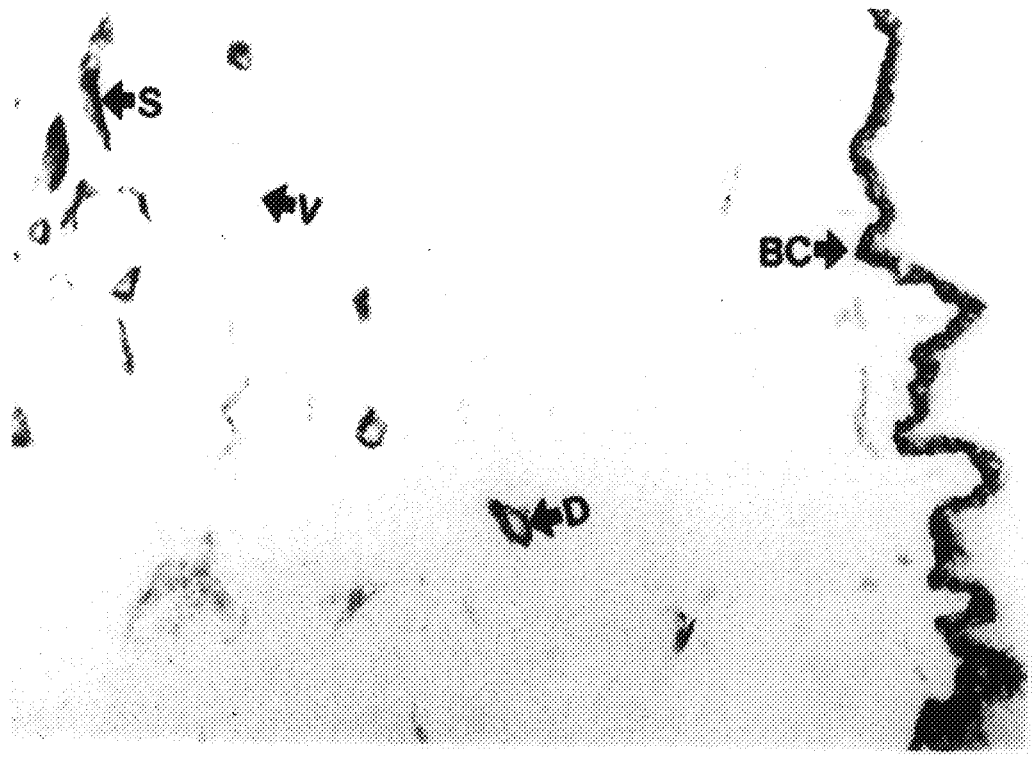
Figure 8D:
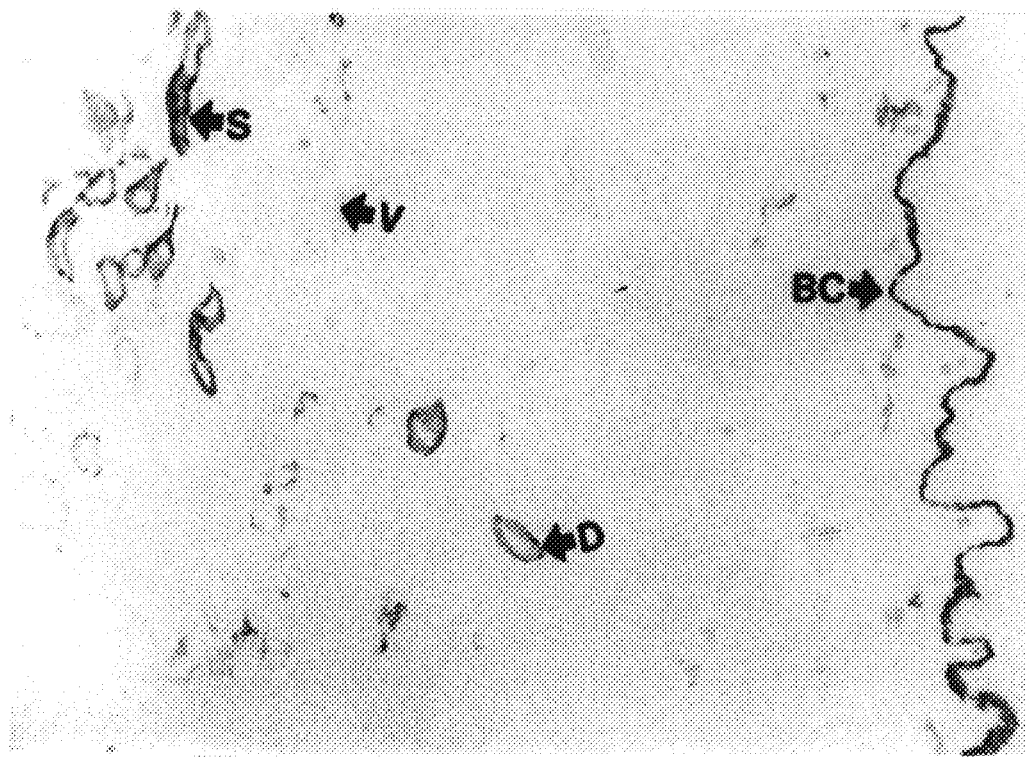
Figure 8E:
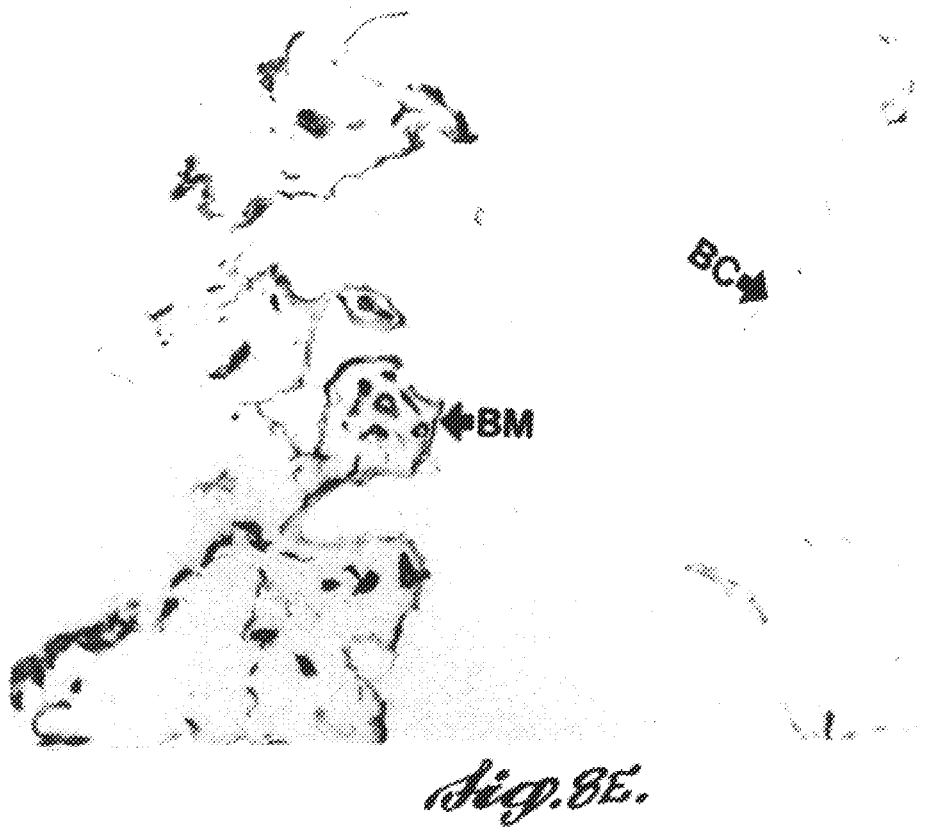
Figure 8F:
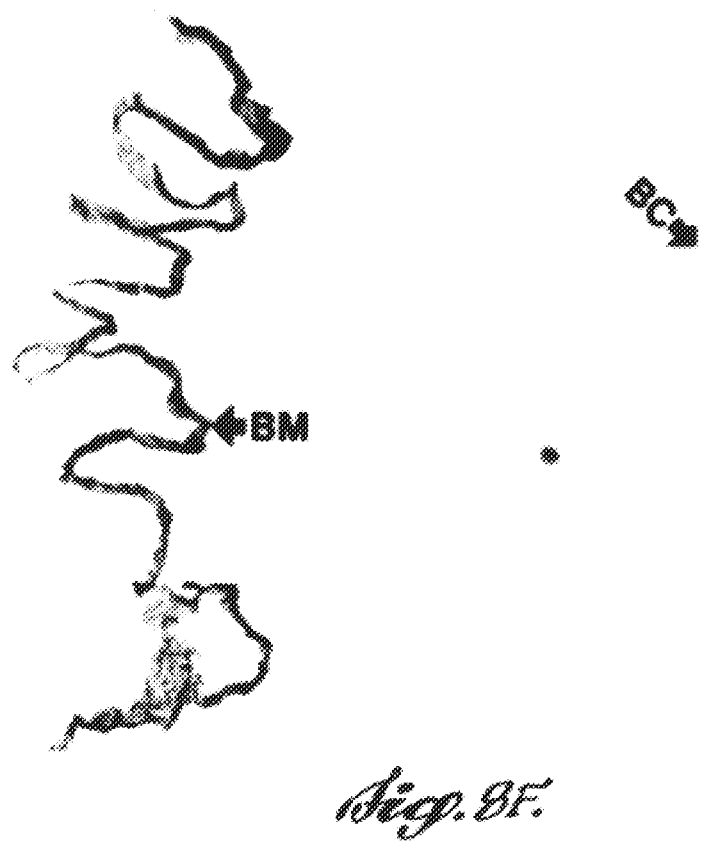
Figure 8G:
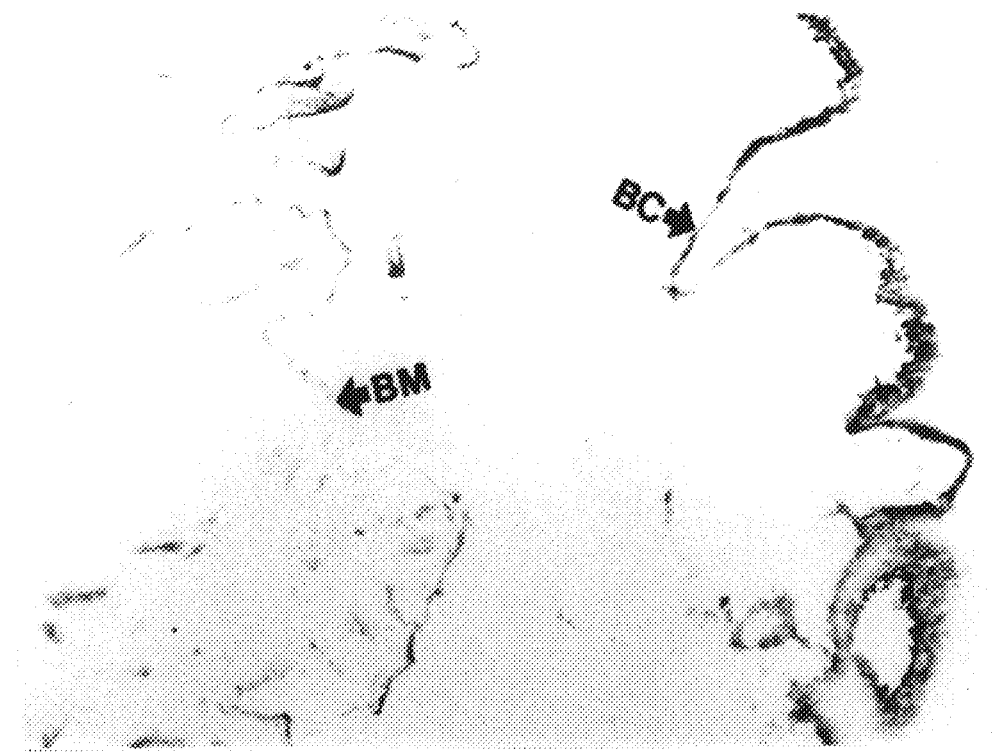
Figure 8H:
Figure 8I:
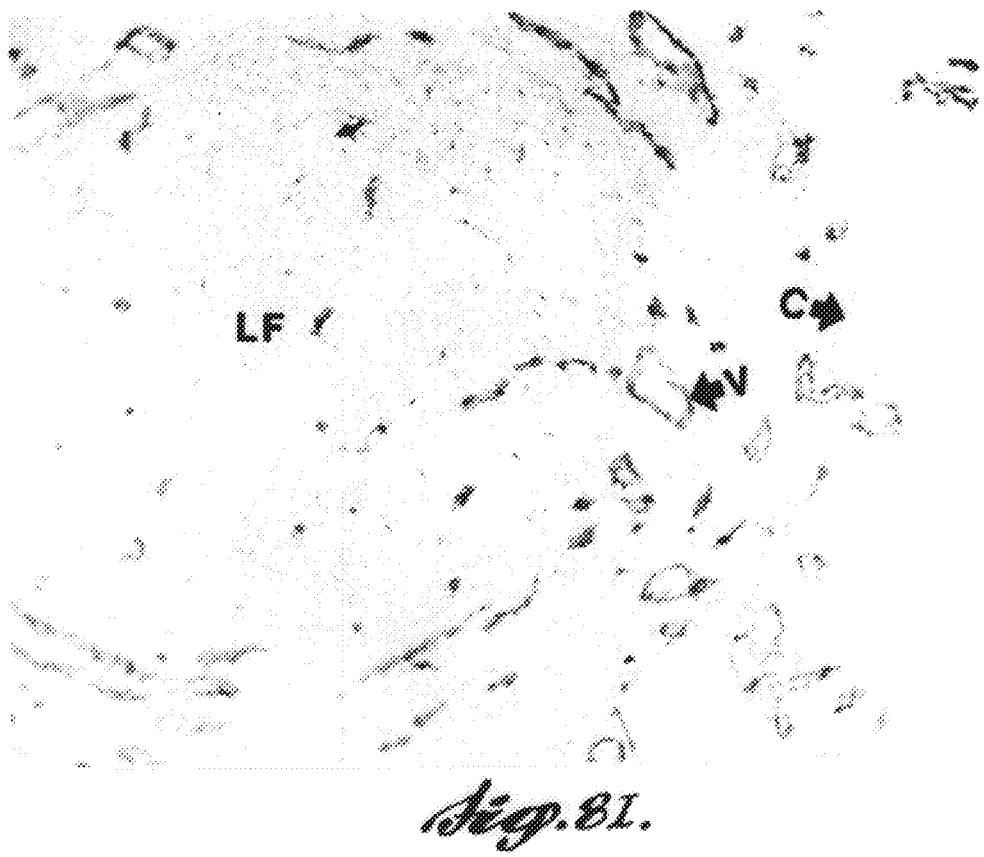
Figure 8J:
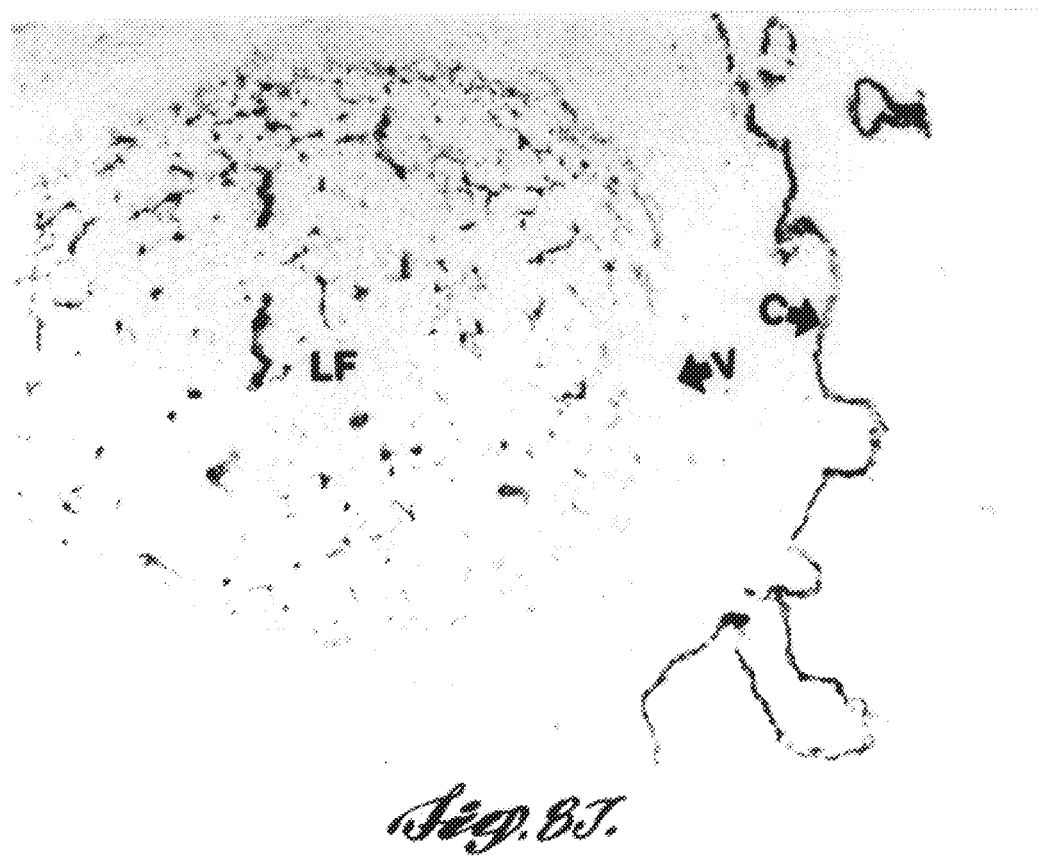
Figure 8K:
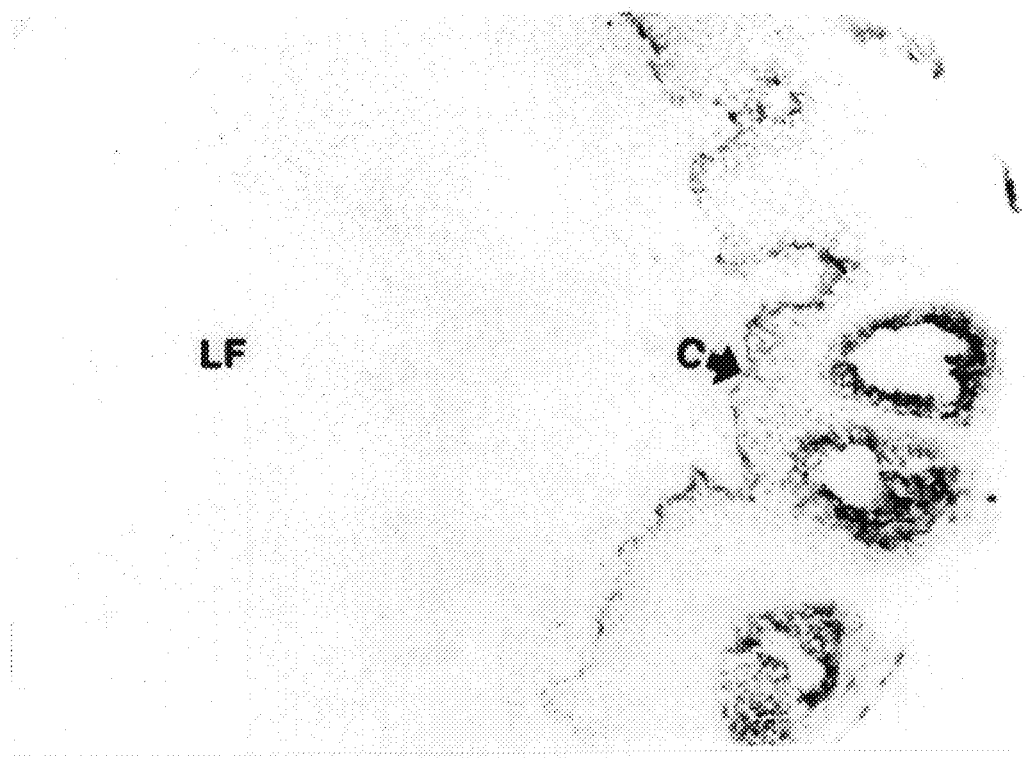
Figure 8L:
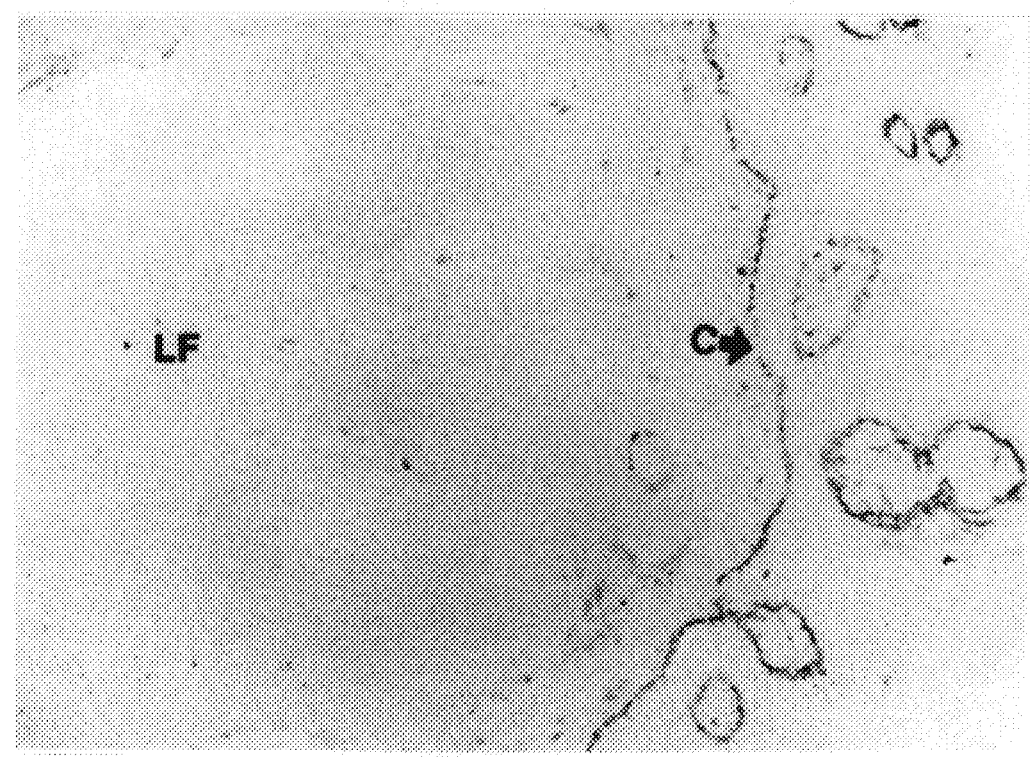
Figure 8M:
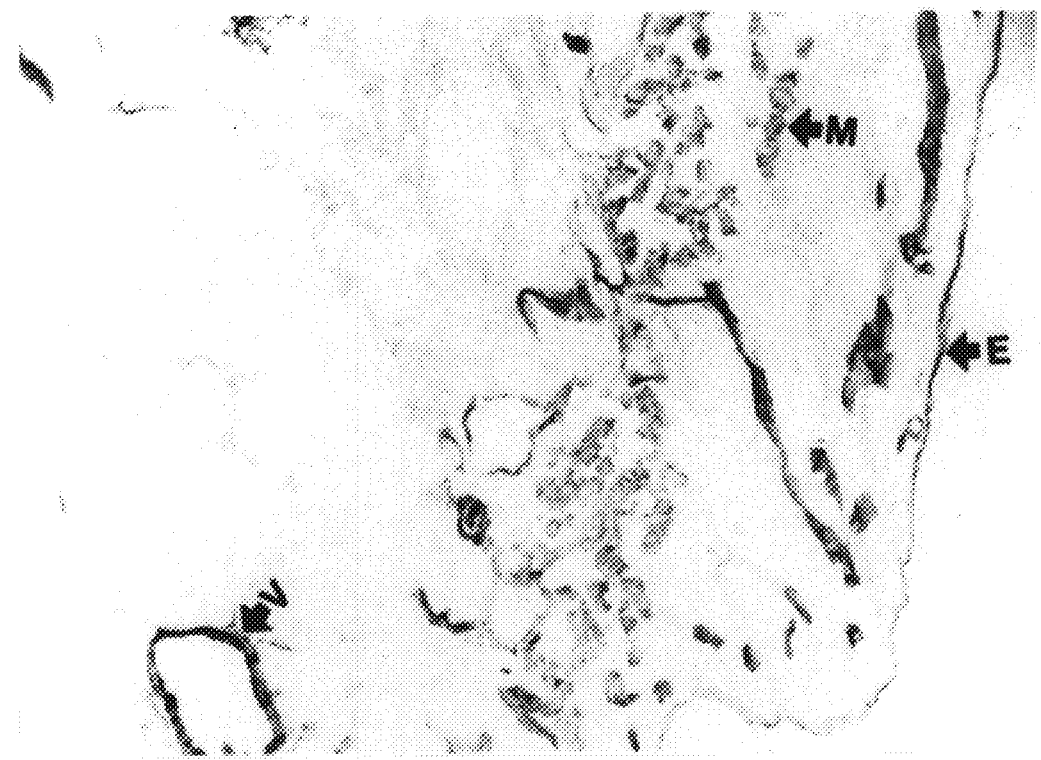
Figure 8N:
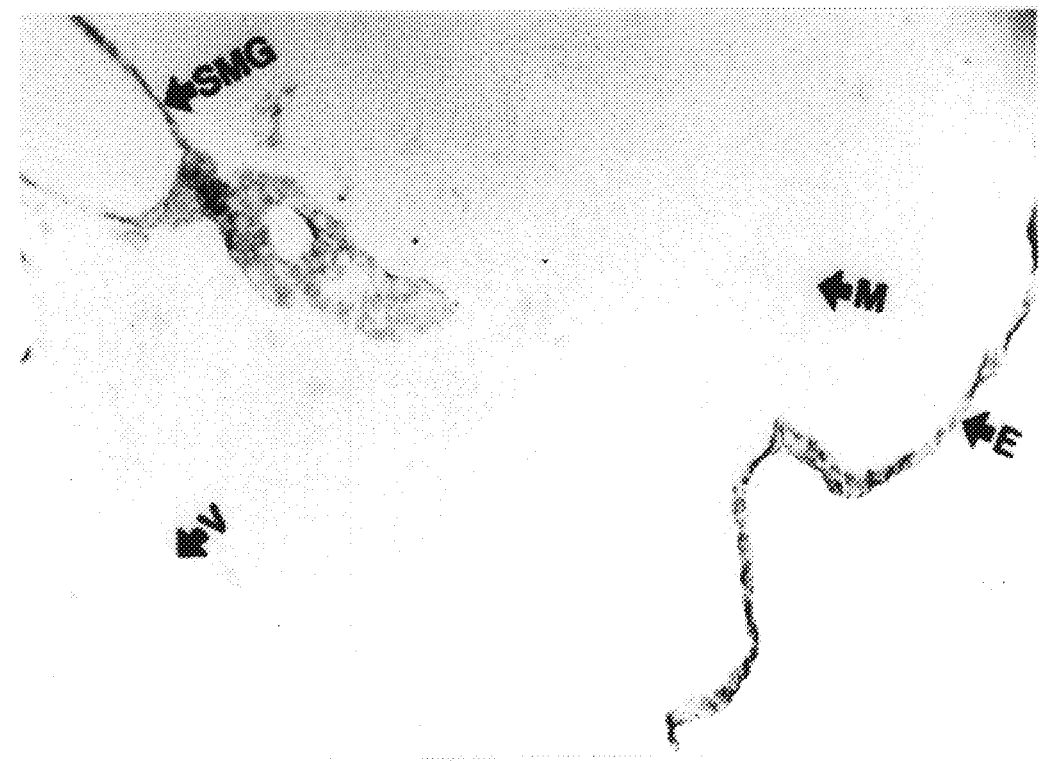
Figure 8O:
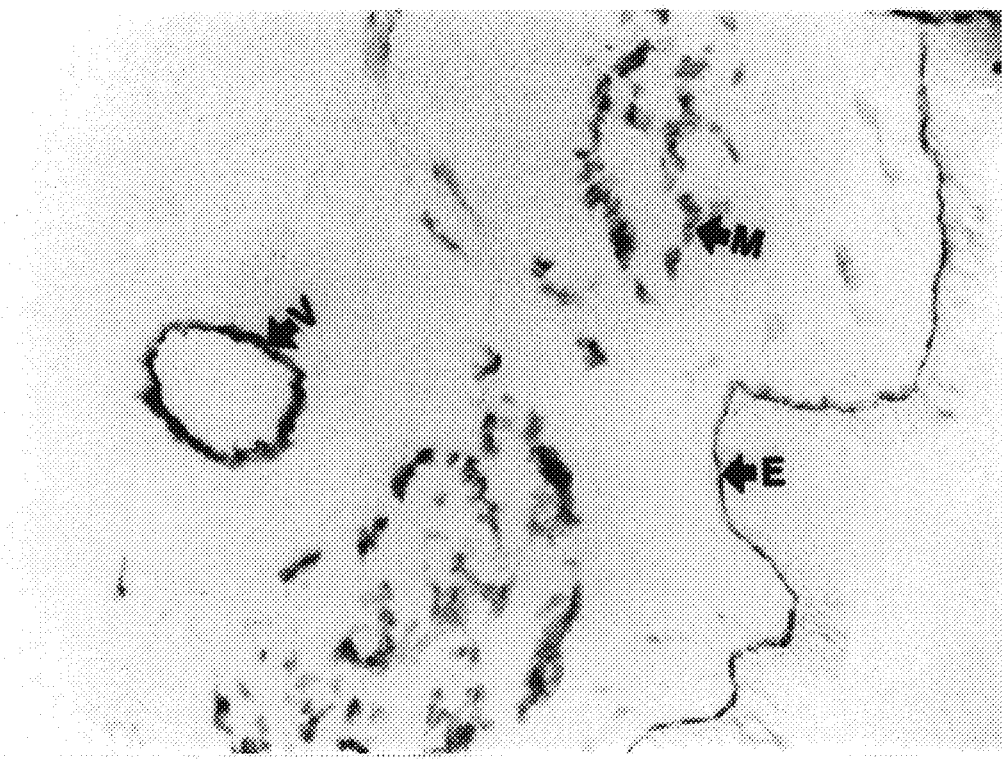
Figure 8P:

FIGS. 8A–P illustrate the localization of epinectin in epithelial basement membranes of skin, tonsil, and lung, and shows epinectin distribution in sweat glands, lymphoid follicle germinal centers, and in submucosal glands, as described on pages 38–41.

FIGS. 9A–F illustrate the ultrastructural localization of epinectin in epithelium, as described on pages 41–42.

5. DETAILED DESCRIPTION OF THE PREFERRED EMBODIMENT

The scientific literature contains several examples wherein the discovery of ubiquitous extracellular proteins (e.g., laminin and fibronectin) led to the subsequent identification and purification of the cellular receptors binding these ligands. In contrast, in the present case the inventor recognized that existing background art which identified laminin as a putative ligand for binding the $\alpha_3\beta_1$ and $\alpha_6\beta_4$ integrin receptors probably described physicochemically minor binding interactions. The inventor had previous observed that the $\alpha_3\beta_1$ and $\alpha_6\beta_4$ integrins were co-distributed in epithelial tissues including human skin; however, the significance of this observation was not readily apparent and the distribution could have been due to both receptors binding to laminin in the tissues. However, in distinction to the teachings in the literature, he reasoned that (a) laminin was not the ligand, and (b) that the two receptors co-distributed because they shared some other (new) extracellular matrix complex as a ligand. With this recognition of the problem, he sought to identify the novel ligand. Because it was not possible to investigate this problem in tissue sections of human biopsy material, he recognized that it would be necessary to select the proper cell type for study in vitro. Since he had previously observed that the two integrin receptors were present together on cells in regions of human skin that contained keratinocytes, fibroblasts, and other specialized epithelial cells, he focused on those regions as a possible source of cells for in vitro study. In considering among these possible different cell types the inventor recognized that human fetal keratinocytes (HFKs) expressed both the $\alpha_3\beta_1$ and $\alpha_6\beta_4$ integrins. Although keratinocytes were recognized by the literature to be a differentiated form of epithelial cell, both with respect to their microscopic appearance and their biosynthetic activities, he reasoned that cultures of these cells might synthesize the novel extracellular matrix ligand, and might be suitable for in vitro study. (In fact, as the detailed description of the invention (appearing below) shows, if he had chosen to study fibroblasts or continuous epithelial cell lines, he would not have succeeded in identifying the ligand which is an embodiment of this invention.) Armed with his recognition of the problem and its possible solution, the inventor set out and succeeded in identifying the novel ligand for the $\alpha_3\beta_1$ and $\alpha_6\beta_4$ integrin receptors. It was a pleasant surprise that the receptors and ligands identified and isolated from keratinocytes in tissue culture were the same as those utilized by the basal (stem) cells in epithelial tissue.

In the research described below, the molecular mechanisms by which epithelial cells establish contact with the basement membrane are elucidated, the cell receptor and its extracellular basement membrane ligand are identified and substantially purified, and the mechanisms are finally unraveled through which growth and differentiation are controlled in the epithelium. The novel ligand which is a subject of the invention is termed "epinectin". Epinectin is a covalently linked glycoprotein complex that mediates epithelial cell attachment to the basement membrane through the $\alpha_3\beta_1$ integrin receptor. Epinectin is present in cell membrane ultrastructural features previously termed focal adhesions. These focal adhesions are located on the basal surface of the cells in areas of contact with the substratum, and they are also involved in cell motility. Epinectin also interacts with the $\alpha_6\beta_4$ receptor which is present in ultrastructural membrane features previously termed hemidesmosomes and stable adhesion complexes. The invention provides an understanding, for the first time, of how these two different ultrastructural features (frozen in time by fixation for electron microscopy) can function in a living cell to mediate adhesion, control of cell growth, and determination of the fate of daughter cells derived from cell division in the basal layer of the epithelium.

The $\alpha_3\beta_1$ integrin receptor which binds the epinectin ligand is one of the most widely expressed of all integrins in tissue, but its physiological ligand has not been identified until now. Novel test cell assays, extracellular matrix compositions, and immunochemical reagents were created which allowed identification for the first time of the epinectin glycoprotein complex in epithelial cells as the physiologically significant ligand for the $\alpha_3\beta_1$ and $\alpha_6\beta_4$ integrin receptors. Only a few epithelial cells in culture (e.g., keratinocytes) express significant quantities of epinectin, and the epinectin glycoprotein complex is of a large molecular size and poor solubility in aqueous solutions. The later properties have undoubtably contributed to the lack of previous recognition of epinectin.

The role of the $\alpha_6\beta_4$ integrin as a receptor for epinectin (i.e., in stable adhesion complexes) is less impressive than the adhesion mediated by the $\alpha_3\beta_1$ integrin receptor but is potentially more significant. The findings described below indicate that the $\alpha_6\beta_4$ integrin receptor is involved in cellular adhesion to basement membranes, and it may also localize the focal adhesions in a pattern which encircles the regions of the stable anchoring contracts. This process of encirclement, as well as the localization of the $\alpha_6\beta_4$ receptor in cell-cell adhesion sites, determines the fate of the daughter cells formed by division in the basal (stem) cell layer of the epithelium.

Migration of epithelial cells is an important aspect of at least wound healing, inflammation, and tumor metastasis. The focal adhesions containing the $\alpha_3\beta_1$ integrin receptor are involved in cell movement, and the stable anchoring contacts containing the $\alpha_6\beta_4$ integrin receptor are involved in stopping cell movement. Epinectin binds to both $\alpha_3\beta_1$ and $\alpha_6\beta_4$. This inventive recognition, pursuant to the present disclosure, allows one skilled in the art to identify specific binding partners to epinectin (as disclosed in greater detail, below), and provides for the first time compositions which can modify movement and adhesion of cells of epithelial origin. The invention also provides, for the first time, an understanding at the molecular level of how polarized self-regulated growth and differentiation are achieved in epithelial tissues, namely, through the binding of the transmembrane integrin receptors in the plasma membrane to extracellular ligand in the epinectin complex, and through intracellular signalling accomplished by the 36±15 kd epinectin glycoprotein. These events occur at discrete plasma membrane sites, namely in the stable anchoring contacts, and a second cytoplasmic polypeptide was also discovered to be a recognized SACs protein termed Bullous pemphigoid antigen. Armed with the new information and understanding provided in the present disclosure, one skilled in the art is able to recognize how malignant carcinoma cells may arise, namely through loss of the control mechanisms provided by the epinectin complex, and how it is possible to consider reestablishing these normal control mechanisms in carcinoma cells, namely by using the understanding provided by the invention to select for epinectin derivatives and other pharmaceutical agents that induce the cells to correct their defect in epinectin regulation.

These conclusions are based on the following findings, and on reinterpretation of previous reports in light of the new insights gained from the present invention, namely: (i) Purified epinectin induced cell adhesion and localization of the $\alpha_3\beta_1$ integrin receptor in focal adhesions better than laminin, fibronectin, or collagen. Further, cell adhesion to epinectin was specifically inhibited with monoclonal antibodies to the $\alpha_3\beta_1$ integrin receptor. (ii) Epinectin was the major component of the extracellular matrix synthesized by human foreskin keratinocytes. In cultures of stationary keratinocytes, epinectin deposited and co-distributed with the transmembrane $\alpha_6\beta_4$ integrin receptor and with cytoplasmic Bullous pemphigoid antigens which are recognized components of hemidesmosome-like stable adhesion complexes. All three of these components in the stable adhesion complexes were resistant to sequential extraction with detergent, 2M Urea/1M NaCl, and 8M Urea. In contrast, the $\beta$1-containing integrin receptors in the focal adhesions were not stable to this extraction. The $\alpha\lambda_3\beta_1$ integrin-containing focal adhesions were observed to form rings around the periphery of the $\alpha_6\beta_4$ integrin containing stable anchoring contacts. (iii) In tissue, epinectin localized in most epithelial basement membranes, but not in the basement membranes of muscle, or endothelium. At the ultrastructural level, epinectin localized to the Lamina lucida of the epidermal/dermal basement membrane of skin. Consistently, epinectin localized with the $\alpha_3\beta_1$ integrin receptors in the basal plasma membrane, as well as with the $\beta_4$ integrin-containing hemidesmosomes of basal (stem) cells.

The HFK epinectin glycoprotein complex includes at least four covalently linked disulfide-bonded glycoproteins having apparent molecular sizes of 200 kd, 170 kd, 145 kd, and 135 kd, and an associated intracellular cytoplasmic glycoprotein of 36 kd. The individual epinectin glycoproteins are visible following reduction and SDS-PAGE (under reducing conditions). Epinectin glycoprotein complexes have the ability to modify cellular adhesion to substrata. Epinectin antigens are located on the basal surfaces of basal (stem) cells in epithelia at limited points of cellular contact with basement membranes. Embodiments of the invention relate to epinectin glycoprotein compositions for modifying adhesion of cells to substrata and for achieving polarized and self-regulated growth and differentiation in cells of epithelial origin. Other embodiments relate to antibodies to the epinectin glycoprotein complex for modifying cellular adhesion to substrata and for identifying epinectin antigens in biological fluids, as well as epinectin antigens for identifying antibodies in patient samples. Embodiments of the invention provide compositions and test methods for identifying diseased epithelial cells, and for distinguishing at least between the epithelial abnormalities in such autoimmune dermatological diseases as Bullous pemphigoid, Cicatrical pemphigoid, and Epidemolysis bullosa acquisita.

These and other aspects of the invention are described below.

5.1 Definition of Terms

The following terms used herein are meant to mean as follows: namely,

"epinectin glycoprotein" means a constituent glycoprotein of the epinectin complex;

"substantially-pure" means of a purity sufficient that more than 70% of the polypeptides in the preparation can be determined by SDS-PAGE and protein staining to be the composition so specified;

"covalently linked" means polypeptides chemically bonded to one another, as through for example (but not limited to) disulfide-bonds, thiol-ester bonds, ester bonds, amide bonds, or the like;

"capable of binding" means physical interaction between two materials, such as between a specific binding partner and a ligand, where the interaction is sufficiently strong to permit measurement of a chemical association (or dissociation) constant (i.e., Ka or Kd);

"substratum" means an insoluble material upon which cells may be deposited by gravity;

"non-adhesive substratum" means a substratum to which fewer than 20% of the cells will bind in 24 hours at 37° C. and from which 80% of the cells can be removed by washing with medium, e.g., such a substratum is provided by microbiological grade polystyrene plastic petri dishes;

"epithelial cells" means, in this disclosure, the cells originating through mitosis in epithelial tissues which cover the free surfaces of the body and line the body cavities and ducts, as well as cells of epithelial origin such as malignant carcinoma cells (further examples of epithelial cells as they are commercially available are provided in Table I, below, as listed in the "Catalogue of Cell Lines and Hybridomas", 6th Edition, 1988, the American Type Culture Collection, Rockville, Md.;

"modulate" means an increase or decrease to a measurable extent in the specified effect;

"adhesion assay" means an assay conducted with test cells, such as HT1080 in Example 6 below, to measure adhesion of cells to a protein-coated "non-adhesive" substratum under defined test conditions of tissue culture;

"differentiation" means a staged process, e.g., in development, through which a cell progressively acquires distinguishably new phenotypic attributes;

"confluent cell culture" means a culture in which more than 85% of the cells are observed microscopically to be in physical contact with their neighboring cell;

"resistant to digestion" means that no substantial change in physical properties is observed following incubation of the polypeptide with an enzyme for a substantial period of time;

"co-migrate" is meant to mean substantially the same electrophoretic migration when two polypeptides are either run together in the same lane of an SDS-PAGE gel, or alternatively, when they are run side-by-side in adjacent lanes;

"substantial reactivity", e.g., with antibodies, is meant to mean that one skilled in the art would be able to determine a level of reactivity which he would determine to be statistically significant;

"molecular size" is meant to mean the apparent molecular radius of the polypeptide as it is observed under denaturing conditions in SDS-PAGE, and as recorded in kilodaltons (kd ±) of mass as determined by comparison with other polypeptides of known molecular mass.

TABLE I

Examples of Commercially-Available Human Epithelial Cells

| Tissue | Name/ATCC No. | Description |
| --- | --- | --- |
| Endometrium | RL95-2/CRL1671 | Adenosquamous carcinoma |
| Skin | WM-115/CRL1675 | epitheloid melanoma |
|  | WS-1/CRL1502 | fetal skin |
| Pancreas | AsPC-1/CRL1682 | adenocarcinoma |
|  | PANC-1/CRL1469 | epitheloid carcinoma |
| Stomach | AGS/CRL1739 | adenocarcinoma |
| Bladder | UM-UC-3/CRL1749 | bladder carcinoma |
|  | HT-1197/CRL1473 | bladder carcinoma |
| Colon | CCD841CoN/CRL1790 | fetal epithelial-like |
|  | NCI-H548/CCL249 | adenocarcinoma |
| Tongue | SCC-9/CRL1629 | squamous cell carcinoma |
| Kidney | ACHN/CRL1611 | adenocarcinoma |
| Cervix | C-4I/CRL1595 | carcinoma |
|  | CaSki/CRL1550 | epidermoid carcinoma |

TABLE I-continued

Examples of Commercially-Available Human Epithelial Cells

| Tissue | Name/ATCC No. | Description |
| --- | --- | --- |
| Ovary | PA-1/CRL1572 | teratocarcinoma |
| Epidermis | A-431/CRL1555 | epidermoid carcinoma |
| Breast | ZR-75-1/CRL1500 | mammary carcinoma |
|  | MCF-7/HTB22 | adenocarcinoma |
| Pharynx | Detroit 562/CCL138 | carcinoma |
| Adrenal cortex | SW-13/CCL105 | adenocarcinoma |
| Lung | WI-38/CCL75 | fetal diploid |

5.2 Keratinocyte Extracellular Matrix and Immunoprecipitation of Epinectin: The Major Glycoprotein Complex in Adhesive HFK-ECM For this study, the extracellular matrix synthesized and secreted by HFKs shall be referred to as HFK-ECM and that synthesized and secreted by HFFs as HFF-ECM. Endogenous HFK-ECM is that which is intracellular or plasma membrane associated. HFK-ECM secreted into the conditioned culture medium during the time course of an assay, or that which can be purified from culture dishes or glass cover slips (after the removal and/or extraction of the HFKs, as by the three-step extraction procedure detailed below), is referred to as exogenous HFK-ECM.

Figure 1:
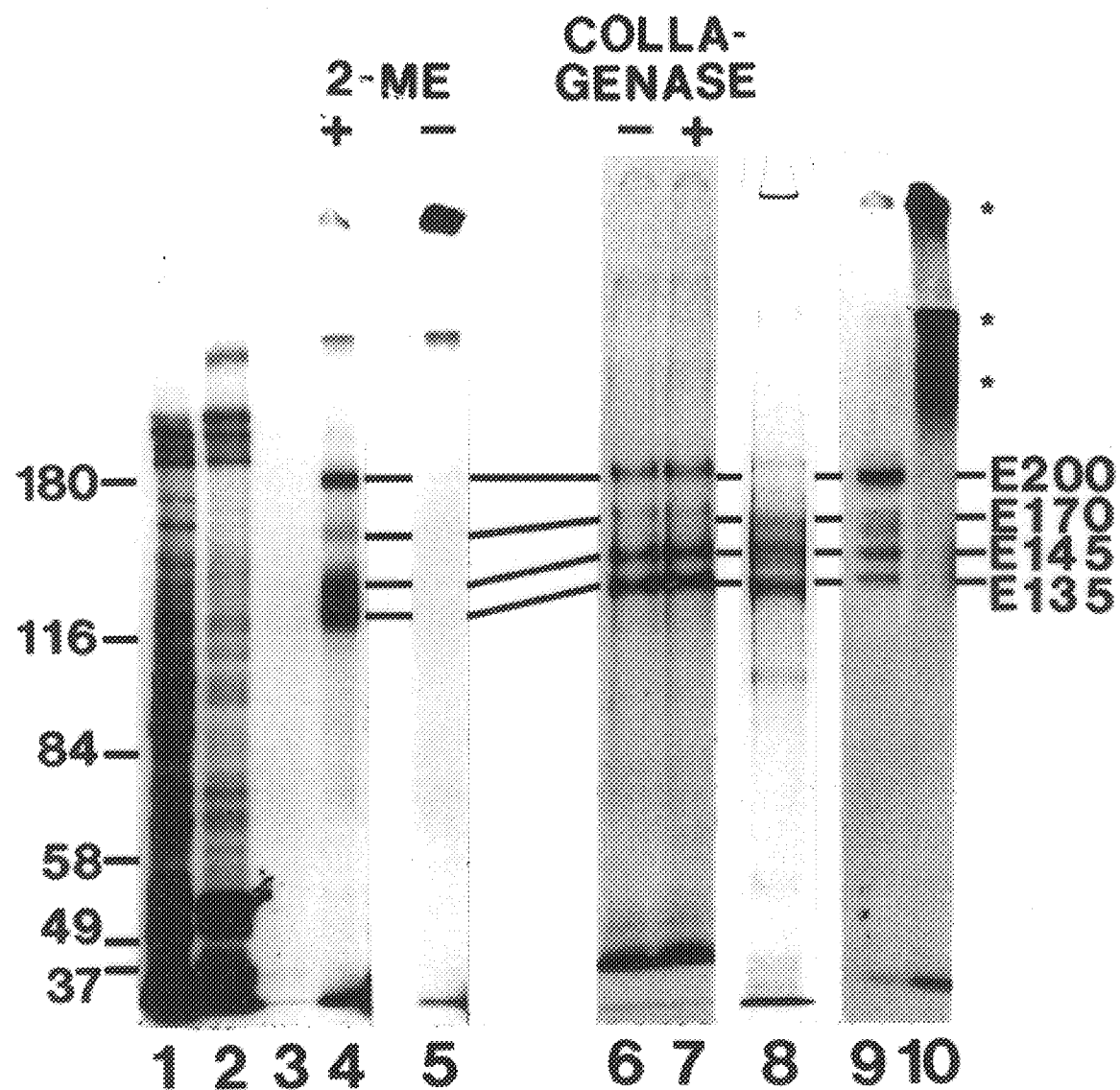
FIG. 1 shows glycoproteins extracted as the epinectin glycoprotein complex from extracellular matrix, as described on pages 24–27.
Figure 3:
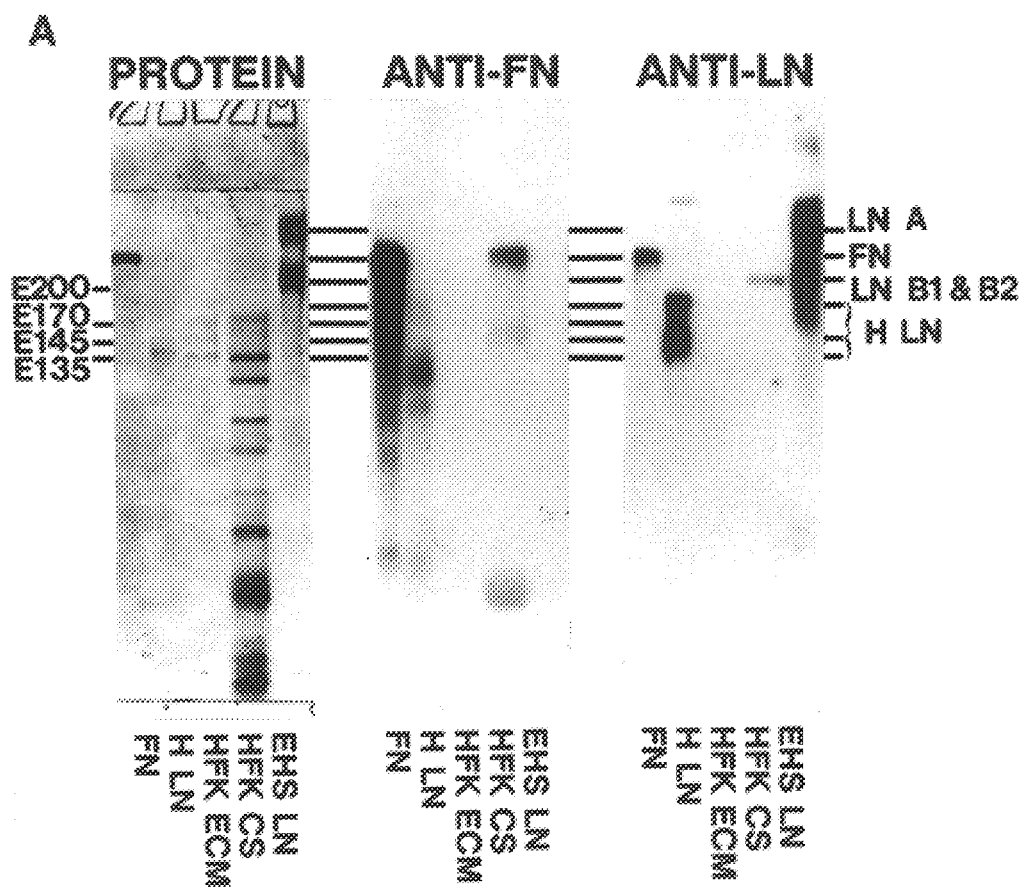
FIG. 3 shows that the purified HFK-ECM does not contain fibronectin or laminin, as described on pages 28–30.

To identify a physiologically significant ligand for the $\alpha_3\beta_1$ and/or $\alpha_6\beta_4$ integrin receptors in epithelial cells, we first examined the composition of the ECM produced by HFK. Radiolabeled HFK-ECM and HFK were prepared by incubating HFK in culture dishes for 15 hours in KGM containing $^{35}$S-methionine, $^3$H-glucosamine, or $^{35}SO_4^{-2}$, and 1 mg/ml HD-BSA (Sigma) as a carrier protein. Radiolabeled HFKs were sequentially extracted in a sequential three-step extraction procedure, as described previously (Wayner and Carter, 1987): namely, (1) with 1% (w/v) Triton X-100 (Sigma; to solubilize membranes and cytoplasmic constituents) and 2 mM N-ethylmaleimide (Sigma, to prevent intramolecular cross-linking); (2) with a solution containing 2M Urea and 1M NaCl (to remove nuclear and cytoskeletal components); and (3) with 8M Urea (to solubilize residual cellular components). All extraction buffers contained 1 mM phenylmethyl sulfonyl fluoride (PMSF; Sigma Chemical Co., St. Louis, Mo.) and a protease inhibitor and 2 mM N-ethylmaleimide (Sigma) as an inhibitor of intramolecular cross-linking. The constituent radiolabeled glycoproteins were separated by SDS-PAGE (12) and visualized by fluorography. The results of the sequential extraction procedure are presented in FIG. 1 where lanes 1–3 show the glycoproteins extracted in the steps 1, 2, and 3 (above), respectively. To examine the nature of the 8M Urea-insoluble HFK-ECM glycoproteins remaining on culture dishes after the extraction step 3, 0.5% (w/v) SDS was added to the culture dishes, and glycoproteins were physically dissociated by mechanical scraping with a rubber policeman. The glycoproteins obtained in this manner did not enter an 8% SDS-PAGE gel (FIG. 1, lane 5) unless they were reduced on SDS-PAGE under reducing conditions (i.e., with 2-mercaptoethanol; 2ME) and visualized by fluorography. They consisted essentially of at least five major glycoproteins visualized by protein staining with Coomassie brilliant blue (FIG. 1; lane 8) or following biosynthetically radiolabeled with $^{35}$S-methionine (FIG. 1, lane 4), or 3H-glucosamine (FIG. 1, lane 9); these glycoproteins having apparent Mr of 200 kDa, 170 kDa, 145 kDa, 135 kDa, and 36 kDa (FIG. 1, lane 9). (Migration of molecular mass standards are indicated in the left margin of FIG. 1 (i.e., 180, 116, 84, 58, 49, and 37 kd).) The HFK-ECM glycoproteins detected with protein stain showed slightly decreased amounts of the 200 kd glycoprotein (FIG. 1, lane 8). The five major glycoproteins were designated E200, E170, E145, E135, and E36, based on relative molecular mass under reducing conditions on 8% SDS-PAGE. The E170 band was inconsistently resolved into two bands (FIG. 1, lane 9). Under non-reducing conditions the five glycoproteins did not enter the polyacrylamide gel (FIG. 1, lane 5), indicating that they were subunits of one or more high molecular mass complexes, cross-linked by intermolecular disulfide bonds. Although the glycoprotein subunits were not labeled with $^{35}SO_4^{-2}$, three additional sulfate-labeled components, probably glycosaminoglycan or proteoglycan, were also present in the exogenous HFK-ECM (FIG. 1, lane 10, marked with *). In control experiments, metabolic labeling for different times failed to detect any precursor product relationship among the five glycoprotein subunits of the complex. Comparison of the molecular masses of the five glycoprotein subunits in the complex to known basement membrane components failed to detect any obvious relationships. To evaluate further any possible relationship between the exogenous HFK-ECM glycoproteins and the collagens, non-reduced and reduced (2-mercaptoethanol; Sigma) $^{35}$S-methionine biosynthetically radiolabeled HFK-ECM was treated at 37° C. for 18 hours with 100 units/ml collagenase (Advanced Biofactures, Form III) under conditions which degrade collagen standards, as described previously (98). The collagenase-digested radiolabeled HFK-ECM was extracted using the same three-step extraction procedure described above, and the glycoproteins were separated using SDS-PAGE and visualized by fluorography. None of the five major glycoprotein components in HSK-ECM was digested with collagenase either when non-reduced (FIG. 1, lanes 6 and 7) or reduced prior to digestion, indicating that they were not collagens. In addition, the HFK-ECM glycoproteins (FIG. 3, HFK-ECM) did not co-migrate on 8% SDS-PAGE with purified protein standards of EHS sarcoma laminin (FIG. 3, EHS-LN; LN A; LN B1 and B2), fibronectin (FN); when visualized by staining for protein with Coomassie blue (FIG. 3, PROTEIN), entactin, or tenascin, but E170 did co-migrate with pepsinized human placental laminin (FIG. 3, compare HFK-ECM to H LN). In contrast (and as expected), proteins in conditioned medium from HFK cells (HFK CS, FIG. 3) contained a multiplicity of proteins, some of which co-migrated with the protein standards (FIG. 3, HFK CS). To further evaluate any possible relationship between fibronectin (or laminin) and the components in exogenous HFK-ECM, three types of experiments were conducted. First, the glycoproteins in exogenous HFK-ECM were separated on SDS-PAGE, blotted onto nitrocellulose as described previously (98) and tested for their immunoblot reactivity with rabbit antibodies directed toward laminin (Anti-LN; FIG. 3) or fibronectin (Anti-FN; FIG. 3). Anti-FN bound to antigens in HFK-conditioned medium (HFK CS) and in purified fibronectin (FN) but not in human placental laminin (H LN), sarcoma EHS laminin (EHS LN) or HFK-ECM; anti-LN bound to antigens in HFK-CS, H LN, and EHS-LN but not in FN or HFK-ECM (FIG. 3). In summary, immunoblotting of HFK-ECM with anti-laminin or anti-fibronectin (FIG. 3, Panel "Anti-LN and Anti-FN") failed to detect any relationship between these known extracellular matrix glycoproteins and the glycoproteins in HFK-ECM. Second, polyvalent antibodies to laminin or fibronectin were also used to prepare an immunoprecipitate of exogenous HFK-ECM. Immunoprecipitation with antibodies against laminin, fibronectin, tenascin, entactin, or Bullous pemphigoid antigen (BPA) failed to detect any immunological cross-reaction among those known BM proteins and the five major glycoprotein subunits of the HFK-ECM. Third, HFK-ECM was scraped from the substratum and used to immunize rabbits to induce antiserum. The resultant antisera did not react with laminin or fibronectin, but did react with E170, E145, and E135 in the HFK-ECM.

In order to further characterize the HFK-ECM, we prepared monoclonal antibodies (MAbs) against the HFK-ECM glycoprotein complex using HFKs as an immunogen.

5.3 Binding Partners as Exemplified by Monoclonal Antibody to HFK-ECM

Binding partners as exemplified by MAbs to HFK-ECM were produced by the methods of Oi and Herzenberg (99) and Taggart and Samloff (100) as described (59). Spleen cells from RBF/Dn mice immunized with cultured HFKs were fused with NS-1/FOX-NY myeloma cells. Viable heterokaryons were selected in RPMI 1640 medium supplemented with adenine/aminopterine/thymidine.

Figure 2:
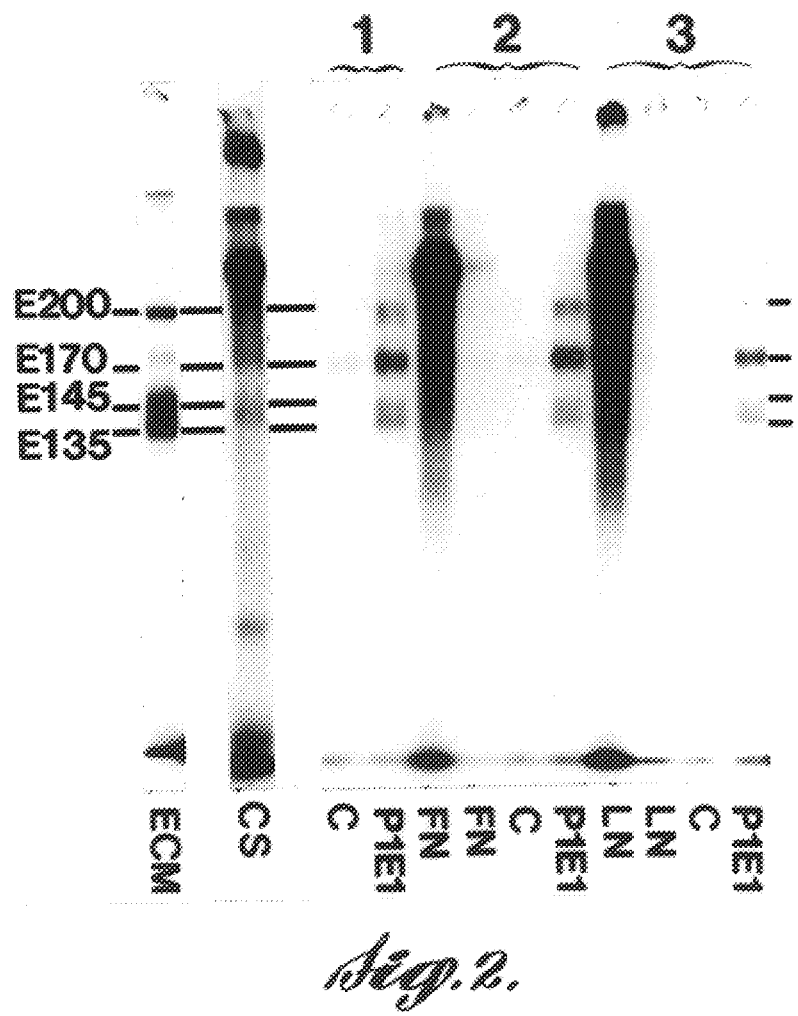
FIG. 2 depicts glycoproteins in the epinectin glycoprotein complex which are not related to known basement membrane components, as described on pages 27–28.

Hybridomas P1E1 and P1H8 producing antibody specifically directed to HFK-ECM were selected using immunofluorescence microscopy and HFK-ECM or HFF-ECM on glass cover slips. We selected MAbs P1E1 and P1H8 that reacted with HFK-ECM but not HFF-ECM produced by the dermal fibroblasts. P1E1 and P1H8 were cloned by limiting dilution. P1E1 and P1H8 (with rabbit anti-mouse IgG) immunoprecipitated five relatively minor disulfide-bonded subunits from the conditioned culture medium of $^{35}$S-methionine-labeled HFKs. The results presented in FIG. 2 show examples of three (1, 2, 3) such immunoprecipitation experiments conducted with P1E1 in which HFK cells were metabolically radiolabeled with $^{35}$S-methionine, as described above, and antigens in the conditioned medium (FIG. 2; CS) and HFK-ECM (FIG. 3; ECM) were immunoprecipitated. The five subunits of the P1E1 antigen(s) co-migrated with the five major glycoprotein subunits of the exogenous HFK-ECM (FIG. 2, compare ECM in the far left lane of the figure with P1E1, experiment 1). The E170 subunit in the precipitated P1E1 antigen was increased relative to the other subunits in all three experiments, suggesting that E170 contained the epitope recognized by the P1E1 MAb. In a similar manner, the E36 component of glycoprotein complex was increased in the immunoprecipitate prepared in this manner between radiolabeled HFK-CS and P1H8, suggesting that E36 may contain the antigenic epitope for P1H8. The possibility that the glycoprotein complex recognized by P1E1 may contain antigens previously identified was once more evaluated, this time utilizing immunoprecipitation techniques. Preclearing of HFK conditioned culture medium (FIG. 2; CS) by immunoprecipitation with polyvalent anti-fibronectin (FIG. 2, experiment 2; FN), polyvalent anti-entactin, or mouse monoclonal anti-tenascin prior to precipitation with P1E1 had no effect on subsequent precipitation of P1E1 antigens. However, preclearing (i.e., immunoprecipitating) with polyvalent anti-laminin (FIG. 2; experiment 3, LN) removed E200 and 50% of the other subunits from the P1E1 precipitate. Since none of the glycoproteins (i.e., E200, E170, E145, E135, or E36) reacted with anti-laminin antibodies by Western immunoblotting after SDS-PAGE (FIG. 2), we conclude that: (a) E200 in the complex is not laminin; and (b) glycoprotein complex may be associated with laminin so that it forms a complex that can be precipitated with the anti-laminin antibody. This type of interaction of laminin has not been reported previously, and its composition differs significantly from interactions of laminin with other glycoproteins.

In summary, the P1E1 and P1H8 antigens correspond in molecular sizes to the glycoproteins in exogenous HFK-ECM, which consists of at least five subunits, namely, E200, E170, E145, E135, and E36, which are visualized on SDS-PAGE after reduction, and that are distinct from any previously identified adhesion ligand(s) present in basement membranes or extracellular matrix. The complex recognized by P1E1 and P1H8 is the major component of exogenous HFK-ECM and also a minor component in HFK-conditioned culture medium. Based on the unique characteristics of this complex, and in order to simplify the following discussion, we shall henceforth refer to the covalently linked glycoprotein complex as "epinectin."

5.4 Epinectin Distribution in Motile and Non-Motile HFKs

The organization of epinectin deposited in HFK-ECM was examined by immunofluorescence microscopy, using MAb P1E1 and P1H8 and antibodies directed toward other extracellular matrix adhesive ligands. It was found that P1H8 stained only cells which were permeabilized to allow staining of cytoplasmic proteins, indicating that the P1H8 antigen was a cytoplasmic constituent of cells expressing $\alpha_3\beta_1$ integrin receptors. Subsequent studies, detailed below, utilized only the P1E1 MAb.

HFKs were grown for 24 hours on glass cover slips coated with either fibronectin (FIGS. 4A and B) or BSA (FIGS. 4C–K), as described above (see "Cellular Adhesion to Extracellular Matrix Adhesive Ligand-Coated Substrates"). Glass cover slips and cells were then incubated with mouse or rat MAbs or rabbit polyclonal primary antibodies diluted in 1% heat HD-BSA overnight as previously described (21). The cover slips were washed with PBS; incubated with dilutions of affinity-purified, species-specific, FITC-conjugated goat anti-mouse/rat IgG or Rhodamine-conjugated goat anti-rabbit IgG secondary antibodies (respectively) for 1 hour, washed with PBS, and fixed with 2% formaldehyde prior to immunofluorescence microscopy. The organization of epinectin was dependent on the ligand to which the HFKs were attached. When HFKs attached to fibronectin (FIG. 4A), collagen, or laminin, the cells migrated over the ligand surface leaving trails of epinectin.

Figure 4A:
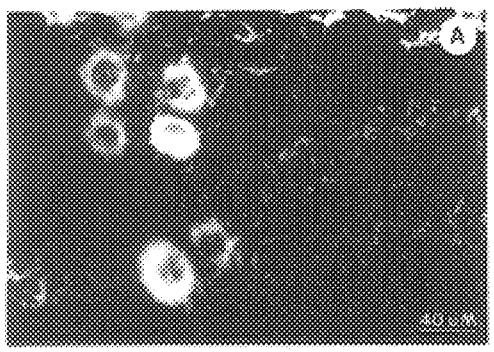
Figure 4B:
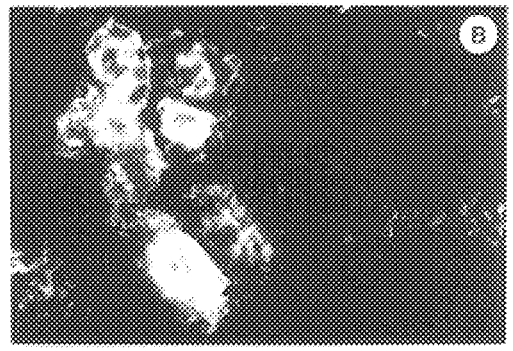
Figure 4C:
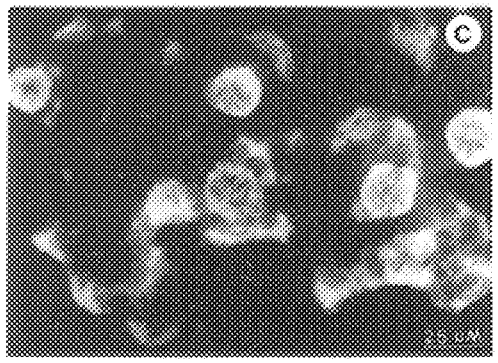
Figure 4D:
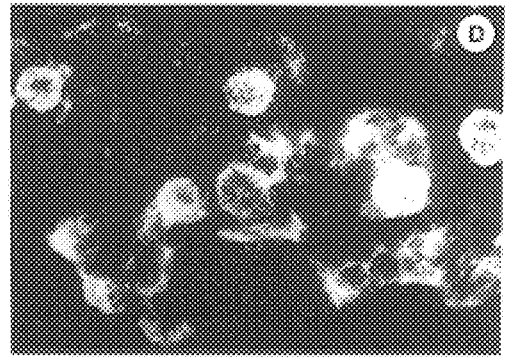
Figure 4E:
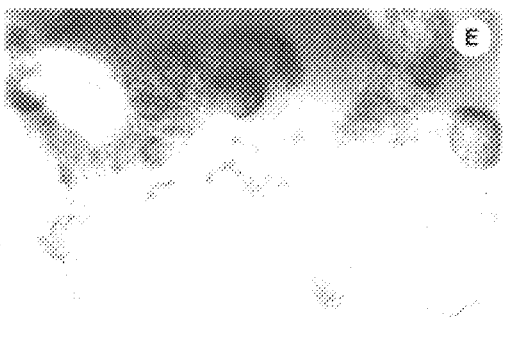
Figure 4F:
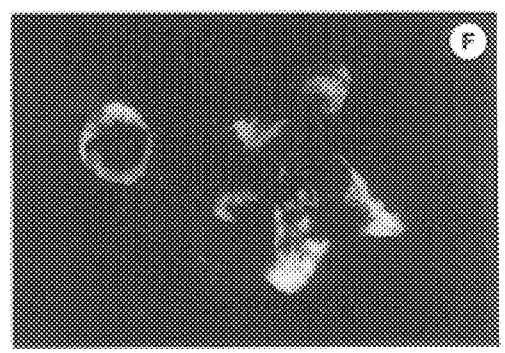
Figure 4G:
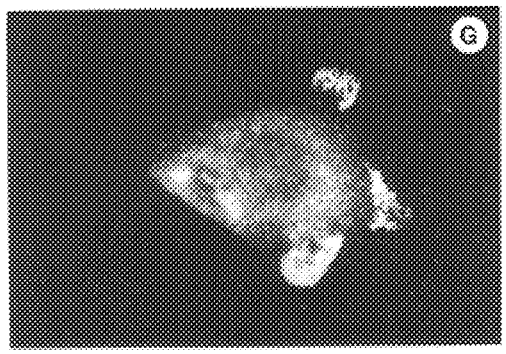
Figure 4H:
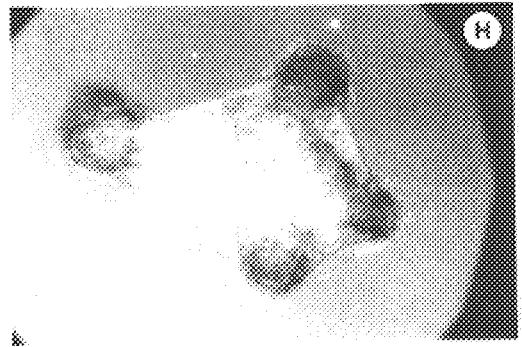
Figure 4I:
Figure 4J:
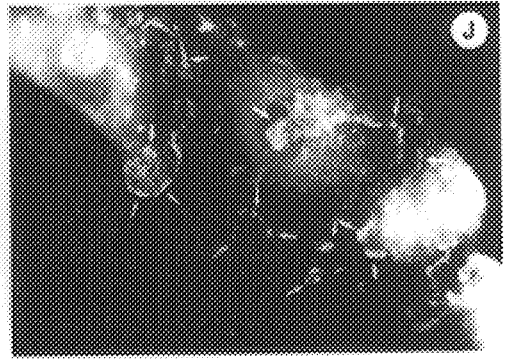
Figure 4K:
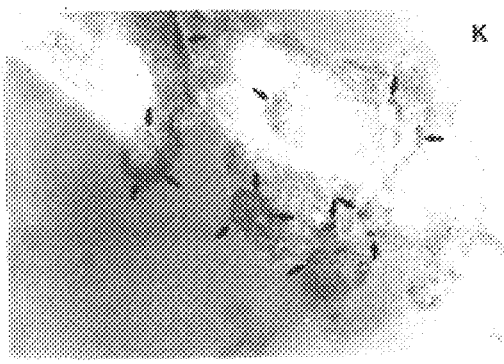

To investigate whether the $\alpha_3$- and $\alpha_6$-containing integrins (i.e., $\alpha_3\beta_1$ and $\alpha_6\beta_4$) were associated with the epinectin glycoprotein complex on the cell surface, tests were conducted simultaneously to visualize the receptor and its putative ligand on HFKs using a double immunofluorescence technique. Epinectin (P1E1, FIGS. 4A, 4C, 4F, 4I) was localized relative to $\alpha_6$ (FIGS. 4B, 4D; GoH3), BPA (FIG. 4G) and $\alpha_3\beta_1$ (FIG. 4J; P1F2). SACs and FAs were identified in each field by interference reflection microscopy (FIGS. 4E, 4H, 4K). Arrows in panels I, J, K identify $\alpha_3\beta_1$ in FAs in relation to epinectin in SACs. HFKs were incubated with: (1) mouse MAb anti-$\alpha_6$ (GoH3); followed by (2) incubation with rhodamine-conjugated goat-antimouse IgG and IgM; after which the cells were fixed and reacted with (3) biotinylated with mouse P1E1-MAb; followed by (4) fluorescein Avidin. In migrating HFK cells, $\alpha_6\beta_4$ was expressed on the apical surface of the cells and at the trailing edge. Small quantities of $\alpha_6\beta_4$ co-distributed with the epinectin antigen in the trails of these cells (FIG. 4B).

As described (20), when HFKs are grown on BSA-coated surfaces, the cells migrate less and form hemidesmosome-like stable anchoring contacts (SACs) on their basal surface. In the present study, by immunofluorescence microscopy, all the SACs on the basal surface of the stationary HFK cells contained $\alpha_6\beta_4$ and most contained BPA. As seen in FIG. 4C, HFKs grown on BSA deposited epinectin antigen on the substrata in "ring-like structures" characteristic of SACs.

The distribution of epinectin antigen (P1E1; FIGS. 4A, 4C, 4F) in relation to $\alpha_6$ (GoH3; FIGS. 4B, 4D), and BPA (FIG. 4G) was most strikingly similar in the "ring structures." To further distinguish SACs from focal adhesions, interference reflection microscopy (IRM) was performed basically as described (Izzard and Lochner, 1976) and was used to identify focal adhesions (FAs) in the same field as the two color immunofluorescence which identified the SACs. FAs were also localized by the antibody exclusion technique (101). Epinectin (identified by P1E1) in $\alpha_6\beta_4$/BPA-SACs corresponded to contact sites with the adhesion surface as determined by interference reflection microscopy (FIGS. 4E, 4H). The co-localization and similar stabilities indicated that the deposits of epinectin antigen were at adhesion sites linked to $\alpha_6\beta_4$/BPA-SACs.

Figure 5A:
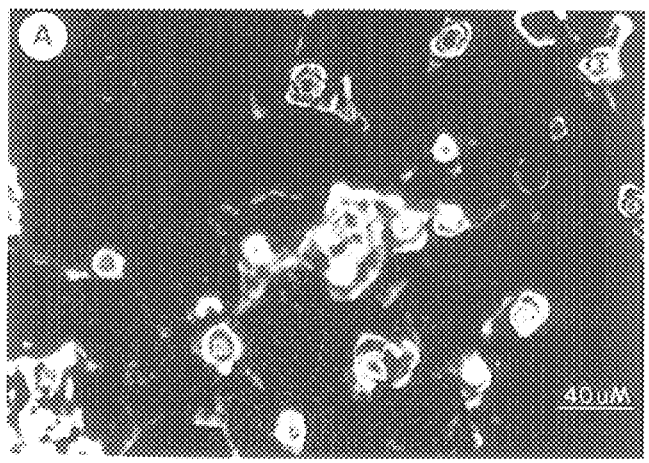
Figure 5B:
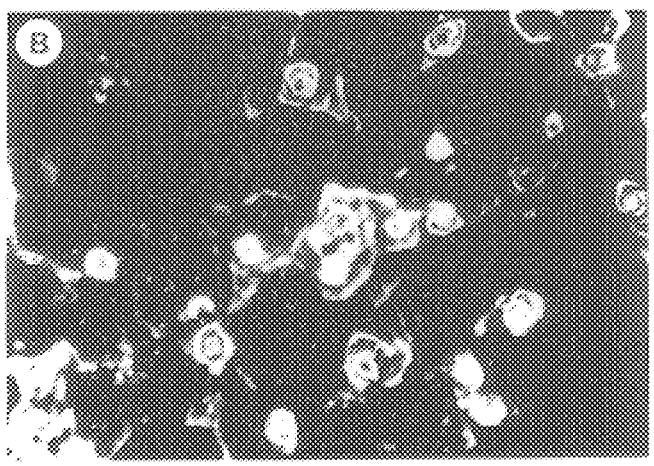
Figure 5C:
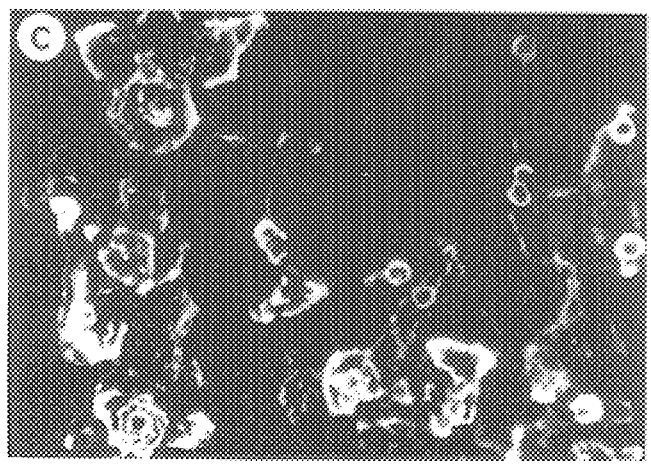
Figure 5D:
Figure 5E:
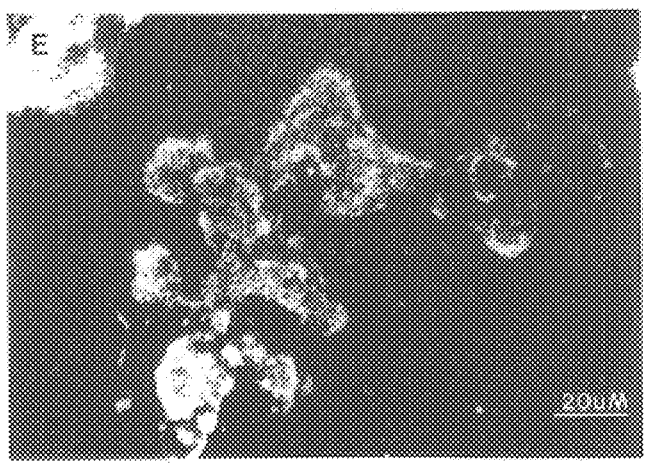
Figure 5F:
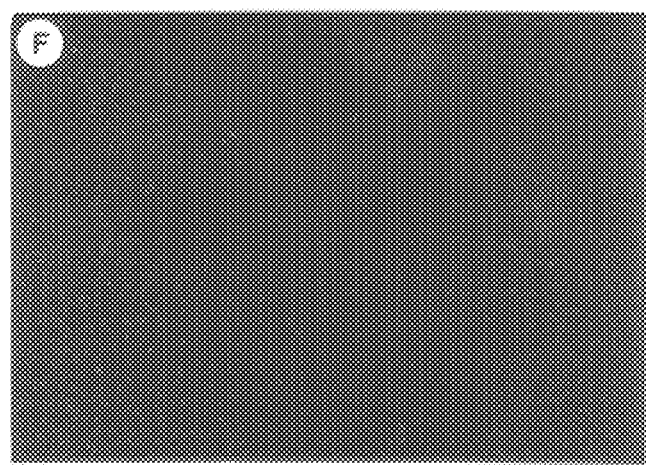

As an additional test for the localization of epinectin glycoprotein complex in SACs, since we had previously observed that $\alpha_6\beta_4$ and BPA in SACs are extraordinarily stable and are resistant to sequential extraction with 1% Triton X-100 detergent and 2M urea/1M NaCl, while the β1-containing integrins in focal adhesions are soluble under these extraction conditions (20), we therefore next examined the distribution of epinectin, $\alpha_6\beta_4$, BPA, and $\alpha_3\beta_1$ in HFKs SACs extracted in this manner. HFKs were grown for 24 hours on surfaces coated with BSA, then extracted with 1% Triton X-100 detergent followed by 2M urea containing 1M NaCl. The adherent cell residue containing SACs was stained with anti-epinectin (P1E1, FIGS. 5A, 5C, 5E), anti-$\alpha_6(\beta_4)$ (GoH3, FIG. 5B), anti-BPA (FIG. 5D), and anti-$\alpha_3\beta_1$ (FIG. 5F; P1F2). Consistently, we observed that epinectin antigen was present in sequentially extracted HFK SACs (P1E1; FIGS. 5A, 5C, 5E). In these studies $\alpha_6$, $\alpha_3\beta_1$, epinectin, or BPA antigen was visualized using a double immunofluorescence technique. Epinectin antigen co-distributed with the $\alpha_6$ (GoH3; FIG. 5B), and BPA (FIG. 5D) in the extracted HSK-ECM. The co-distribution of epinectin antigen with $\alpha_6\beta_4$ and BPA in both non-extracted and sequentially extracted HFKs (Triton X-100, 2M urea/1M NaCl, above) indicated a stable linkage between the cytoplasmic intermediate filament BPA, the intrinsic membrane $\alpha_6\beta_4$ integrin and the extracellular epinectin glycoprotein complex ligand, as major constituents of hemidesmosome-like SACs.

5.5 Epinectin Complex is a Ligand for $\alpha_3$ $\beta_1$-FAs

We have previously reported that $\alpha_3\beta_1$ in HFK-ECM is localized into FAs in proximity to, but excluded from, $\alpha_6\beta_4$/BPA-SACs (20, 21). HFKs that deposited epinectin in SACs, usually localized $\alpha_3\beta_1$ to FAs at the periphery of SACs as detected by interference reflection microscopy (FIG. 4 I–K). Epinectin was not detectable by immunofluorescence in the $\alpha_3\beta_1$-FAs probably due to physical exclusion of anti-$\alpha_3\beta_1$ antibodies from the adhesion sites (20, 21, 101). In contrast to the results obtained above with extraction of $\alpha_6\beta_4$/BPA/epinectin in SACs, the $\alpha_3\beta_1$ integrin in FAs was readily solubilized with 1% Triton X-100 detergent (FIGS. 5E, 5F), further distinguishing the organization and stability of FAs from SACs (20). We consistently observed $\alpha_3\beta_1$ integrins in FAs encircling the $\alpha_6\beta_4$ integrins in the SACs suggesting to us a functional relationship and/or common ligand for both integrin receptors in the SAC and FA adhesion structures.

To further evaluate the role of $\alpha_3\beta_1$ in adhesion to epinectin glycoprotein complex in isolation from the $\alpha_6\beta_4$ integrin, we first sought to identify cells by immunofluorescence microscopy that did not express $\alpha_6\beta_4$ or epinectin antigen, but did express $\alpha_3\beta_1$. Nine different cell populations were examined, including: HFFs; HT1080 fibrosarcoma; Tera-2 teratocarcinoma; T-47D mammary carcinoma cells; Ovcar-4 ovarian carcinoma; and FEPE1 L-8, FE-A, T-47D and FE-H18L, four HSK cell lines resulting from papillomavirus transformation. Examination of the nine cell lines and primary HFKs (for comparison) by immunofluorescence microscopy with P1E1 identified only one, namely, the primary HFKs, that produced significant quantities of epinectin antigen (thus, further justifying our initial belief that HFK may produce an ECM that is unique from other ECMs). In contrast to primary HFKs, human foreskin fibroblasts (HFFs), HT-1080 fibrosarcoma, Tera-2 teratocarcinoma, and T-47D mammary tumor carcinoma cells, while positive for $\alpha_3\beta_4$, were all negative for expression of epinectin. Ovcar-4, an ovarian carcinoma cell line, and FEPE1L-8, FE-A, and FE-H18L, the human papilloma virus-transformed-HFKs (94, 95), expressed epinectin but at low levels relative to HFKs. Expression of $\alpha_6\beta_4$ was also investigated with immunofluorescence microscopy. Of the nine cell lines and primary HFKs cells, only the HFKs, T-47D, FEPE1L8, FE-A, and FE-H18L cells expressed $\alpha_6\beta_4$. Thus, HFF and HT1080 fibrosarcoma cells expressed $\alpha_3\beta_1$, but not epinectin or $\alpha_6\beta_4$, and provided us a model system to study the interactions of $\alpha_3\beta_4$ with epinectin glycoprotein complex.

Figure 6A:
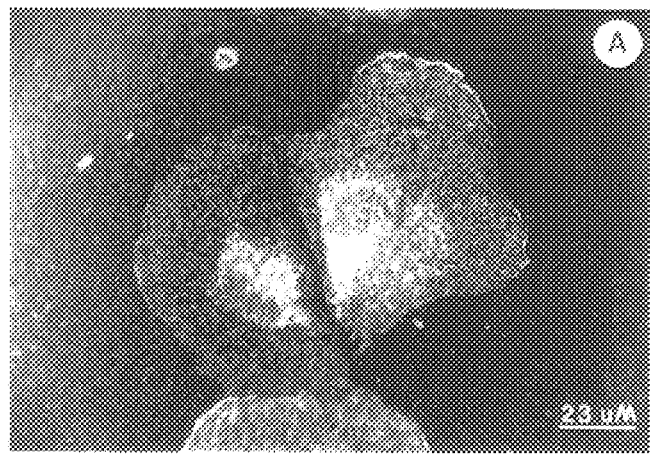
Figure 6B:
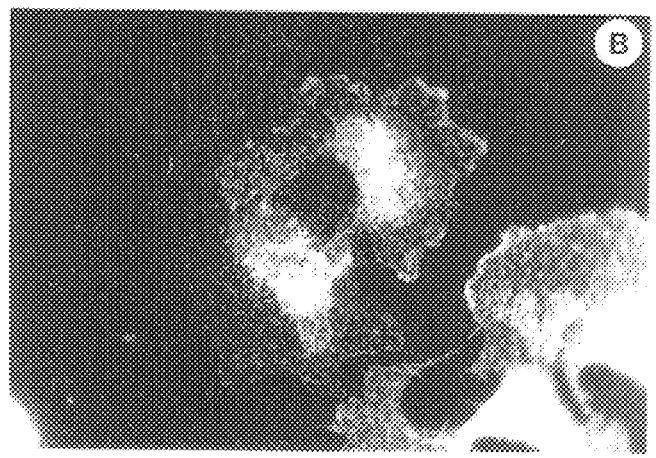
Figure 6C:
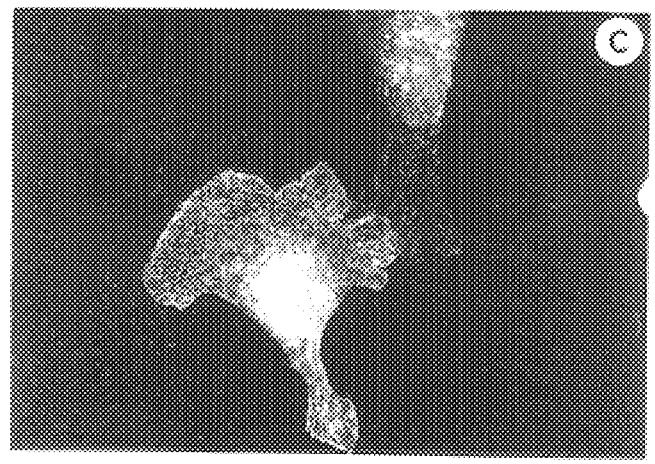
Figure 6D:
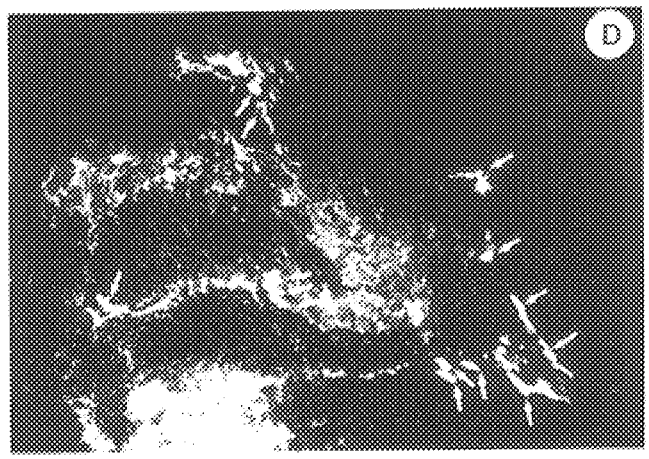
Figure 6E:
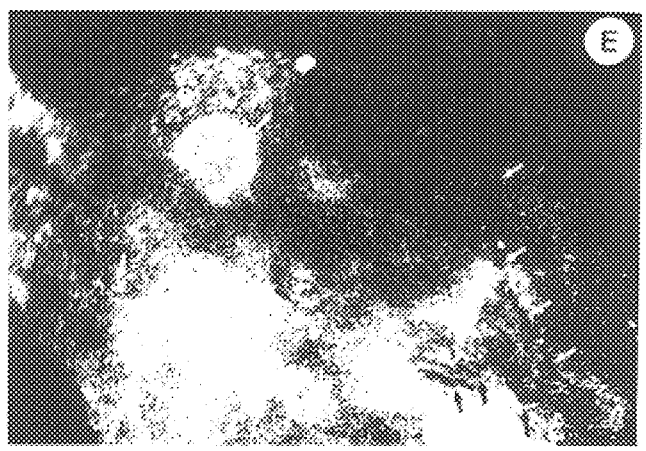
Figure 6F:
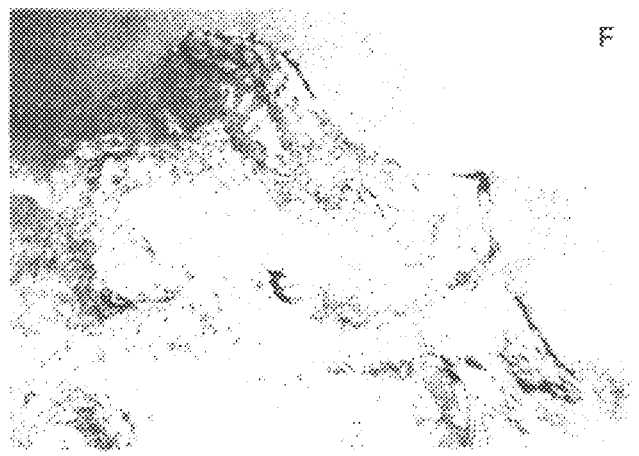

We previously observed that HFFs localized the $\alpha_5\beta_1$ and $\alpha_2\beta_1$ integrins in focal adhesions when the cells were attached to fibronectin- and collagen-coated surfaces respectively (21), and this property was considered to be associated with ligand-induced receptor redistribution on the cell surface. The $\alpha_3\beta_4$ integrin was not previously examined during the interaction of these cells with fibronectin or collagen. To study $\alpha_3\beta_1$ receptor redistribution, HFFs were attached to surfaces coated with fibronectin (FIG. 6A), type I collagen (FIG. 6B), laminin (FIG. 6C), or HFK-ECM (FIGS. 6D–F) for 1 hour. The fixed and permeabilized cells were stained with anti-$\alpha_3\beta_1$ (P1F2, FIGS. 6A–D). The panels D–F (FIGS. 6D–F) are all the same field. The field in FIG. 6E was stained for epinectin (P1E1), and FAs were detected by interference reflection microscopy as shown in FIG. 6F. Arrows in FIGS. 6D–F indicate localization of $\alpha_3\beta_1$ in FAs that contact the adhesion surface and exclude anti-epinectin antibody. When HFFs attached to fibronectin or collagen, they distributed $\alpha_3\beta_1$ over the entire cell surface with no localization of $\alpha_3\beta_1$ in FAs (FIGS. 6A and 6B). When attached to surfaces coated with laminin, the laminin induced thin FAs that were weakly positive for $\alpha_3\beta_1$ (FIG. 6C). Thus, neither fibronectin, collagen, nor laminin appears to constitute a major ligand capable of redistributing the $\alpha_3\beta_1$ integrin receptor on the surface of human foreskin fibroblasts in vitro. In contrast, HFFs that attached to HFK-ECM for only 1 hour, localized $\alpha_3\beta_1$ into FAs as determined by interference reflection microscopy and exclusion of the P1E1 antibody (FIGS. 6D–F). The $\alpha_3\beta_1$ co-distributed with epinectin glycoprotein complex in both FAs and the ring structures characteristic of SACs. These results indicated that epinectin glycoprotein complex, as the major component of HFK-ECM, controlled the formation of $\alpha_3\beta_1$-FAs better than any previously identified ECM ligand.

5.6 Immunopurification of Epinectin

Epinectin glycoprotein complex was immunopurified from conditioned culture medium. This was accomplished in a stepwise fashion, first, by affinity-purification of MAb P1E1 from hybridoma culture medium on Protein G-Sepharose (Pharmacia, Piscataway, N.J.). Second, the purified monoclonal antibody was covalently coupled to Affigel-10 (Bio-Rad Laboratories, Richmond, Calif.; forming the P1E1-affinity-column). Third, conditioned culture medium from confluent cultures of HFKs was passed over a gelatin-Sepharose column (Pharmacia) to remove fibronectin. Fourth, the flow-through from the gelatin sepharose column was then passed over the P1E1-affinity-column. Unbound protein was removed by washing with PBS; and then the bound epinectin antigen was eluted with 3M KSCN and dialyzed against PBS. The epinectin glycoprotein complex purified on the P1E1 affinity-column contained the complex of E200, E170, E145, E135, and E36 covalently linked subunits, although lower levels of E200 were present than in HFK-ECM.

5.7 Specificity of Integrin $\alpha_3\beta_1$-Mediated Cellular Adherence to Epinectin Soluble, purified epinectin glycoprotein complex was coated on non-adhesive polystyrene plastic surfaces to examine its ability to promote adhesion of HT1080 cells through the $\alpha_3\beta_1$ receptor. Inhibition of cell adhesion to various ligands was performed as previously described (20, 21, 59). The specificity of the adhesion for $\alpha_3\beta_1$ was evaluated by testing for inhibition of adhesion with anti-$\alpha_3\beta_1$ MAb (P1B5). For comparison epinectin (EN; 1 $\mu$g/ml), human plasma fibronectin (FN) 10 $\mu$g/ml), type I collagen (CN; 10 $\mu$g/ml) EHS laminin (LN; 10 $\mu$g/ml), or BSA (5 mg/ml) were coated on non-adhesive plastic surfaces (2 hours), washed, and blocked with heat denatured BSA for 1 hour. The cells were labeled with $Na_2{}^{51}CrO_2$ (New England Nuclear; 50 $\mu$Ci/ml for 2–4 hours) and were allowed to adhere (in the presence of the following inhibitory antibodies) to the protein-coated surfaces in the presence of the hybridoma supernatants for 1.5 hours. The inhibitory antibodies indicated in FIG. 7 include: SP2 as a control, non-inhibitory antibody. P4C10, inhibits cell adhesion via all $\beta_1$-containing integrins. GoH3, anti-$\alpha_6(\beta_1)$ laminin receptor in HT1080. P1H5, anti-$\alpha_2\beta_1$ collagen receptor. P1D6, anti-$\alpha_5\beta_1$ fibronectin receptor. P1B5, anti-$\alpha_3\beta_1$ epinectin receptor. The bars in FIG. 7 represent the mean values of three assays. Unattached cells were removed by washing and the adherent cells dissolved in SDS/NaOH and quantitated in a gamma counter. The results presented in FIG. 7 show that purified epinectin glycoprotein complex mediated adhesion of HT1080 cells to the previously non-adhesive plastic surface, and the cellular adhesion to epinectin-coated plastic was blocked in a specific manner by the P1B5 MAb to the $\alpha_3\beta_1$ integrin receptor. More specifically, the data presented in FIG. 7 show that HT1080 cells attached to epinectin glycoprotein complex-, fibronectin-, and collagen-coated and non-adhesive plastic surfaces and laminin (FIG. 7). Antibodies against the $\alpha_5\beta_1$ (P1D6) fibronectin receptor, the $\alpha_2\beta_1$ (P1H5) collagen receptor, and the $\alpha_6\beta_1$ (GoH3) laminin receptor (64, 102) specifically inhibited HT1080 adhesion to their corresponding ligands but had no inhibitory effect on adhesion to epinectin glycoprotein complex. Anti-$\beta_1$ MAb (P4C10) inhibited cell adhesion to all ligands involving $\beta_1$-containing integrins.

The testing was next expanded to include cells other than HT1080. P1B5 (anti-$\alpha_3\beta_1$) was found to inhibit the adhesion of HFK and FE-H18L cells to epinectin. These results established $\alpha_3\beta_1$ as a primary receptor for cell adhesion to epinectin glycoprotein complex. Further, the MAb inhibition results clearly distinguish cellular adhesion to laminin via $\alpha_6\beta_1$ from epinectin glycoprotein complex via $\alpha_3\beta_1$. These findings will establish a test cell assay system useful for identifying epinectin produced by other epithelial cells.

5.8 Epinectin Localization in Normal Epithelial Basement Membrane

We compared the distributions of epinectin to laminin, $\alpha_3\beta_1$ and $\beta_4$ by immunoperoxidase staining of cryostat sections of normal skin, tonsil (below), and lung (below) (FIGS. 8A–8P). The results presented in FIGS. 8A–8H show cryostat sections of the SKIN (human neonatal foreskin) and SPLIT SKIN (skin from a patient with Junctional Epidermolyses Bullosis that spontaneously separates between the BM and basal cells). TONSIL and LUNG were stained with the indicated antibodies (ANTI-EPINECTIN, etc.). (The magnification in FIGS. 8A–8P prior to photographic enlargement was 160×.) (Arrows and letter abbreviations are used in FIGS. 8A–8P to identify the following structures: namely, BM= epidermal basement membrane; S=epithelial sweat glands in dermis; D=duct of sweat gland in dermis; V=venule; BC=basal cells of epidermis; C=BM of capsular epithelium; LF=lymphoid follicles (germinal centers); E=BM of ciliated epithelium in bronchus; M=bundles of smooth muscle cells adjacent bronchus; and SMG= submucosal glands.)

The distribution of receptors and ligands in tissue was determined by immunoperoxidase microscopy of the cryostat sections. Cryostat sections ($6\mu$) were prepared from human tissues embedded in OCT medium after snap freezing in isopentant/liquid nitrogen. All sections were fixed with 2% formaldehyde in 0.1M NaCacodylate pH 7.2 in 0.1M sucrose for 20 minutes followed by permeabilized with 1% Triton X-100 for 15 minutes. The sections were incubated with primary antibodies and peroxidase-conjugated secondary antibodies.

In skin (FIGS. 8A–8D; row labeled SKIN), antibodies against epinectin, laminin, $\alpha_3\beta_1$ and $\beta_4$ localized to the BM region separating the epidermis and dermis and to epithelial sweat glands (S) and ducts (D) in the dermis. Epinectin antigen was not present in laminin-positive endothelial BMs in venules (V) in the dermis.

5.9 Epinectin Antigen Localization in Diseased Epithelial Basement Membrane

Split skin from a patient with Junctional Epidermolyses Bullosa (JEB) was also analyzed by immunoperoxidase staining in FIGS. 8E–8H (above) for epinectin antigen, laminin, $\alpha_3\beta_1$, and $\beta_4$. JEB is an inherited disorder that results in disruption of basal cell attachment to the BM with a corresponding decrease in hemidesmosomes (103, 104). In cryostat sections of skin from a patent with JEB (FIGS. 8E–8H, labeled SPLIT SKIN), the basal epidermis spontaneously separated from the BM. Epinectin antigen and laminin both localized to the BM floor of the split skin indicating that epinectin glycoprotein complex was a component of the BM. In contrast, $\alpha_3\beta_1$ and $\beta_4$ localized to the roof of the split in the basal cells (BC).

5.10 Epinectin Localization in Lymphoid Tissues

In tonsil (TONSIL, FIGS. 8I–8J), P1E1 (ANTI-EPINECTIN) localized to lymphoid follicles (LF), or germinal centers as a fine filamentous network, possibly in reticular fibers, and the basement membrane of the lymph node capsular epithelium (C). In contrast, laminin (ANTI-LAMININ (R5922), FIG. 8I) was weakly expressed in the lymphoid follicles and capsular BM and strongly expressed in the venous sinuses (V). Both $\alpha_3\beta_1$ and $\beta_4$ were expressed in basal cells associated with the capsular BM. However, neither $\alpha_3\beta_1$ nor $\beta_4$ was detectable as major components of lymphoid follicles.

5.11 Epinectin Localization in Lung Tissues

In lung (LUNG, FIGS. 8M–8P), epinectin and laminin localized to the BM of ciliated epithelium (E) and submucosal glands (SMG) in the bronchus. $\alpha_3\beta_1$ was adjacent epinectin antigen in the basal plasma membranes of the ciliated epithelial cells. In contrast, $\beta_4$ was only sporadically expressed along the basal plasma membrane (E). Both laminin and $\alpha_3\beta_1$ were strongly expressed in bundles of smooth muscle cells (M) and veins (V) while epinectin antigen was absent.

5.12 Epinectin Localization in Other Tissues and Organs

Epinectin was absent from BM of heart muscle, mesothelium, brain, and glomerulus and tubules in kidney, while laminin was expressed. Epinectin was present in the BM separating the intestinal epithelium from the lamina propria. These results identified epinectin glycoprotein complex as a component of epithelial BMs particularly in organs of endodermal and ectodermal (but not neural) origin. Epinectin glycoprotein complex was not present in muscle, neural, and endothelial BMs.

5.13 Epinectin, $\alpha_3\beta_1$, and $\beta_4$ Localize at the Cell-Basement Membrane Junction The ultrastructural localization of epinectin, $\alpha_3\beta_1$, and $\beta_4$ was determined by immunoelectron microscopy of human skin. Electron micrographs are presented in FIGS. 9A–F of immunoperoxidase-stained human neonatal foreskin which was stained with the following antibodies and achieving the following results: namely, (FIG. 9A) control staining with SP2 culture (supernatant is negative; hemidesmosomes and desmosomes are detectable); (FIG. 9B) P1F2 ($\alpha_3\beta_1$ is detectable on the apical, lateral, and basal membranes; staining was also observed in desmosomes); (FIG. 9C) and (FIG. 9D) E31 (the $\beta_4$ subunit is localized to the basal surface and increased staining localized to hemidesmosomes at the origin of keratin filaments); and (FIG. 9E) and (FIG. 9F) P1E1 (epinectin is present in the Lamina lucida along the entire basal membrane but particularly adjacent hemidesmosomes). (Abbreviations used in FIGS. 9A–F include: BM=basement membrane; IC=intercellular contacts; BS=basal membrane surface; KF=intermediate filaments; HD=hemidesmosomes; D=desmosomes; and C=collagen filaments.)

Figure 9A:
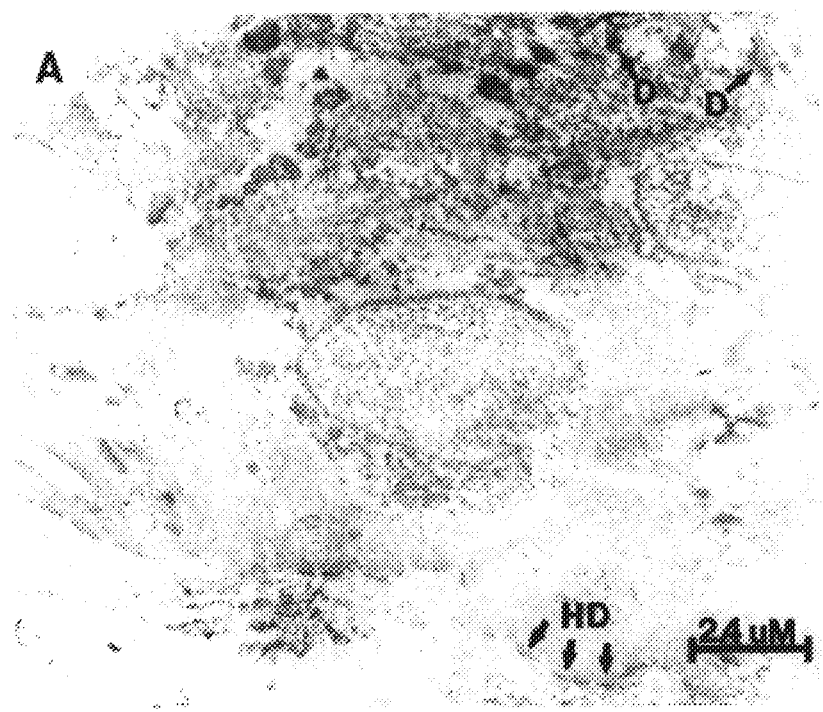
Figure 9B:
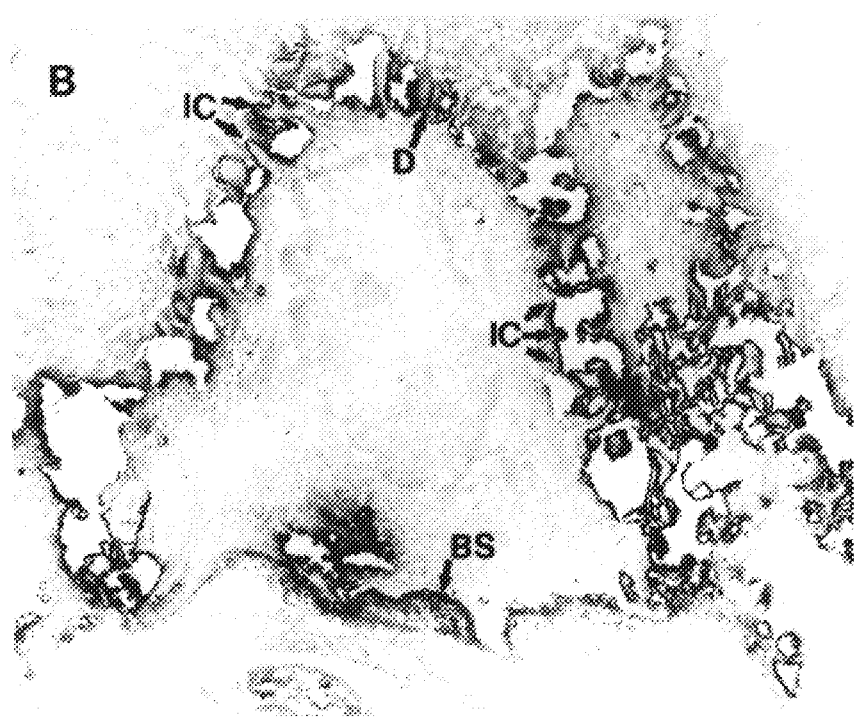
Figure 9C:
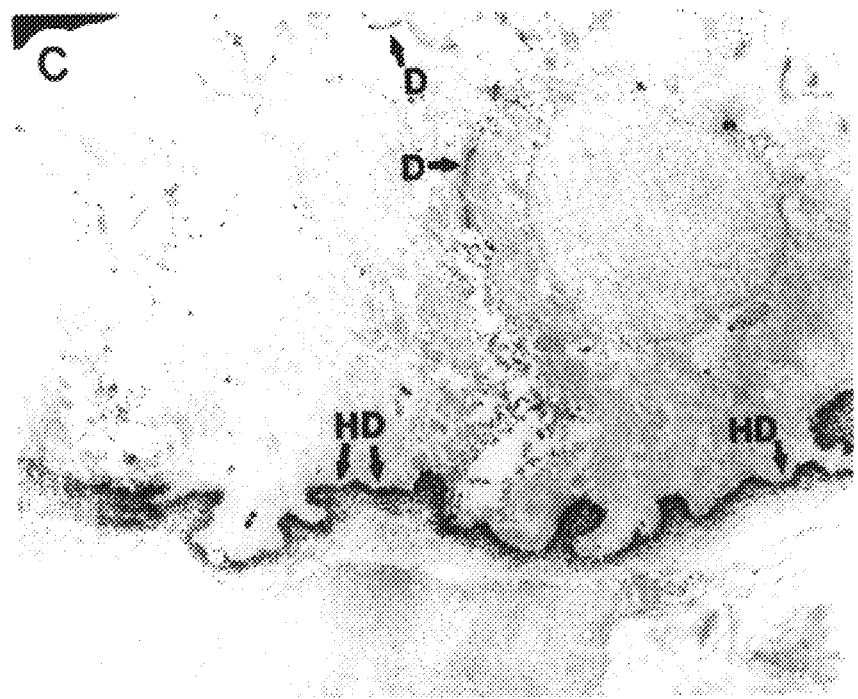
Figure 9D:
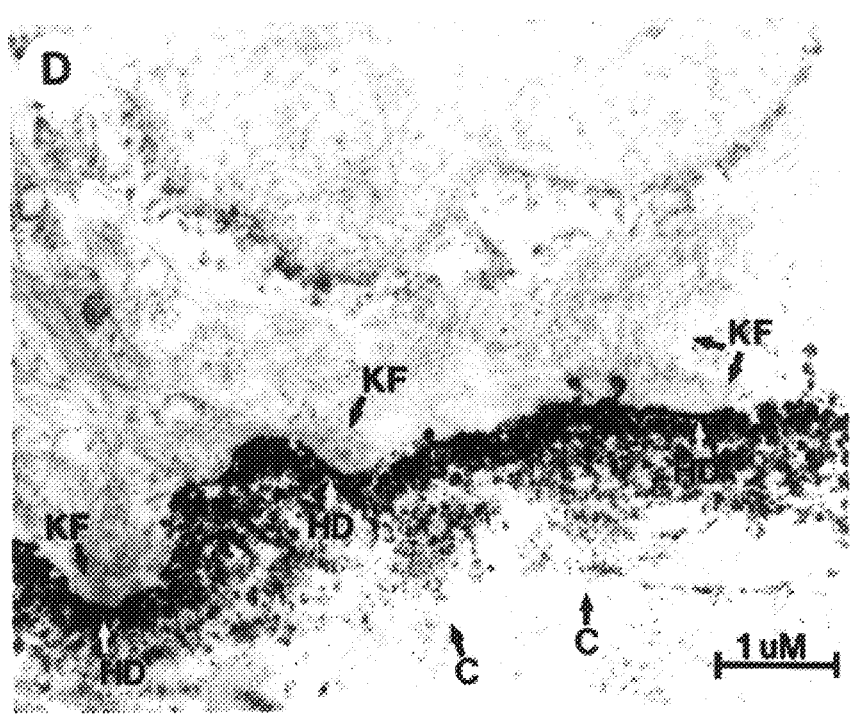

We reported previously that $\alpha_6\beta_4$-containing SACs in HFKs are homologous to hemidesmosomes in skin (20). Consistent with this suggestion and the report of Stepp et al. (19), immunoelectron microscopy localized $\beta_4$ to hemidesmosomes at origins for intermediate filaments (FIGS. 9C and D).

For immunoelectron microscopy, tissue was fixed (30 minutes in 3% paraformaldehyde/0.5% glutaraldehyde in PBS) prior to freezing and cryostat sectioning ($6\mu$), followed by immunoperoxidase staining with P1F2 and P1E1. Because MAb 3E1 required milder fixation conditions, tissue was cryostat sectioned, then fixed (2% paraformaldehyde in PBS for 15 minutes) followed by peroxidase staining and further fixation (2.0% paraformaldehyde and 2.5% glutaraldehyde in 0.1M Ca-codylate buffer). All tissue sections were post-fixed for 1 hour in 1% osmium tetroxide, alcohol dehydrated and infiltrated with Epon 812-tm resin (Polysciences, Warrington, Pa.) as described (105). Thin sections were cut (600–800 Å). No uranyl acetate staining was performed.

Figure 9E:
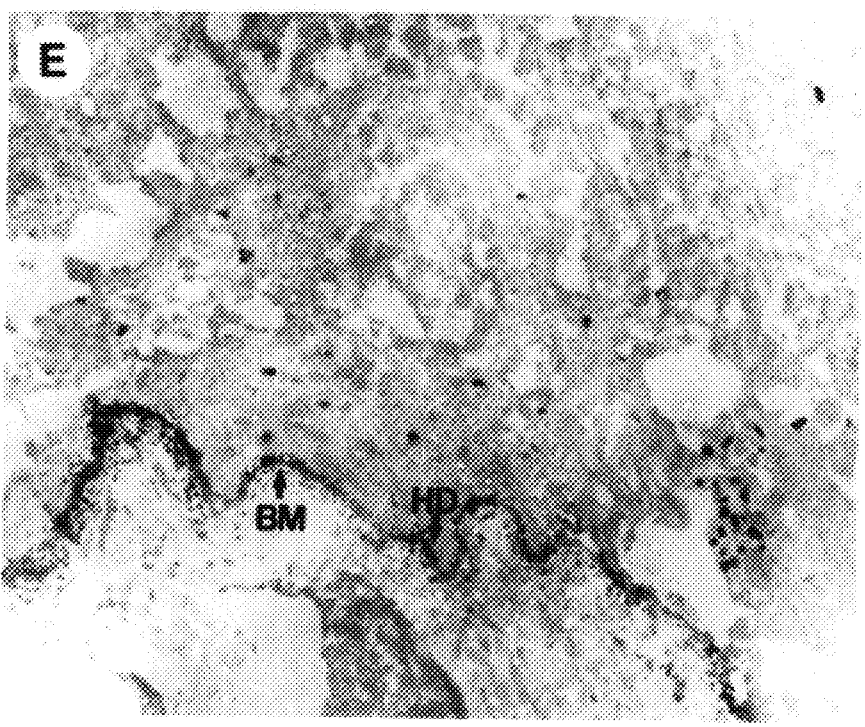
Figure 9F:
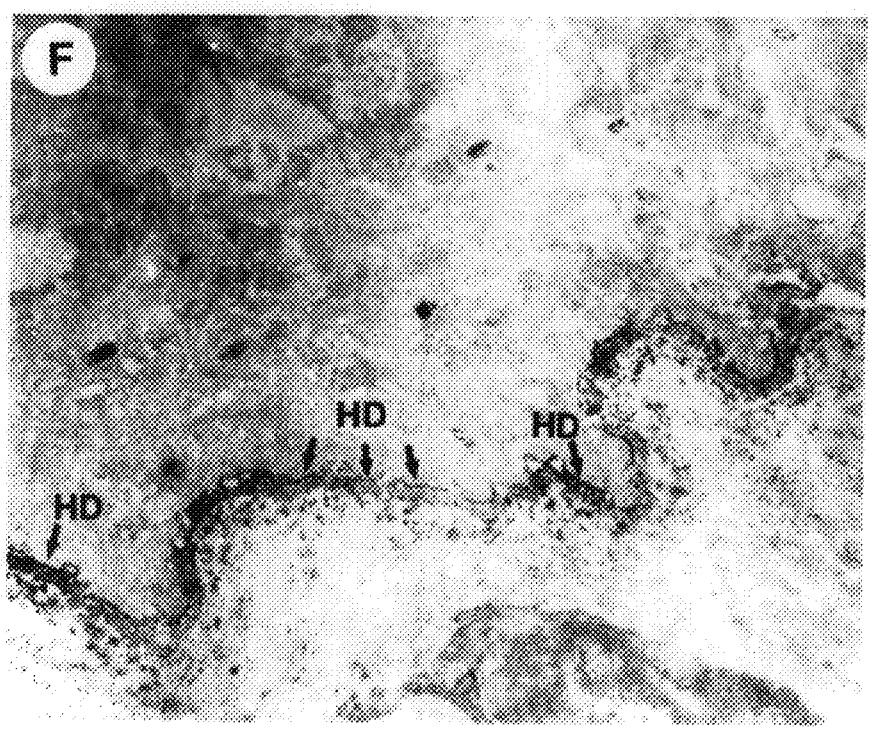

Consistently, epinectin localized in the Lamina lucida of epidermal BM (FIGS. 9E, 9F). Epinectin appeared to directly contact the entire basal surface of the basal cell plasma membrane but was elevated in concentration adjacent $\beta_4$-containing hemidesmosomes. $\alpha_3\beta_1$ localized along the basal membrane as well as the lateral and apical membranes of basal cells (FIG. 9A), consistent with the dual roles for $\alpha_3\beta_1$ in adhesion to epinectin glycoprotein complex and in cell-cell adhesion (21). In many fields, we observed $\alpha_3\beta_1$ localization in desmosomes indicating an association of $\alpha_3\beta_1$ and epinectin glycoprotein complex with desmosomes. Nonspecific staining of controls (FIG. 9A) was not detectable while hemidesmosomes and desmosomes were identifiable with anti-$\alpha_3\beta_1$ and P1E1.

The foregoing is exemplified by the representative examples that follow. Specific protocols are described in the appended Materials and Methods section.

6. EXAMPLE 1
Process for Preparing HFK-ECM and HFF-ECM

Human foreskin keratinocytes (HFKs) were prepared as described by Boyce and Ham (106) and maintained by serial passage in serum-free keratinocyte growth medium (KGM; Clonetics, San Diego, Calif.) containing insulin, 10 ng/ml epidermal growth factor hydrocortisone, and 50 $\mu$g/ml bovine pituitary extract.

Keratinocytes have a distinctive composition of glycoproteins which is extracted with SDS sample buffer (12) and is visualized by SDS-PAGE (12): namely, (a) cytokeratins glycoproteins No. 5 (58 kd); No. 6 (56 kd); No. 14/15 (50 kd); No. 16 (48 kd); and, No. 17 (46 kd); (b) and the ivolucrin glycoprotein. Several or all of these keratins are visualized by protein staining, e.g., with Coomassie brilliant blue, or alternatively by Western immunoblotting (107) with monoclonal antibodies AE1 and AE3 (45). Ivolucrin is visualized at an apparent Mr of approximately 140 kd in human keratinocytes by SDS-PAGE (107). Keratinocytes also have a distinctive ultrastructure in tissue culture visible by electronmicroscopy where the cellular colonies are 5 to 6 cells thick with characteristic keratin filaments, tonofilaments, and numerous desmosomes.

Human foreskin fibroblasts (HFFs) were prepared by protease/collagenase digestion (Methods in Enzymology). For preparation of HFK-ECM or HFF-ECM of HFK or HFF cells, respectively, were seeded in KGM into 7.5 cm diameter tissue culture plastic dishes, and the dishes were incubated at 37° C. in a humidified atmosphere consisting of 95% air/5% $CO_2$ preferably for 1–3 days. The HFK-ECM or HFF-ECM was prepared by a three-step extraction procedure. First, the adherent HFK and HFF cells and their membrane and cytoplasmic constituents were removed by extraction with detergent in the continuous presence of protease inhibitors and 2 mM N-ethylmalaeimide (to inhibit intramolecular cross-linking). Suitable detergents and concentrations for this first step include for example 1% (v/v) Triton X-100-tm anionic detergent (Sigma), Empigen BB-tm Zwitterionic detergent or 100 mM octyl glucoside. Suitable protease inhibitors include diisopropyl fluorophosphate (DFP; Sigma), benzamidine, polybrene, kallikrein inhibitor, or phenyl methyl sulfonyl fluoride (PMSF; Sigma), which may be used individually or in combination as necessary to inhibit cellular protease activity (as evidenced by successful preparation by the complete three-step extraction procedure of HFK-ECM capable of adhering HFF or HT1080 cells in a manner inhibitable with antibodies to the $\alpha_3\beta_1$ integrin receptor; see below; Example 6, "Functional Properties of Epinectin"). (These same protease inhibitors were used at the same concentrations in the solutions used in the second and third steps, below.) The second step, in the three-step extraction procedure, involves solubilizing and removing nuclear and cytoskeletal components with a solution containing 2M urea (ammonium-free), 1M NaCl, and protease inhibitors; and the third step involves solubilization of any residual cellular components with a solution of 8M urea and protease inhibitors. The ECM remaining attached to the culture dish after the three-step extraction procedure of HFK culture dishes, or HFF culture dishes, is referred to as HFK-ECM or HFF-ECM, respectively.

HFK-ECM can be solubilized into 0.5% w/v SDS by scraping the culture dishes with a rubber policeman; its constituent glycoproteins consist essentially of four to five covalently linked disulfide-bonded glycoproteins with an apparent Mr>450 kd; i.e., they do not enter an 8% SDS-PAGE (12), traverse the upper 3.5% stacking gel, and stop at the 8% gel interface; and the four to five covalently linked glycoproteins can be separated by reduction and SDS-PAGE run under reducing conditions (12) into components with apparent Mr of 200 kd, 170 kd, 145 kd, 135 kd and 36 kd. In contrast, the matrix produced by cultured fibroblasts consists essentially of a non-covalently linked dissociable complex of type I collagen, fibronectin, and heparin-containing and chondroitin-sulfate-containing proteoglycans (108), most of which is extracted by the three-step sequential extraction procedure.

7. EXAMPLE 2
Process for Preparing Antibody Binding Partners to Epinectin as Exemplified by Rabbit Antisera and Monoclonal Antibody Specific for Epinectin Glycoprotein Complex Useful antigens for producing monoclonal and polyclonal antibodies include HFK cells, and also include HFK-ECM (prepared as described in Example 1), or individual glycoproteins present in HFK-ECM which are physically separable by techniques obvious to those skilled in the art including at least SDS-PAGE.

Various procedures well known in the art are useful for the production of polyclonal antibodies to antigenic epitopes in HFK-ECM. Various host animals can be immunized by injection with HFK-ECM proteins, fragments thereof, or synthetic peptides constructed to mimic the amino acid sequence in an HFK-ECM protein. Adjuvants may be used to augment the immune response and immunogenicity of small proteins, and peptides may be enhanced by coupling them to larger "carrier" molecules.

Monoclonal antibodies for therapeutic use may be human monoclonal antibodies or chimeric human-mouse (or other species) of monoclonal anibodies. Human monoclonals may be made by numerous techniques known in the art and the subject of many reviews and detailed techniques manuals, e.g., Olsson et al., Methods in Enzymology 92:3–16 (1982). Similarly, techniques are well known by which chimeric antibody molecules may be prepared containing a mouse V-region antigen binding domain with human constant regions. Molecular cloning of antibodies may also be used to construct recombinant DNA molecules which encode monoclonal antibody, and chimeric monoclonal antibodies from different species, and these methods are also well known to those skilled in the art.

HFK cells for use as an immunogen to produce monoclonal antibodies were prepared as follows. First, HFK cells were seeded in plastic tissue culture dishes. After 7 days the cells were detached from the substrata and collected by centrifugation. The cell pellet was resuspended in PBS and mixed with an equal volume of Complete Freund's Adjuvant. 0.2 ml was injected into each of 2sc and 2im sites in RBF/Dr mice. Third, the animals were boosted after 14 and 21 days.

HFK-ECM was collected from the surface of culture dishes by scraping with a rubber policeman into 0.5% SDS and dialyzing against PBS to remove the SDS. This HFK-ECM aggregated protein suspension was mixed with an equal volume of Complete Freund's Adjuvant and 100 $\mu$l of the adjuvant solution was injected at each of 2sc and 2im sites in New Zealand white rabbits. The animals were boosted at 14 and 21 days.

Immune spleen cells from HFK-immunized mice were prepared and fused with NS-1/FOX-NY murine myeloma cells using polyethylene glycol as described (59, 99, 100). (These and the following methods (below) are also useful for producing monoclonal antibodies from mice immunized with HFK-ECM and individual glycoproteins present in HFK-ECM). Viable heterokaryons were selected in RPMI 1640 supplemented with adenine/aminopterin/thymidine (AAT; 100). Heterokaryons producing antibodies (termed Hybridomas) specific for HFK-ECM and not binding to HFF-ECM were selected. The clones designated P1E1 and P1H8 were derived, as an example, by this method.

Other immunochemical methods for selecting positive hybridomas producing antibodies reacting with epinectin glycoprotein complexes will be obvious to those skilled in the art, including at least selection by ELISA, RIA, and Western blotting using purified epinectin antigens (Example 3, below) and/or HFK-ECM and HFF-ECM.

It will also be understood that antibodies other than monoclonal antibodies may be produced (e.g., by immunizing rabbits, goats, or other animals), and will be equally useful.

The specific immunochemical properties of monoclonal (or other) antibodies specific for epinectin antigens are detailed below in Example 5.

8. EXAMPLE 3
Process for Preparing Epinectin, and Epinectin Complex

Epinectin complex was substantially purified by mechanically scraping HFK-ECM (prepared in Example 1) into 0.5% SDS. When subject to reduction of disulfide bonds, e.g., with DTT or 2-mercaptoethanol, the epinectin complex prepared in this manner exhibited epinectin glycoproteins with apparent molecular sizes of 200 kd (E200), 170 kd (E170), 145 kd (E145), 135 kd (E135), and 36 kd (E36) when reduced and electrophoresed under reducing conditions on 8% SDS-PAGE with a 3.5% stacking gel (12).

A mixture containing predominantly a covalently-linked epinectin glycoprotein complex was substantially purified from the conditioned medium of HFK cells as outlined in FIG. 3. This was accomplished in a stepwise fashion involving, first, affinity purification of MAb P1E1 from hybridoma culture medium on Protein G-sepharose using the methods recommended by the manufacturer (Pharmacia, Piscatawy, N.J.). Second, the P1E1 antibody was immobilized on a matrix (i.e., to form a P1E1-affinity-column) by covalently coupling purified monoclonal antibody to Affigel-10 according to the manufacturer's instructions (Bio-Rad Laboratories, Richmond, Calif.). Third, conditioned medium from confluent cultures of HFK cells was passed over a gelatin-sepharose column (Pharmacia) to remove fibronectin. Fourth, the flow-through from the gelatin-sepharose column was passed over the P1E1-affinity-column; unbound protein was removed by washing with PBS until the wash had an OD280 of less than 0.001 units; the bound epinectin glycoprotein complex was eluted with 3M KSCN, and the fractions containing the eluted protein were pooled and dialyzed overnight at 4° C. against at least 10 volumes of PBS. The substantially-purified covalently-linked epinectin glycoprotein complex purified in this manner (i.e., from conditioned media) comprised predominantly E170, E145, E135, and E36, although low levels of E200 were also present by SDS-PAGE.

It will be understood by those skilled in the art that MAb P1E1 is purified using affinity chromatography on other chromatographic resins containing compositions binding murine Ig (i.e., protein A-sepharose, or anti-IgG or protein M-sepharose); or alternatively, by specific binding of MAb P1E1 to epinectin complex or epinectin glycoprotein covalently bound to a matrix (e.g., Affigel-10, Bio-Rad or CNBr-sepharose, Pharmacia).

It is also obvious to those skilled in the art that the relatively large molecular size of the epinectin glycoprotein complex (calculated to at least greater than 450 kd to 650 kd, assuming equimolar amounts of each epinectin glycoprotein), and insolubility of HFK-ECM glycoproteins in aqueous solutions will be used to advantage in purification schemes designed to separate these complexes from numerous smaller soluble cellular components. Purification of epinectin glycoprotein complex from HFK-ECM or HGK-conditioned medium by conventional column chromatography was not possible due to the relatively poor solubility of the complex and its large molecular weight. It is also obvious that reduction and alkylation of the disulfide bonds will be useful for producing epinectin glycoproteins, where intramolecular cross-linking (leading to formation of aggregates) is inhibited by 2 mM n-ethyl malaeimide and similar chemical agents. However, it was also discovered that reduction and alkylation leads to inactivation of the epinectin ligand adherence promoting activity and it is apparent that preserving the secondary structure of epinectin glycoproteins is important to preserving their functional activity.

The epinectin (E170) protein was substantially purified from either HFK-ECM or the affinity-purified epinectin glycoprotein complex by SDS-PAGE. It is understood by those skilled in the art that epinectin is also purified by other conventional means from conditioned media of other epithelial cells under other conditions of growth.

The physical, immunochemical, and functional properties of epinectin glycoprotein complex is detailed in Examples 4, 5, and 6, respectively, below.

9. EXAMPLE 4

Physical Properties of HFK-ECM, and Epinectin Glycoprotein Complex

HFKs were seeded into 7.5 mm plastic tissue culture dishes, as described in Example 1, and incubated in KGM medium (supplemented as described in Example 1) and containing $^{35}$S-methionine or alternatively 3H-glucosamine. HFK-ECM was prepared according to Example 1, which includes sequential extraction with 1% Triton X-100, 2M urea/1M NaCl, and then 8M urea. These conditions are known by those skilled in the art to frequently be sufficient to dissociate non-covalently associated proteins, and also, to be sufficient to denature other proteins. HFK-ECM is also stable to extraction with 6M Guanidine hydrochloride and 4M Sodium trichloroacetate. Thus, it may be said that the epinectin complex is relatively stable to denaturing conditions, and relatively resistant to extraction from the plastic tissue culture substrata (although it has been observed that some low levels of epinectin glycoprotein complex are extracted with 8M urea).

$^{35}$S-methionine biosynthetically-radiolabeled HFK-ECM glycoproteins (above) and non-radiolabeled HFK-ECM glycoproteins were solubilized into 0.5% SDS (w/v) (sodium dodecyl sulfate; Bio-Rad) by mechanical scraping of the tissue culture dishes with a rubber policeman, and the glycoproteins solubilized in this manner were then subjected to SDS-PAGE essentially according to Laemmli (12) op. cit. on 8% gels under non-reducing and reducing conditions using a 3.5% stacking gel. Non-radiolabeled glycoproteins were visualized by staining with Coomassie Brilliant Blue (Bio-Rad) and the radiolabeled glycoproteins were visualized by fluorography although other methods known to those skilled in the art for detecting biosynthetically radiolabeled glycoproteins are equally useful. Under reducing conditions five glycoproteins were visualized in epinectin glycoprotein complex with apparent molecular sizes in the 8% gel of 200 kd (E200), 170 kd (E170), 145 kd (E145), 135 kd (E135) and 36 kd (E36), (FIG. 1, lanes 4 and 6,$^{35}$S-methionine biosynthetically radiolabeled); lane 9 ($^{3}$H glucosamine-radiolabeled); and lane 8 (non-radiolabeled). The five glycoproteins appeared to be present in about equal amounts in the biosynthetically radiolabeled HFK-ECM samples (FIG. 1, lanes 4 and 9). An approximate combined Mr for the non-reduced epinectin glycoprotein complex was calculated to be at least 450 kd–650 kd (excluding any contribution of proteoglycan to the molecular weight, see below). The non-radiolabeled sample of HFK-ECM appeared to contain lesser amounts of E200 (relative to E170, E145, or E135) than that present in biosynthetically-radiolabeled samples. (These observed differences between E200 in radiolabeled and non-radiolabeled samples may have a trivial explanation, e.g., E200 may not stain well with Coomassie blue; or, E200 may not incorporate the same amount of $^{35}$S-methionine as the other epinectin glycoproteins. Alternatively, there may be differences in the amounts of E200 in the epinectin glycoprotein complexes at different stages in HFK cell growth (e.g., subconfluent vs. confluent). Or, it is also possible that (1) recently synthesized E200 may be covalently associated with the epinectin glycoprotein complex and that (2) with time, reduction of the disulfide bonds (e.g., with glutathione or disulfide-exchange) may lead to liberation of E200 from the complex. Under nonreducing conditions the epinectin complex in HFK-ECM was visualized as a high molecular weight complex which did not enter the 8% gel. (FIG. 1, lane 5).

The five glycoproteins in the epinectin complex were not biosynthetically radiolabeled with $^{35}$SO$_4^{-2}$ (FIG. 1, lane 10) indicating that they are not sulfated proteoglyeans. However, independent of the epinectin complex the HFK-ECM (biosynthetically radiolabeled for 15 hours with 50 μCi/ml of $^{35}$SO$_4^{-2}$ in KGM containing 1 mg/ml HD-BSA as a carrier protein) contained three high-Mr sulfated proteoglyeans that were associated with the HFK-ECM (FIG. 1, lane 10) and thus with the epinectin complex in the HFK-ECM (FIG. 1, lane 9). The first sulfated proteoglycan did not enter the 3.5% stacking gel and the second barely entered the stacking gel but did not enter the 8% running gel.

10. EXAMPLE 5

Immunochemical Properties of Epinectin Antigen, Epinectin Complex, and Monoclonal Antibody to Epinectin Monoclonal antibodies P1E1 and P1H8 selected (above, Example 2) for specific binding to HFK-ECM and not to HFF-ECM, e.g., P1E1, bound to $^{35}$S-methionine radiolabeled epinectin complex in HFK-conditioned media (prepared as in Example 3, above) and the immunoprecipitate formed by adding a second antibody (i.e., rabbit or goat anti-murine IgG and IgM H and L chain sera) with carrier proteins (e.g., diluted murine sera containing murine IgG and IgM) contained E200, E170, E145, E135 and E36. (FIG. 2, lanes marked "P1E1").

P1E1 did not bind to any of the epinectin glycoproteins when they had been reduced and subjected to SDS-PAGE under reducing conditions, suggesting that the P1E1 antigenic epitope may be conformational and denatured in these treatments.

The glycoproteins immunoprecipitated by P1E1 include relatively greater amounts of E170 than E135, E145, or E200. These findings indicate: a) that E170 may contain the P1E1-reactive antigenic epitope in the epinectin complex; and b) that E170 may also exist (in HFK-conditioned media as a glycoprotein independent of the epinectin complex.

P1H8, while binding to HFK-ECM and soluble epinectin complex in HFK-conditioned media, did not bind to the endogenous epinectin complex in HFK cells unless the plasma membrane was permeabilized to allow entry of antibodies into the cytoplasm. P1H8 immunoprecipitated E36 from HFK-conditioned media in amounts relatively greater than E200, E170, E145 or E135 indicating: a) that E36 contains the P1H8 antigenic epitope in the epinectin glycoprotein complex; and b) that E36 is also present in HFK-conditioned media as a glycoprotein independent of the epinectin complex.

Verification that monoclonal (or polyclonal) antibody is directed to epinectin glycoprotein complex is obtained by $^{35}$S-methionine or $^3$H-glucosamine biosynthetically-radiolabeling HFK cells, collecting the conditioned medium, and using the antibody in question to form an immunoprecipitate with the biosynthetically radiolabeled antigens in the conditioned medium. Antigens in the epinectin glycoprotein complex exhibit characteristic molecular weights of 170±20 kd, 145±20 kd, 135±20 kd, 36±15 kd (with variable amounts of E200±20 kd) under reducing conditions on 8% SDS-PAGE and when run according to Laemmli, (12).

Additional verification that monoclonal (or polyclonal) antibody is directed to epinectin glycoprotein complex can be obtained by examining the pattern of staining of cells in epithelial tissues by immunoperoxidase staining with cryostat sections of tissues (prepared as described above, see "Epinectin Localization in Normal Epithelial BM") (see "Epinectin, $\alpha_3\beta_1$ and $\beta_4$ localization at the cell-BM Junction"). Antibodies to epinectin stain basement membrane materials in normal skin, tonsil, and lung essentially as described (see "Epinectin Localization in Normal Epithelial BM"; "Epinectin Localization in Lymphoid Tissues"; "Epinectin Localization in Lung Tissues"; above). Antibodies to epinectin do not stain BM materials of heart muscle, mesothelium, brain, or glomerulus and tubules in kidney (see "Epinectin Localization in Other Tissues and Organs").

When HFK cells are grown on BSA-coated surfaces the epinectin complex is contained within characteristic "ring structures" in the ECM that are visualized by immunofluorescent staining with P1E1 (see, "Epinectin Distribution in Motile and Non-motile HFKs"). An example of these characteristic "ring structures" formed by epinectin glycoprotein complex in HFK-ECM is provided in FIGS. 4A, C, F. Confirmation that "ring structures" produced by other cells of epithelial origin (i.e., Epith-ECM; i.e., other than HFK) contain epinectin glycoprotein complex will be possible using monoclonal antibodies to epinectin, such as P1E1, and as a preferred embodiment, using these anti-epinectin antibodies in a double antibody immunofluorescence microscopic technique with antibodies binding the $\alpha_3\beta_1$ integrin receptor (e.g., FIGS. 4B, D (GoH3) or BPA (e.g., FIG. 4G). In the latter case, the simultaneous presence of epinectin antigens and $\alpha_3\beta_1$ or BPA in a "ring structure" will confirm that the ECM structure contains the epinectin complex. Additional verification that the "ring structures" identified in this manner contain epinectin will be obtained by extracting the Epith-ECM sequentially with 1% Triton X-100, 2M urea/1M NaCl, and then 8M urea as described in Example 1, above, and in FIGURE legend 5. The "ring structures" containing epinectin complex will be stable under these conditions, in a manner similar to those in HFK-ECM (FIGS. 5A–E).

11. EXAMPLE 6
Functional Properties of Epinectin Complex: Cell Adhesion Assays Test cells which express functional $\alpha_3\beta_1$ integrin receptors will bind to ligand in the epinectin complex, and if epinectin is coated onto the surface of a normally non-adhesive substratum (epinectin-coated substratum) the interaction between the epinectin ligand and the $\alpha_3\beta_1$ integrin is sufficient to modulate adhesion of the test cells, in this case, by increasing their adhesion to the epinectin-coated substratum. The adhesion of the test cells to the substratum will be optimal after 24 hours of incubation at 37° C. to allow washing to remove non-adherent cells, and the relative number of adherent cells will be determined by microscopically counting the adherent test cells or by radiolabeling the test cells prior to incubation in the assay, such as with Na$^{51}$CrO$_4$ or other suitable label known to those skilled in the art. The preferred embodiments relate to test cells which do not express the $\alpha_6\beta_4$ receptor or epinectin in amounts sufficient to be detected by immunofluorescence microscopy, and HFF and HT1080 fibrosarcoma cells are examples of such test cells. Polystyrene plastic petri dishes (i.e., bacteriological grade petri dishes as opposed to tissue culture plastic dishes) are examples of a non-adhesive substratum which will be useful for coating with epinectin. The epinectin coating on the non-adhesive substrate may be applied by any of a variety of means known to those skilled in the art (e.g., by soaking, spraying, dipping, etc.) using a concentration of protein sufficient to accomplish the desired result of test cell adhesion to the epinectin-coated substratum. Epinectin useful for coating the non-adhesive substratum will be, as an example, the epinectin glycoprotein complex purified in Example 3, above, from HFK-conditioned medium, although other cellular sources, preparative purification methods, and substantially equivalent epinectin compositions will also be useful. To verify that the adherence of the test cells to the epinectin-coated substratum involves a specific binding interaction between the $\alpha_3\beta_1$ integrin receptor and the epinectin ligand, it will be obvious to one skilled in the art that controls will be required including at least non-coated non-adhesive substrata incubated for the same period of time with the test cells. In addition, it will be useful to test the specificity of the adherence of test cells to the epinectin-coated substratum utilizing reagents specifically binding to either the receptor (e.g., monoclonal antibodies, such as P1B5 to the $\alpha_3\beta_1$ integrin receptor, or MAb to the $\alpha_3$ or $\beta_1$ chains; or peptide portions of the epinectin ligand which will competitively or non-competitively inhibit specific binding of the receptor), or alternatively, to the ligand (e.g., monoclonal antibodies to epinectin which will inhibit adhesion of test cells in a specific manner or peptide portions of the $\alpha_3\beta_1$ integrin receptor polypeptide chains which will inhibit the adhesion of test cells in a specific manner).

As an additional test for epinectin complexes, the ability of epinectin to co-distribute on epithelial cells with $\alpha_3\beta_1$, $\alpha_6\beta_4$, or BPA antigens will be useful. Examples of these embodiments of the invention can be found above (see "Epinectin Distribution in Motile and Non Motile HFKs" and "Epinectin Complex is a Ligand for a $\alpha_3\beta_1$-FAs").

12. EXAMPLE 7
Epinectin Complex Adherence of Lymphoid Test Cells

Human peripheral blood lymphocytes lack the cellular $\alpha_3\beta_1$ integrin receptor but acquire this receptor when they are activated in tissue culture with Interleukin-2 and Interleukin-3 (59). Such tissue cultures contain a class of nonspecific "killer" lymphocyte commonly referred to as LAK cells (lymphokine-activated killer cells). LAK have been tested, previously by others, for their potential therapeutic anti-tumor effects in cancer patients by intravenous fusion. One observed property of LAK cells infused in this manner was a capacity to localize nonspecifically in epithelial tissues.

Activated lymphoid cells expressing $\alpha_3\beta_1$ receptors bind in a specific manner to epinectin-coated non-adhesive substrata in the cell adhesion assay described in Example 6, above, or Example 11, below. The binding of activated lymphoid cells to epinectin-coated substrata is inhibited in a specific manner by reagents specifically binding to either the $\alpha_3\beta_1$ receptor or the epinectin ligand, such as that described in Example 6, above and Example 11, below. One of ordinary skill in the art is able to use the test cell assay described here with activated lymphoid cells to screen for reagents (e.g., peptides mimicking the receptor binding domain in epinectin ligand, or alternatively, integrin peptides mimicking the receptor domain which specifically inhibit binding of activated lymphoid cells to epinectin). These reagents are also useful for specifically inhibiting the binding of activated lymphoid cells at sites of chronic and acute inflammation, for example, but not limited to, autoimmune dermatological diseases, rheumatoid arthritis, graft-versus-host disease and transplant rejection sites. Embodiments of the invention relate to activated lymphoid cells which include but are not limited to LAK cells; interleukin, cytokine, and specific antigen-activated T- and B-lymphocytes; and activated mononuclear phagocytes (e.g., but not limited to, treatment with LPS), and/or antigen-activated mast cells (e.g., but not limited to, treatment with allergens).

13. EXAMPLE 8
Wound Healing Compositions

Wound strength depends on cellular and molecular factors which include granulation tissue deposition, deposition of extracellular matrix, and re-epithelialization. Re-epithelialization depends upon migration of epithelial cells from the periphery of the wound site in a migratory tongue into the wound site. This migratory process is encouraged and promoted by epinectin complex, epinectin glycoproteins, and portions thereof; particularly $\alpha_6\beta_4$ and $\alpha_3\beta_1$ receptor binding portions of epinectin ligand. Agents which stimulate increased expression of $\alpha_6\beta_4$ and $\alpha_3\beta_1$ receptors on cells also promote cellular migration, which is advantageous in wound healing.

The epinectin compositions and receptor binding portions disclosed herein promote the formation of SACs, and the proliferation of basal (stem) cells in epithelial tissues by cytokines, since they act as "second signals" to potentiate the action of cytokines. The binding of $\alpha_6\beta_4$ and $\alpha_3\beta_1$ receptors to the epinectin complex serves as a nucleation site for the formation of SACs, and stimulates synthesis of epinectin glycoproteins which ultimately results in a migratory cell becoming stationary. Thus, migratory behavior also promoted by agents which down-regulate epinectin glycoprotein synthesis, or interfere with formation of the epinectin complex. These agents and compositions are within the scope of the embodiments of the invention, and the methods and processes of the invention provide examples of how these agents may be identified.

The premature terminal differentiation of basal (stem) cells in wound sites slows the process of wound healing and contributes to wounds having lesser tensile strength than wounds in which terminal differentiation of epithelial cells can be slowed or completely retarded to allow proliferation of basal (stem) cells. Also, epinectin complex provides a natural basement membrane material for basal (stem) cells and epithelial tissue explants which favors terminal differentiation of the epithelial cells into complex structures such as sweat glands and hair follicles, this process is not currently possible with existing wound healing compositions. Epinectin is also useful for screening reagent compositions in vitro that promote wound healing and epithelial cell growth in vivo, for example, but not limited to, cytokines and growth factors, epinectin peptides, and $\alpha_3\beta_1$ receptor binding partners, such as described in Example 6, above, and in Examples 10 and 11, below.

14. EXAMPLE 9
Role for Epinectin in Polarized Asymmetric Cell Division, and Growth and Differentiation of Cells of Epithelial Origin Asymmetric cell division of epithelial basal cells is characterized by retention of one proliferative daughter cell at the BM (the first daughter cell) and dissociation of the other differentiating daughter (second daughter cell) from the basal layer with movement into the upper layers (i.e., the Malpighian layer of the skin and spinous strata in nervous tissue) (109). In general, $\alpha_3\beta_1$ and epinectin are associated with proliferating basal cells (57, 110, 111), and epinectin synthesis ceases as cells leave the basal layer. Cellular control of asymmetric cell division is manifest through cytoplasmic polarization created by asymmetrical localization of adhesion sites (e.g., SACs and FAs) on the cell plasma membrane of the basal stem cells. Such asymmetry involves cytoplasmic glycoproteins associated with SACs and FAs and their interactions with epinectin and the $\alpha_3\beta_1$ and $\alpha_6\beta_4$ integrins in these structures, e.g., cytoplasmic actin and the 36±15 kd epinectin glycoprotein. These (and other) cytoplasmic glycoprotein components of SACs and FAs bind to cytoplasmic cytoskeletal elements and create the cytoplasmic polarization sufficient to create a first daughter cell which is distinctly different in cytoplasmic organization from the second daughter cell. $\alpha_6\beta_4$ and $\alpha_3\beta_1$ interact with epinectin in the proliferative first daughter at the basal surface of the cell (i.e., in association with BM). $\alpha_3\beta_1$ relocates to proximal sites of intercellular cell-cell adhesion in the basal cell which creates an asymmetrical force upon the differentiating second daughter cell. The lack of physical binding of the second daughter cell to the basement membrane, the down-regulation of epinectin synthesis, and increased cell-cell adhesion in the upper Malpighian or spinous layers creates a physical force to draw the differentiating second daughter away from the proliferative first daughter. Regulation of these polarized adhesion functions facilitates separation of the daughter cells and the resultant polarized/asymmetric cell division in epithelial tissues. Epinectin functions to maintain the proliferative functions of the basal (stem) cells through dual roles in anchoring the cell to the substratum and promoting (as a second signal) the activities of cytokines. Lack of epinectin functions to create the class of "second daughter cells" committed to differentiation. Thus, the epinectin complex, epinectin glycoproteins, and portions thereof (particularly ligand portions which interact with the $\alpha_3\beta_1$ and the $\alpha_6\beta_4$ integrins) are useful for promoting basal (stem) cell growth in epithelial cells and modulation of epinectin synthesis promotes differentiation of epithelial cells such as cancer cells, cells in autoimmune disease states, and cells in psoriasis. Thus, the differentiation of these cells reverses the processes by which the cells cause disease. In addition, $\alpha_3\beta_1$ receptor specific binding partners, such as (for example) antibody to the receptor, promotes aggregation of cells lacking epinectin, and this also is useful for mimicing the effects of epinectin in inducing proliferation and differentiation of epithelial cells.

15. EXAMPLE 10
Use of Epinectin Ligand to Identify the Receptor Binding Portions of the $\alpha_3\beta_1$ and $\alpha_6\beta_4$ Integrin Receptors An alignment of the adjusted $\alpha_6$ amino acid sequence (as reported by Tamura, 56) with the $\alpha_3$ amino acid sequence as they appear in GeneBank results in 37% identity, a value greater than with any other integrin chain. Amino acid sequence of a protein that is related to the functional properties of the protein are frequently evolutionarily conserved. The present finding that epinectin complex binds to both $\alpha_3\beta_1$ and $\alpha_6\beta_4$ provides for the first time a relationship between these two integrin receptors and a functional basis for regions of conserved amino acid sequence(s). Knowing that there is a 37% sequence identity between $\alpha_3$ and $\alpha_6$ and that both $\alpha_3\beta_1$ and $\alpha_6\beta_4$ bind to epinectin, one can select and employ conserved peptide sequence(s) to modulate binding of epinectin ligand to the $\alpha_3\beta_4$ and $\alpha_6\beta_4$ integrin receptors as follows. "Limited sequence portions" of the $\alpha_3$ and $\alpha_6$ chains, i.e., peptides which are at least 30% homologous or identical over at least 3 to 30 amino acids, are identified by direct comparison of the aligned amino acid sequences. From these template "limited sequence portions" in $\alpha_3$ and $\alpha_6$ chains, homologous peptides are constructed ("$\alpha_3$ or $\alpha_6$ test peptides") which are composed of amino acid sequences that are at least 30% homologous and/or identical to the amino acid sequence in the "limited sequence portions." Such "limited sequence portions" and/or "$\alpha_3$ and $\alpha_6$ test peptides" are then assayed pursuant to this disclosure to determine and select "reagent peptides" which will function as inhibitors ("$\alpha_3$ and $\alpha_6$ inhibitory test peptides"), antagonists, and agonists of the natural binding of the $\alpha_3\beta_1$ and $\alpha_6\beta_4$ integrin receptors to the epinectin ligand.

In a representative example, cellular adhesion assays such as those described in Example 6, above, are used to determine and select which of the "limited sequence portions" and "$\alpha_3$ and $\alpha_6$ inhibitory test peptides" inhibit cellular adhesion by at least 20% to epinectin-coated substrata at a physiologically significant molar concentration (i.e., to determine the "$\alpha_3$ or $\alpha_6$ inhibitory peptides"). Test cells are allowed to adhere to epinectin-coated substrata in tissue culture medium within 2 to 24 hours, and preferably 2 to 18 hours, and this adherence of the test cells is inhibited by at least 20% when the "$\alpha_3$ or $\alpha_6$ inhibitory test peptide" is added to the tissue culture medium at a physiologically significant molar concentration, i.e., of $10^{-5}$M to $10^{-10}$M and preferably $10^{-6}$M to $10^{-10}$M. A plurality of assays with a plurality of test cells and "$\alpha_3$ or $\alpha_6$ inhibitory test peptides" are run to identify the "$\alpha_3$ or $\alpha_6$ inhibitory peptide(s)" which inhibit test cell adherence in the assay by at least 20% at a physiologically significant molar concentration.

The selected inhibitors, antagonists, and agonists may be engineered to, e.g., improve their stability, half-life in blood or binding affinity for ligands. Such improvements are made either by substitution of one or more amino acid(s) in the "$\alpha_3$ or $\alpha_6$ inhibitor peptide" for a "natural amino acid" (the "natural amino acid" is that amino acid that is present more than 40% of the time at that particular position when the $\alpha_3$ and $\alpha_6$ chains from at least 5 different animal species are properly aligned). Improvements are also made by biochemical or chemical modification of the "$\alpha_3$ or $\alpha_6$ inhibitor peptide" to create at least one synthetic amino acid, or a plurality of synthetic amino acids, in the amino acid sequence of the "$\alpha_3$ or $\alpha_6$ inhibitor peptide" to produce "$\alpha_3$ and $\alpha_6$ inhibitor analogues." Alternatively, by conformationally modeling the "$\alpha_3$ and $\alpha_6$ inhibitor peptides" and their interaction with epinectin, it is possible to construct an "$\alpha_3$ or $\alpha_6$ inhibitor mimetic" which mimics the "$\alpha_3$ or $\alpha_6$ inhibitor peptide" interaction with epinectin by filling at least 50% of the three-dimensional fluid space occupied by the "$\alpha_3$ or $\alpha_6$ inhibitor peptide" in tissue culture medium at physiological pH and ionic strength when the "$\alpha_3$ or $\alpha_6$ inhibitor peptide" is interacting with the epinectin ligand.

16. EXAMPLE 11

Use of $\alpha_3$ and $\alpha_6$ Inhibitor Peptides; $\alpha_3$ and $\alpha_6$ Inhibitor Analogues; and $\alpha_3$ and $\alpha_6$ Inhibitor Mimetics for Inhibiting the Binding of Lymphoid Test Cells to Epithelial Basement Membrane Compositions Certain of the compositions described in Example 10 are useful for inhibiting the binding of activated T lymphocytes through the integrin receptors to basement membrane compositions having at least epinectin. Using the test cell assay disclosed in Example 7 (above), it is possible to assay a plurality of the inhibitor, antagonist, and agonist compositions disclosed in Example 10 to determine which compositions inhibit by at least 20% the adherence of lymphoid test cells at a physiologically meaningful concentration, e.g., between $10^{-5}$M to $10^{-10}$M (i.e., "lymphoid inhibitory compositions"). The "lymphoid inhibitory compositions" are useful for preventing and slowing the accumulation of activated lymphoid cells (as defined in Example 7) at sites of chronic or acute inflammation, for example (but not limited to) in graft vs. host disease, transplant rejection, autoimmune dermatological and rheumatic diseases, such as rheumatoid and nonrheumatoid arthritis, Bullous pemphigoid, CP, and EBA.

17. EXAMPLE 12

Use of Epinectin Ligand to Identify Autoantibodies in Patient Sera

Epinectin glycoprotein complex and its constituent antigens (as described in Examples 1–3 and as, for example, prepared according to Example 3) are useful for identifying autoantibody in patients with autoimmune disease, for example (but not limited to) greater than 50% of the patients with cicatrical pemphigoid and less than 20% of the patients with BP or EBA; they are useful for distinguishing CP from BP and EBA.

Immunochemical diagnostic assay formats, for example, which are useful include at least enzyme-linked immunoadsorbent assays (ELISA), radioimmuno-assays (RIA), fluorescence immunoassays (FIA), Western immunoblot assays, time-resolved fluorescence assays (TRF), particle agglutination assays (e.g., latex, red cell, etc.). In these assays the bound antibody (or antigen) is separated from free antibody (or antigen) by physical means involving, for example, the use of a solid-phase adsorption of antibody (or antigen) in tubes, microtiter plates, and on polymeric membranes, dipsticks, and beads (e.g., magnetic beads or polystyrene or nylon-66-tm beads); or, alternatively, bound antibody (or antigen) is separated from free antibody (or antigen) through the use of a washing step wherein the assays are run in steps involving at least binding of antibody (or antigen), separation of bound antibody (or antigen) from the free antibody (or antigen) with washing, and assaying for the amount (or presence) of bound antibody (or antigen).

18. EXAMPLE 13

Epinectin Complex for Promoting the Growth of Epithelial Basal (Stem) Cells in Biopsy Materials: Use for Transplantation Epinectin-complex-coated substratum is optimal for promoting the growth of epithelial basal (stem) cells and for preventing the differentiation of this population of cells into other cell types, such as keratinocytes in the skin. For example, primary cultures of epithelial cells, e.g., from biopsy samples, are grown on epinectin-coated in substrata KGM medium and the basal (stem) cells in the samples continue to exhibit mitotic activity (e.g., keratinocyte growth medium, KGM, above; containing growth factors such as (but not limited to), PDGF, EGF, FGF, insulin and serum, such as (but not limited to) 1–10% fetal bovine serum). To confirm the mitotic activity of basal (stem) cells in these cultures, and to distinguish from the mitotic activity of other contaminating cell types (e.g., fibroblasts in skin biopsy samples) it is possible to observe the basal (stem) cells microscopically after fixing, staining, and embedding the cell layer for autoradiography, e.g., using a photographic emulsion. Basal (stem) cells cultured on epinectin-coated substrata retain their mitotic activity for a period of time which is longer than that of biopsy samples grown on control substrata, i.e., HD-BSA; 7 to 14 days is a convenient length of time for assessing this activity (although it is also possible to visually assess the cultures on a daily basis by inverted microscopy, and those skilled in the art are readily able to determine the optimal time for determining mitotic activity in an individual experiment). The mitotic activity is microscopically visible in the autoradiograph as increased numbers of silver grains over the nucleus of the basal (stem) cells. In any cases where doubt may exist as to the nature of the cells in the mitosis assay, it is possible to combine autoradiographic analysis with the uses of immunochemical or other differentiation markers and in these cases, the basal (stem) cells lack the differentiation marker and are thus distinguished.

The ability of epinectin-complex-coated substrata to support mitosis and growth of epithelial basal (stem) cells creates, for the first time, the opportunity to establish tissue cultures of continuously proliferating and differentiating epithelia that mimic normal biological processes and provides a superior source of epithelial cell sheets for transplantation. Such cell sheets are obtained from any epithelial tissue; for example, in the case of skin they are useful for skin transplants; in the case of epithelial cells in the bone marrow and lymphoid tissues they are useful in bone marrow transplantation methods; and, in the case of gastrointestinal ulcers, the cell sheets are useful for repopulating denuded areas of ulcerated tissues through non-invasive transplantation procedures, such as through the use of a catheter.

19. EXAMPLE 14
Therapeutic Compositions

The subject epinectin complex, and epinectin glycoproteins and peptide compositions may be administered to a human patient or other mammalian host in need of treatment by a variety of conventional routes of administration, including orally, parenterally, intravenously, intraperitoneally, intradermally, subcutaneously or intramuscularly. Compositions may also be administered transdermally (as in a lipid-soluble vehicle for a timed-release skin patch), or by nasal or oral instillation into the lungs (as with a nebulizer). In general, these compounds will be administered at dosages between 1 and 250 mg per kg body weight of the subject to be treated per day. However, some variation in dosage will necessarily occur depending on the condition of the patient being treated, and the physician will, in any event, determine the appropriate dose for the individual patient.

Pharmaceutically acceptable salts can be readily prepared from sorbinil and sorbinil analogs by conventional methods. Thus, such salts may be prepared by treating the sorbinil or sorbinil analog with an aqueous solution of the desired pharmaceutically acceptable metallic hydroxide or other metallic base and evaporating the resulting solution to dryness, preferably under reduced pressure. Alternatively, a lower alkanoic solution of the sorbinil or sorbinil analog may be mixed with an alkoxide of the desired metal, and the solution subsequently evaporated to dryness. The pharmaceutically acceptable hydroxides, bases, and alkoxides include those with cations that form metal salts with the acidic compounds of sorbinil and its analogs and that are nontoxic at the dosages administered to a patient in need of treatment. Suitable cations for this purpose include, but are not limited to, potassium, sodium, ammonium, calcium and magnesium.

The compounds may be administered alone or in combination with pharmaceutically acceptable carriers, in either single or multiple doses. Suitable pharmaceutical carriers include inert solid diluents or fillers, sterile aqueous solutions and various nontoxic organic solvents. The pharmaceutical compositions formed by combining the sorbinil or sorbinil analog with the pharmaceutically acceptable carrier are then readily administered in a variety of dosage forms, such as tablets, powders, lozenges, syrups, injectable solutions and the like. These pharmaceutical compositions can, if desired, contain additional ingredients such as flavorings, binders, excipients, and the like. Thus, for purposes of oral administration, tablets containing various excipients such as sodium citrate, calcium carbonate, and calcium phosphate may be employed along with various disintegrants such as starch, and preferably potato or tapioca starch, alginic acid, and certain complex silicates, together with binding agents such as polyvinylpyrrolidine, sucrose, gelatin, and acacia. Additionally, lubricating agents, such as magnesium stearate, sodium lauryl sulfate, and talc are often useful for tableting purposes. Solid compositions of a similar type may also be employed as fillers in salt and hard-filled gelatin capsules; preferred materials for this purpose include lactose or milk sugar and high molecular weight polyethylene glycols. When aqueous suspensions of elixirs are desired for oral administration, the essential active ingredient therein may be combined with various sweetening or flavoring agents, colored matter or dyes, and, if desired, emulsifying or suspending agents, together with diluents such as water, ethanol, propylene glycol, glycerin, and combinations thereof. For parenteral administration, solutions of the sorbinil or sorbinil analog in sesame or peanut oil or in aqueous propylene glycol may be employed, as well as sterile aqueous solutions of the corresponding water soluble pharmaceutically acceptable metal salts previously described. Such an aqueous solution should be suitably buffered if necessary and the liquid diluent first rendered isotonic with sufficient saline or glucose. These particular aqueous solutions are especially suitable for intravenous, intramuscular, subcutaneous and intraperitoneal injection purposes. In this connection, the sterile aqueous media employed are all readily obtainable by standard techniques well known to those skilled in the art. Additionally, it is also possible to administer the aforesaid compounds topically via an appropriate solution suitable for the present purposes at hand.

The subject compounds, when formulated as described above, will typically be packaged with printed instructions specifying their use as anti-cancer or anti-inflammatory compounds, e.g., for reestablishing normal growth control in carcinoma cells, or for inhibiting adhesion of activated lymphoid cells to epithelium, respectively.

20. Materials and Methods
20.1 Cells and Cell Culture

Normal newborn human foreskin keratinocytes (HFKs) were prepared as described by Boyce and Ham (1985) and maintained in serum-free Keratinocyte Growth Medium (KGM; Clonetics, San Diego, Calif.) containing insulin, epidermal growth factor (10 ng/ml), hydrocortisone, and bovine pituitary extract. The FE-A, FEPE1L-8 and FE-H18L cell lines are HFKs that have been transfected with transforming genes E6 and E7 from human papilloma virus 16 and 18 (94; 95).

Primary cultures of human foreskin fibroblasts (HFFs) were prepared by collagenase digestion of neonatal foreskins (e.g., Methods in Enzymology). HT1080 human fibrosarcoma cells were obtained from the American Type Culture Collection (Rockville, Md.). Tera-2 cells, human embryonal carcinoma, were obtained from Dr. Bruce Fenderson (Biomembrane Institute, Seattle, Wash.). OVCAR-4 cells (human ovarian carcinoma and T-47D cells (human mammary tumor) were obtained as gifts from Dr. Arnoud Sonnenberg (Central Lab. of Netherlands Red Cross, Amsterdam Holland). Peroxidase-, fluorescein-, and rhodamine-conjugated (goat) anti-mouse and anti-rat IgG and IgM (H and L chains) or peroxidase and rhodamine-conjugated (goat) anti-rabbit IgG and IgM (H and L chains) were obtained from Tago, Inc. (Burlingame, Calif.).

20.2 Antibodies and Immunochemical Reagents

Peroxidase-, fluorescein-, and rhodamine-conjugated (goat) anti-mouse and anti-rat IgG and IgM (H and L chains) or peroxidase and rhodamine-conjugated (goat) anti-rabbit IgG and IgM (H and L chains) were obtained from Tago, Inc. (Burlingame, Calif.). Fluorescein-conjugated avidin was from Vector Labs (Burlingame, Calif.). N-hydroxysuccinimido-Biotin was from CalBiochem (La Jolla, Calif.).

MAbs to the integrin receptors $\alpha_3\beta_1$ (P1B5, P1F2), $\alpha_2\beta_1$ (P1H5), $\alpha_5\beta_1$ (P1D6), and $\beta_1$ (P4C10) have been described (20, 21, 57, 59, 96). P1H5 and P1D6 inhibit fibroblast, keratinocyte, and platelet adhesion to collagen-coated and fibronectin-coated substrates, respectively (21, 57, 59, 97). MAb P4C10 reacts with all $\beta_1$-containing integrins and inhibits cell adhesion to laminin, collagen, and fibronectin (20, 21). SP2 is a control-conditioned culture medium from the SP2 mouse melanoma. Monoclonal anti-tenascin, F9A5, was prepared in this lab (Maxwell and Carter, unpublished results). Monoclonal anti-$\alpha_6$ (GoH3) was from Dr. Arnoud Sonnenberg (Amsterdam, Holland) and inhibits platelet adhesion to laminin via $\alpha_6\beta_1$ (Sonnenberg et al., 1988) and carcinoma adhesion to laminin via $\alpha_4\beta_4$ (63). Rabbit anti-laminin (R5922) and anti-fibronectin were prepared as previously described (59 and 98, respectively). Mouse MAb 3E1 against integrin $\beta_4$ was a gift from Dr. Eva Engvall (La Jolla Cancer Res. Ctr., La Jolla, Calif.). Rabbit polyclonal antiserum against the carboxy terminus of the Bullous pemphigoid antigen (BPA; R1086) was a gift from Dr. John R. Stanley (Dermatology Branch of the National Institutes of Health, Bethesda, Md.). Rabbit polyclonal anti-entactin was from Upstate Biotechnology, Inc. (Lake Placid, N.Y.).

20.3 Extracellular Matrix Adhesive Ligands

Mouse laminin (derived from EHS sarcoma, grown in mice) was purchased from Collaborative Research Inc. (Bedford, Mass.) or prepared in this lab. Plasma fibronectin and collagen type I were prepared as described (Wayner et al., 1988). Entactin was from Upstate Biotechnology, Inc. (Lake Placid, N.Y.). Tenascin and pepsinized human placental laminin were from Telios (San Diego, Calif.).

20.4 Cellular Adhesion to Extracellular Matrix Adhesive Ligand-Coated Substrates For immunofluorescence and interference reflection microscopy HFK-ECM was prepared by growing HFKs (or HFF) for three days in KGM on acid-washed glass cover slips (25 mm diameter). The adherent cells were removed by a three-step sequential extraction procedure: first, with 1% v/v Triton x-100 detergent (Sigma) in 10 mM sodium phosphate, buffered, pH 7.4, 0.14M saline (PBS); second, with 2M urea/1M NaCl; and, third, with 8M urea. The HFK-ECM was digested with DNase I for 30 minutes in 1% w/v HD-BSA (Sigma)/PBS. The resulting cover slips were washed with PBS, and blocked with HD-BSA (i.e., to avoid nonspecific binding of test antibody to the glass).

To test adhesion of cells to purified extracellular matrix ligands, acid-washed glass cover slips (25 mm diameter) were derivatized with dimethyldichlorosilane (Pierce, Rockford, Ill.); then coated with purified ligands (1 to 10 $\mu$g protein/ml); and finally blocked with 1% w/v HD-BSA in PBS as previously described (20, 21). Cells were adhered to the cover slips in KGM medium for periods of 1 hour to 3 days.

21. Citations

1. Kefalides, N. A., Int. Rev. Connect. Tissue Res. 6:63–104, 1973.
2. Vracko, R., Am. J. Pathol. 77:314–338, 1974.
3. Timpl, R. and Martin, G., IN: Immunochemistry of Collagen (Furthmayr, H., Ed., vol. II, pp. 119–150, CRC Press, Boca Raton, Fla.) 1982.
4. Laurie, G. W. and C. P. Leblond, Histochem. Cytochem. 31:159–163, 1983.
5. Yurchenko, P. and J. C. Schittny, FASEB J. 4:1577–1590, 1990.
6. Orkin, R. W., P. Gehron, E. B. McGoodwin, G. R. Martin, T. Valentine, and J. R. Swarm, J. Exp. Med. 145:204–220, 1977.
7. Timpl, R., H. Rohde, P. Gehron Robey, S. Rennard, J. M. Roidat and G. R. Martin, J. Biol. Chem. 254:9933–9937, 1979.
8. Chung, A. E., R. Juffe, J. L. Freeman, J. P. Vergness, K. E. Broginski, and B. Carlin, Cell 16:277–287, 1979.
9. Carlin, B., R. Jaffe, B. Bender, and A. E. Chung, J. Biol. Chem. 256:5209–5214, 1981.
10. Kanwar, Y. S. and M. G. Farquhar, Proc. Natl. Acad. Sci., U.S.A., 76:4493–4497, 1979.
11. Hassell, J. R., W. C. Leyshon, S. R. Ledbetter, B. Tyree, S. Suzuki, K. Masoto, K. Kimata, and H. K. Kleinman, J. Biol. Chem. 260:8098–8105, 1985.
12. Laemmli, U. K., Nature 227:680–685, 1970.
13. Kleinman, H. K. et al., Biochemistry 25:312–318, 1986.
14. Staehlin, L. A., Int. Rev. Cytol. 39:191–283, 1974.
15. Jones, J. C. R., K. M. Yokoo, and R. D. Goldman, Cell Motil. and Cytoskeleton 6:560–569, 1986.
16. Shienvold, F. L. and D. E. Kelly, Cell Tissue Res. 172:289–307, 1976.
17. Griepp, E. B. and E. S. Robbins, Epithelium in Cell and Tissue Biology. Ed. L. Weiss), Urban & Swarzenburg, Inc., Baltimore, Md., 1988.
18. Burridge, K., K. Fath, T. Kelly, G. Nuckolls, and G. Turner, Ann. Rev. Cell Biol., 4:487–525, 1988.
19. Stepp et al., 1990.
20. Carter, W. G., J. Cell Biol. 111 (in press): 1990.
21. Carter, W. G., E. A. Wayner, T. S. Bouchard, and P. Kaur, 1990, J. Cell Biol., 110:1387–1404.
22. Keene, D. R., L. Y. Sakai, G. P. Lunstrum, N. P. Morris, and R. E. Burgeson, J. Cell Biol. 104:611–620, 1987.
23. Keene et al., 1988.
24. Sakai, L. Y., D. R. Keene, N. P. Morris, and R. E. Burgeson, J. Cell Biol. 103:1577–1586, 1986.
25. Gipson et al., 1983.
26. Stanley, J. R. Clin. Invest. 94:617–623, 1989.
27. Tanaka, T., N. J. Korman, H. Shimizu, R. A. J. Eady, V. Klaus-Kovtun, K. Cehrs, and J. R. Stanley, J. Invest. Dermatol. 94:617–623, 1990.
28. Green, H. and J. G. Rheinwald, U.S. Pat. No. 4,016,036 (1977).
29. Green, H. et al., U.S. Pat. No. 4,304,866 (1981).
30. Green, H. et al., Proc. Nat. Acad. Sci., U.S.A., 76:5665–5668, 1979.

31. Rheinwald and H. Green, Nature 265:421–424; 1977.
32. Kamalti, T., M. Howard, and R. F. Brooks, Development 106:283–293, 1989.
33. Kamalti, T., Z. Mclvor, M. Howard, and M. R. Green, Exp. Cell Res. 185:453–463, 1989.
34. Haake, A. R. and A. T. Lane, In Vitro Develop. Biol. 25:592–560, 1989.
35. Pillai, S., D. D. Bikle, M. Hincenbergs, and P. M. Elias, J. Cell Physiol. 134(2):229–237, 1988.
36. Wilke, M. S., M. Edens, and R. E. Scott, J. Natl. Cancer Inst. 80:1299–1304, 1988.
37. Adams, J. C. and F. M. Watt, J. Cell Biol. 107(5):1927–1938, 1988.
38. Michel, S., R. Schmidt, S. M. Robinson, B. Shroot, and U. Reichert, J. Invest. Dermatol. 88:301–305, 1987.
39. Eckert, R. L. and H. Green, Cell 46:583–589, 1986.
40. Eckert, R. L. and E. A. Rorke, Environ. Health Perspect. 80:109–116, 1989.
41. Watt, F. M., J. Invest. Dermatol. 81(1 Suppl.):100s–103s, 1983.
42. Murphy, G. F., T. C. Flynn, R. H. Rice, and G. S. Pinkus, J. Invest. Dermatol. 82:453–457, 1984.
43. Simon, M. and H. Green, J. Invest. Dermatol. 92:721–724, 1989.
44. Parentau, N. L., R. L. Eckert, and R. H. Rice, Proc. Natl. Acad. Sci., U.S.A. 84:7571–7575, 1987.
45. Hronis, T. S., M. L. Steinberg, V. Defendi, and T. T. Sun, Cancer Res. 44:5797–5804, 1984.
46. Cline, P. R. and R. H. Rice, Canc. Res. 43:3203–3207, 1983.
47. Watt, F. M., J. Invest. Dermatol. 81(1 Suppl.):100s–103s, 1983.
48. Simon, M. and H. Green, Cell 36:827–834, 1984.
49. Simon, M. and H. Green, Cell 40:677–683, 1985.
50. Martin, G. and R. Timpl, Ann. Rev. Cell Biol. 3:57–85, 1987.
51. Beck, K., I. Hunter, and J. Engel, FASEB, 4:148–160, 1990.
52. Hynes, R. O., Cell, 48:549–554, 1987.
53. Rouslahti, E., Ann. Rev. Biochem. 57:375–413, 1988.
54. Hemler, M. E., Immunol. Today 9:109, 1988.
55. Buck, C. F. and A. F. Horwitz, Ann. Rev. Cell Biol. 3:179–205, 1990.
56. Tamura, R. N., C. Rozzo, L. Starr, J. Chambers, L. Reichardt, H. M. Cooper, and V. Quaranta, J. Cell. Biol. 111:1593–1604, 1990.
57. Wayner, E. A., W. G. Carter, R. S. Piotrowicz, and T. J. Kunicki, J. Cell Biol., 107:1881–1891, 1988.
58. DeLuca, M., R. N. Tamura, S. Kajiji, S. Bondanza, P. Rossino, R. Cancedda, P. C. Marchisio, and V. Quaranta, Proc. Natl. Acad. Sci. U.S.A., 87:6888–6892, 1990.
59. Wayner, E. A. and W. G. Carter, J. Cell. Biol. 105:1873–1884, 1987.
60. Santoro, 1986.
61. Elices, M. J. and M. E. Hemler, Proc. Natl. Acad. Sci. U.S.A. 86:9906–9910, 1989.
62. Langvino et al., 1989.
63. Lotz, M. M., C. A. Korzelius, and A. M. Mercurio, Cell Regulation 1:249–257, 1990.
64. Sonnenberg, A., C. J. Linders, P. W. Modderman, C. H. Damsky, M. Aumailley, and R. Timpl, J. Cell Biol. 110:2145–2155, 1990.
65. Gehlsen, K. R., K. Dickerson, W. S. Argraves, E. Engvall, and E. Rouslahti, J. Biol. Chem. 264:19034–19038, 1989.
66. Adams, J. C. and F. M. Watt, Cell 63:425–435, 1990.
67. Stanely, J. R., J. Clin. Invest. 83:1443–1448, 1989.
68. Kaufmann, R., D. Frosch, C. Westphal, L. Weber, and C. Klein, J. Cell Biol. 109:1807–1815, 1989.
69. Larjava, H., J. Peltonen, S. K. Akiyama, H. R. Gralnick, J. Uitto, and K. M. Yamada, J. Cell Biol. 110:, 1990.
70. Hadley et al., J. Cell. Biol. 101:1511–1522, 1985.
71. Madison et al., 1985.
72. Carey, D. and M. Todd, unpublished results and L. Reid, unpublished results cited in Kleinman et al., #13, above.
73. Bernard, B. A., S. M. Robinson, A. Semat, and M. Carmon, Canc. Res. 45:1707–1716, 1985.
74. Said, J. M., A. F. Sassoon, I. P. Shintaku, and S. Banks-Schlegel, J. Invest. Dermatol. 82:449–452, 1984.
75. Murphy, G. F., M. J. Warhol, and R. H. Rice, J. Invest. Dermatol. 82:453–457, 1984.
76. Levitt, M. L., A. F. Gazdar, H. K. Oie, H. Schulter, and S. M. Thacker, Cancer Res. 50:120–128, 1990.
77. Peterson, L. L., J. G. Zettergren, and K. D. Wuepper, J. Invest. Dermatol. 81(1 Suppl.):45s–100s, 1983.
78. Kvedar, J. C., J. Fewkes, and H. P. Baden, Arch. Pathol. Lab. Med. 110:183–188, 1986.
79. Elsayed, A., R. M. Richart, and C. P. Crum, Gynecol. Oncol. 26:25–34, 1987.
80. Harris, H. and M. E. Bramwell, J. Cell Sci. 87:383–388, 1987.
81. Bernard, B. A., S. M. Robinson, S. Vandaele, J. N. Mansbridge, and M. Darmon, Br. J. Dermatol. 112:647–653, 1985.
82. Schaumberg-Lever, W. F., J. Invest. Dermatol. 64:47–49, 1979.
83. Holubar, K., K. Wolfe, E. H. Beutner, J. Invest. Dermatol. 64:220–225, 1975.
84. Honigsmann, H., G. Stingl, K. Holubar, E. Wolff-Schreiner, K. Konrad, and K. Wolff, J. Invest. Dermatol. 66:262, 1976.
85. Nieboer, C., D. M. Boorsma, and M. J. Woerdeman, Br. J. Hematol. 106:419–422, 1983.
86. Fine, J. D., G. R. Neises, and S. I. Katz, J. Invest. Dermatol. 82:39–43, 1984.
87. Yaoita, H., R. A. Briggaman, T. J. Lawley, T. T. Provost, and S. I. Katz, J. Invest Dermatol. 76:288–292, 1981.
88. Stanley, J. R., P. Hawley Nelson, S. H. Yuspa, E. M. Sherach, and S. I. Katz, Cell 24:897–903, 1981.
89. Nisengard, R. J., S. Jablonska, E. H. Beutner, S. Shu, T. P. Chorzelski, M. Jarzabek, M. Blaseyk and G. Rzesa, Oral Surgery 40:365–375, 1975.
90. Woodley, D. T., R. A. Briggaman, E. J. O'Keefe, A. O. Inman, L. L. Queen, and W. R. Gammon, N. Engl. J. Med. 310:1007–1013, 1984.
91. Stanley, J. R., P. Hawley Nelson, S. H. Yuspa, E. M. Shevach, and S. I. Katz, Cell 24:897–903, 1981.
92. Fine, J. D., J. Invest. Dermatol. 82:39–43, 1984.
93. Fine, J. D., Collagen Rel. Res. 5:369–377, 1985.
94. Kaur, P. and J. K. McDougall, J. Virol. 62:1917–1924, 1988.
95. Kaur, P., J. K. McDougall, and R. Cone, J. Gen. Virol. 70:1261–1266, 1989.
96. Wayner, E. A. et al., 1989.
97. Kunicki et al., 1988.
98. Carter, W. G., J. Biol. Chem. 257:13805–13815, 1982.
99. Oi and L. Herzenberg, IN: *Selected Methods in Cellular Immunology* (B. B. Mishell and S. M. Shiigi, Eds.), W. H. Freeman & Co. Publishers, San Francisco, Calif., pp. 351–373, 1980.
100. Taggart and Samloff, Science 219:1228–1230, 1983.
101. Neylakh, A. A., I. S. Tint, T. M. Svitkina, A. D. Bershadsky, and V. I. Gelfand, Exp. Cell. Res. 149:387–396, 1983.

102. Aumailley, M., R. Timpl, and A. Sonnenberg, Exp. Cell Res. 188:55–60, 1990.
103. Katz, S. I., J. Amer. Acad. Dermatol. 11:1025–1037, 1984.
104. Haber et al., 1985.
105. Mar, H. and T. N. Wight, IN: *Colloidal Gold: Principles, Methods, and Applications*, vol. 2, (Ed. M. A. Hayat), Acad. Press, Inc., New York, 1989.
106. Boyce, S. T. and R. G. Ham, J. Tiss. Cult. Meth. 9:83–93, 1985.
107. Towbin et al., Proc. Natl. Acad. Sci. U.S.A. 76:4350–4354, 1979.
108. Michel, S. R. et al., J. Invest. Dermatol. 88:301–305, 1987.
109. Wolpert, L., J. Cell Sci., Suppl. 10:1–9, 1988.
110. Plantefaber, L. C. and R. O. Hynes, Cell 56:281–290, 1989.
111. Hemler, M. E., Immunol. Today 9:109, 1988.

The embodiments of the invention in which an exclusive property or privilege is claimed are defined as follows:

1. A method for identifying a target peptide that modulates the binding of epinectin ligand to $\alpha_3\beta_1$ integrin receptors, comprising:

coating a normally non-adhesive substratum with epinectin;

contacting the epinectin coated substratum with cells expressing $\alpha_3\beta_1$ integrin in the presence of the target peptide;

incubating the cells and the target peptide in a test reaction with the substratum for an incubation period sufficient for the cells to adhere to the substratum;

determining the relative number of cells adhered to the substratum in the test reaction;

determining the relative number of cells adhered to the substratum in a control reaction in which the cells are incubated with an epinectin coated substratum in the absence of the target peptide; and identifying that the target peptide modulates the binding of epinectin to $\alpha_3\beta_1$ integrin receptors if the relative number of cells adhered to the substratum in the test reaction is more or less than the relative number of cells adhered to the substratum in the control reaction.

2. The method of claim 1 wherein the cells and the target peptide are incubated with the substratum for a period of at least 2 hours.

3. The method of claim 1 wherein the cells expressing $\alpha_3\beta_1$ integrin are lymphoid cells.

4. The method of claim 3 wherein the lymphoid cells are lymphokine-activated killer cells.

* * * * *

UNITED STATES PATENT AND TRADEMARK OFFICE
CERTIFICATE OF CORRECTION

PATENT NO.     : 5,830,678
DATED          : November 3 1998
INVENTOR(S)    : W.G. Carter It is certified that error appears in the above-identified patent and that said Letters Patent is hereby corrected as shown below:

Column 1,
Line 12, after "now abandoned." insert a new paragraph
-- This invention was made with government support under grant number CA49259 awarded by the National Institutes of Health. The government has certain rights in the invention. --

Signed and Sealed this

Twenty-second Day of July, 2003

JAMES E. ROGAN
*Director of the United States Patent and Trademark Office*